US011447497B2

(12) United States Patent
Spada et al.

(10) Patent No.: US 11,447,497 B2
(45) Date of Patent: Sep. 20, 2022

(54) (S)-3-(2-(4-(BENZYL)-3-OXOPIPERAZIN-1-YL)ACETAMIDO)-4-OXO-5-(2,3,5,6-TETRAFLUOROPHENOXY)PENTANOIC ACID DERIVATIVES AND RELATED COMPOUNDS AS CASPASE INHIBITORS FOR TREATING CARDIOVASCULAR DISEASES

(71) Applicant: HISTOGEN, INC., San Diego, CA (US)

(72) Inventors: Alfred P. Spada, Carlsbad, CA (US); Robert J. Ternansky, San Diego, CA (US)

(73) Assignee: Histogen, Inc., San Diego, CA (US)

( * ) Notice: Subject to any disclaimer, the term of this patent is extended or adjusted under 35 U.S.C. 154(b) by 0 days.

(21) Appl. No.: 17/256,142

(22) PCT Filed: Jun. 28, 2019

(86) PCT No.: PCT/US2019/039702
§ 371 (c)(1),
(2) Date: Dec. 24, 2020

(87) PCT Pub. No.: WO2020/006341
PCT Pub. Date: Jan. 2, 2020

(65) Prior Publication Data
US 2021/0277014 A1    Sep. 9, 2021

Related U.S. Application Data

(60) Provisional application No. 62/692,517, filed on Jun. 29, 2018.

(51) Int. Cl.
| | |
|---|---|
| *C07D 491/048* | (2006.01) |
| *C07D 241/04* | (2006.01) |
| *C07D 241/08* | (2006.01) |
| *C07D 241/38* | (2006.01) |
| *C07D 401/06* | (2006.01) |
| *C07D 403/06* | (2006.01) |
| *C07D 403/12* | (2006.01) |
| *C07D 405/06* | (2006.01) |
| *C07D 409/06* | (2006.01) |
| *C07D 409/12* | (2006.01) |
| *C07D 471/04* | (2006.01) |

(52) U.S. Cl.
CPC ....... *C07D 491/048* (2013.01); *C07D 241/04* (2013.01); *C07D 241/08* (2013.01); *C07D 241/38* (2013.01); *C07D 401/06* (2013.01); *C07D 403/06* (2013.01); *C07D 403/12* (2013.01); *C07D 405/06* (2013.01); *C07D 409/06* (2013.01); *C07D 409/12* (2013.01); *C07D 471/04* (2013.01)

(58) Field of Classification Search
None
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,044,126 A | 8/1977 | Cook et al. |
| 4,328,245 A | 5/1982 | Yu et al. |
| 4,364,923 A | 12/1982 | Cook et al. |
| 4,409,239 A | 10/1983 | Yu et al. |
| 4,410,545 A | 10/1983 | Yu et al. |
| 4,414,209 A | 11/1983 | Cook et al. |
| 4,522,811 A | 6/1985 | Eppstein et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,323,907 A | 6/1994 | Kalvelage |
| 5,354,556 A | 10/1994 | Sparks et al. |
| 5,591,767 A | 1/1997 | Mohr et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,891,474 A | 4/1999 | Busetti et al. |
| 5,900,252 A | 5/1999 | Calanchi et al. |
| 5,922,356 A | 7/1999 | Koseki et al. |

(Continued)

FOREIGN PATENT DOCUMENTS

| | | |
|---|---|---|
| WO | WO 2008/068615 | 6/2008 |
| WO | WO 2017/117478 A1 | 7/2017 |
| WO | WO 2020/006341 | 1/2020 |

OTHER PUBLICATIONS

Aira et al., "Caspase 1/11 deficiency or pharmacological inhibition mitigates psoriasis-like phenotype in mice." Journal of Investigative Dermatology 139.6 (2019): 1306-1317.

(Continued)

*Primary Examiner* — Samantha L Shterengarts
(74) *Attorney, Agent, or Firm* — Jones Day

(57) ABSTRACT

The present invention relates to (S)-3-(2-(4-(benzyl)-3-oxopiperazin-1-yl)acetamido)-4-oxo-5-(2,3,5,6-tetrafluorophenoxy)pentanoic acid derivatives and related compounds as caspase inhibitors for treating e.g. cardiovascular, kidney, liver, lung, skin, joints, CNS, inflammatory and autoimmune diseases.

20 Claims, No Drawings

(56) References Cited

U.S. PATENT DOCUMENTS

| | | | |
|---|---|---|---|
| 5,972,366 | A | 10/1999 | Haynes et al. |
| 5,972,891 | A | 10/1999 | Kamei et al. |
| 5,980,945 | A | 11/1999 | Ruiz |
| 5,985,307 | A | 11/1999 | Hanson et al. |
| 5,993,855 | A | 11/1999 | Yoshimoto et al. |
| 6,004,534 | A | 12/1999 | Langer et al. |
| 6,039,975 | A | 3/2000 | Shah et al. |
| 6,045,830 | A | 4/2000 | Igari et al. |
| 6,048,736 | A | 4/2000 | Kosak |
| 6,060,082 | A | 5/2000 | Chen et al. |
| 6,071,495 | A | 6/2000 | Unger et al. |
| 6,087,324 | A | 7/2000 | Igari et al. |
| 6,113,943 | A | 9/2000 | Okada et al. |
| 6,120,751 | A | 9/2000 | Unger |
| 6,131,570 | A | 10/2000 | Schuster et al. |
| 6,139,865 | A | 10/2000 | Friend et al. |
| 6,197,350 | B1 | 3/2001 | Yamagata et al. |
| 6,248,363 | B1 | 6/2001 | Patel et al. |
| 6,253,872 | B1 | 7/2001 | Neumann |
| 6,264,970 | B1 | 7/2001 | Hata et al. |
| 6,267,981 | B1 | 7/2001 | Okamoto et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,376,461 | B1 | 4/2002 | Igari et al. |
| 6,419,961 | B1 | 7/2002 | Igari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 2008/0207569 | A1 | 8/2008 | Spada |
| 2008/0207605 | A1 | 8/2008 | Spada |
| 2017/0100448 | A1 | 4/2017 | Spada |
| 2019/0022043 | A1 | 1/2019 | Spada |
| 2020/0283396 | A1 | 9/2020 | Spada et al. |

OTHER PUBLICATIONS

Audia et al., "Caspase-1 inhibition by VX-765 administered at reperfusion in P2Y 12 receptor antagonist-treated rats provides long-term reduction in myocardial infarct size and preservation of ventricular function," Basic research in cardiology 113.5 (2018): 1-15.

Buchwald et al., "Long-term, continuous intravenous heparin administration by an implantable infusion pump in ambulatory patients with recurrent venous thrombosis," Surgery, 88:507 (1980).

Denes et al., "Caspase-1: is IL-1 just the tip of the ICEberg?." Cell death & disease 3.7 (2012): e338-e338.

Flores et al.,"Caspase-1 inhibition alleviates cognitive impairment and neuropathology in an Alzheimer's disease mouse model." Nature communications 9.1 (2018): 1-14.

Goodson, Medical Applications of Controlled Release, vol. 2, pp. 115-138 (1984).

Guo et al., "Targeting inflammasome/IL-1 pathways for cancer immunotherapy." Scientific reports 6.1 (2016): 36107:1-12.

Howard et al., "IL-1-converting enzyme requires aspartic acid residues for processing of the IL-1 beta precursor at two distinct sites and does not cleave 31-kDa IL-1 alpha." The Journal of Immunology 147.9 (1991): 2964-2969.

Kim, R. et al., "Role for NLRP3 Inflammasome-mediated, IL—1b-Dependent Responses in Severe, Steroid-Resistant Asthma" American Journal of Respiratory and Critical Care Medicine 196. 3 (2017) 283-297.

Kostura et al., "Identification of a monocyte specific pre-interlenkin 1 beta convertase activity." Proceedings of the National Academy of Sciences 86.14 (1989): 5227-5231.

Langer, "New methods of drug delivery," Science, 249:1527-1533 (1990).

McKenzie et al., "Caspase-1 inhibition prevents glial inflammasome activation and pyroptosis in models of multiple sclerosis." Proceedings of the National Academy of Sciences 115.26 (2018): E6065-E6074.

Melnikov et al., "Neutrophil-independent mechanisms of caspase-1—and IL-18-mediated ischemic acute tubular necrosis in mice." The Journal of clinical investigation 110.8 (2002): 1083-1091.

Morrison et al., "Intervention with a caspase-1 inhibitor reduces obesity-associated hyperinsulinemia, non-alcoholic steatohepatitis and hepatic fibrosis in LDLR-/-. Leiden mice." International journal of obesity 40.9 (2016): 1416-1423.

Rudolphi et al., "Pralnacasan, an inhibitor of interleukin-1β converting enzyme, reduces joint damage in two murine models of osteoarthritis." Osteoarthritis and cartilage 11.10 (2003): 738-746.

Saudek et al., "A preliminary trial of the programmable implantable medication system for insulin delivery," N. Engl. J. Med., 321:574-579 (1989).

Sefton, "Implantable pumps," CRC Crit. Ref. Biomed. Eng., 14:201 (1987).

Sleath et al., "Substrate specificity of the protease that processes human interleukin-1 beta." Journal of Biological Chemistiy 265.24 (1990): 14526-14528.

Sollberger et al., "Caspase-1: the inflammasome and beyond." Innate immunity 20.2 (2014): 115-125.

Stack et al., "IL-converting enzyme/caspase-1 inhibitor VX-765 blocks the hypersensitive response to an inflammatory stimulus in monocytes from familial cold autoinflammatory syndrome patients." The Journal of Immunology 175.4 (2005): 2630-2634.

Thornberry, Nancy, "Caspases: key mediators of apoptosis." Chemistry & biology 5.5 (1998): R97-R103.

Wang et al., "Caspase-1 causes truncation and aggregation of the Parkinson's disease-associated protein α-synuclein." Proceedings of the National Academy of Sciences 113.34 (2016): 9587-9592.

Wooff et al., "Caspase-1-dependent inflammasomes mediate photoreceptor cell death in photo-oxidative damage-induced retinal degeneration," Scientific reports 10.1 (2020): 1-20.

International Search Report issued for International Application No. PCT/US2019/039702, dated Sep. 4, 2019 (5 pages).

(S)-3-(2-(4-(BENZYL)-3-OXOPIPERAZIN-1-YL)ACETAMIDO)-4-OXO-5-(2,3,5,6-TETRAFLUOROPHENOXY)PENTANOIC ACID DERIVATIVES AND RELATED COMPOUNDS AS CASPASE INHIBITORS FOR TREATING CARDIOVASCULAR DISEASES

RELATED APPLICATIONS

This application is a U.S. National Stage filing under 35 U.S.C. § 371 of International Application No. PCT/US2019/039702, filed Jun. 28, 2019, which claims the benefit of the priority to U.S. Provisional Application Nos. 62/692,517, filed Jun. 28, 2018, the disclosure of each of which is incorporated herein by reference in their entireties.

1. FIELD

Provided herein are novel classes of compounds that are inhibitors of caspases, pharmaceutical compositions containing these compounds and methods of using such compounds and pharmaceutical compositions.

2. BACKGROUND

Caspases include a family of cysteine protease enzymes that are mediators in apoptosis signaling pathways, inflammation and cell disassembly. These enzymes are implicated in several conditions associated with disease and trauma, due to their roles in a variety of apoptotic, non-apoptotic and inflammatory pathways. Inhibitors of caspases can, therefore, prove useful for preventing, ameliorating or treating such conditions.

Peptide and peptidyl inhibitors of caspases have long been known. Such inhibitors, however, have typically been characterized by undesirable pharmacologic properties such as poor oral absorption, poor stability and rapid metabolism (Plattner, J. J. and D. W. Norbeck, in *Drug Discovery Technologies*, C. R. Clark and W. H. Moos, Eds., Ellis Horwood, Chichester, England, 1990, pp. 92-126). These undesirable properties have hampered their development into effective drugs. With a view to overcoming the problems associated with the peptide and peptidyl inhibitors, dipeptide mimetic compounds have been developed (see, e.g., U.S. Pat. Nos. 6,197,750, 6,790,989, 7,960,415, 8,071, 618 and 8,362,043). Due to the far reaching therapeutic implications for inhibitors of a variety of caspases, there however remains a need to identify additional compounds that combine improved properties relative to their peptidic counterparts, such as, for example, improved cell penetration, improved absorption and improved metabolic stability, resulting in enhanced bioavailability and/or potency.

3. SUMMARY

In general, the compounds provided herein incorporate a substituted piperazine moiety as a structural scaffold. The resulting compounds exhibit improved properties relative to peptidyl inhibitors. For example, compounds provided herein have improved properties such as improved metabolic stability, improved solubility and improved pharmacokinetic properties.

In one embodiment, provided herein are the compounds of Formula I:

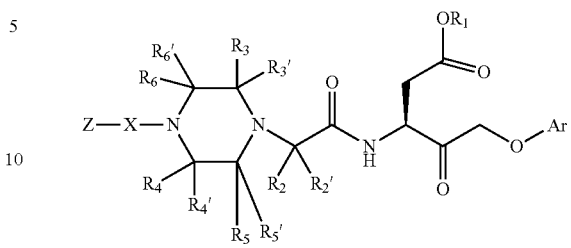

and related compounds of formulae as provided herein, as well as pharmaceutically acceptable salts, solvates, tautomers or isomers thereof, wherein $R_1$, $R_2$, $R_{2'}$, $R_3$, $R_{3'}$, $R_4$, $R_{4'}$, $R_5$, $R_{5'}$, $R_6$, $R_{6'}$, X, Z and Ar are as defined below.

Also provided herein are pharmaceutical compositions containing one or more compound(s) of Formula I and/or related compounds of formulae as provided herein, and a pharmaceutically acceptable carrier.

Also provided herein are methods of treating a disease or condition associated with caspases and/or the modulation of caspases, by administering a therapeutically effective amount of a pharmaceutical composition provided herein to a patient in need of such treatment. Also provided herein are compound(s) of Formula I and/or related compounds of formulae as provided herein, and pharmaceutical compositions thereof, for use in the treatment of a disease or condition associated with caspases and/or the modulation of caspases. Among the conditions or diseases associated with caspases and/or the modulation of caspases are those discussed below. Each of these diseases or conditions can be treated according to the methods provided herein, or the compounds provided herein can be used in the treatment of such diseases or conditions.

Also provided herein are methods of treating liver disease by administering a therapeutically effective amount of a pharmaceutical composition provided herein to a patient in need of such treatment. Also provided herein are compound(s) of Formula I and/or related compounds of formulae as provided herein, and pharmaceutical compositions thereof, Also provided herein are methods of treating gastrointestinal disease by administering a therapeutically effective amount of a pharmaceutical composition provided herein to a patient in need of such treatment.

Also provided herein are methods of treating respiratory disease by administering a therapeutically effective amount of a pharmaceutical composition provided herein to a patient in need of such treatment.

Also provided herein are methods of treating cardiovascular disease by administering a therapeutically effective amount of a pharmaceutical composition provided herein to a patient in need of such treatment.

Also provided herein are methods of treating dermatological disease by administering a therapeutically effective amount of a pharmaceutical composition provided herein to a patient in need of such treatment.

Also provided herein are methods of treating rheumatological diseases by administering a therapeutically effective amount of a pharmaceutical composition provided herein to a patient in need of such treatment.

Also provided herein are methods of treating of treating kidney disease by administering a therapeutically effective amount of a pharmaceutical composition provided herein to a patient in need of such treatment.

Also provided herein are methods of treating autoimmune disease by administering a therapeutically effective amount of a pharmaceutical composition provided herein to a patient in need of such treatment.

Also provided herein are methods of treating CNS disease by administering a therapeutically effective amount of a pharmaceutical composition provided herein to a patient in need of such treatment.

Also provided herein are methods of treating an inflammatory disease by administering a therapeutically effective amount of a pharmaceutical composition provided herein to a patient in need of such treatment.

Among the diseases and conditions for which methods of treatment are provided herein, and compounds for use in the treatment of which are provided herein, include the following:

Inhibition of apoptosis, cardiovascular disorders, dermatological diseases, rheumatological diseases, pathogenic infection, inflammatory disorders, autoimmune disorders, neurodegenerative diseases and trauma (e.g., traumatic spinal cord injury, Amyotrophic Lateral Sclerosis (ALS), traumatic Brain Injury (TBI)), Alzheimer's, Parkinson's and Huntington's diseases, and multiple sclerosis (MS)), sepsis, myocardial infarction (MI), Ischemic Stroke, liver disease, including chronic liver disease and/or clinical consequences thereof. Chronic liver diseases can include, but are not limited to, liver disease caused by viral infection, fatty liver, non-alcoholic fatty liver disease (NAFLD), non-alcoholic steatohepatitis (NASH), hepatitis, including viral and alcoholic hepatitis, primary biliary cholangitis, primary sclerosing cholangitis, Budd-Chiari syndrome and alpha1-antitrypsin deficiency. Clinical consequences of chronic liver disease can include liver fibrosis, liver cirrhosis and portal hypertension.

Inflammatory diseases that can be treated by the methods provided herein, or compounds for use in the treatment of which are provided herein, include chronic and acute diseases such as, for example, autoinflammatory diseases such as Cryopyrin-Associated Periodic Syndromes (CAPS) and neuroinflammatory diseases such as multiple sclerosis (MS), Parkinson's disease and Alzheimer's disease. Treatment of acute inflammatory diseases such as, for example, septic shock, septicemia and adult respiratory distress syndrome also are contemplated by the methods and compounds provided herein. Other target diseases for treatment using the compounds and pharmaceutical compositions provided herein include those associated with ischemic injury, including, for example, myocardial infarction, stroke, and ischemic kidney disease. The compounds and pharmaceutical compositions provided herein also can be used to treat infectious diseases, especially those involved with viral infections. Methods for the treatment of each of these conditions are provided herein.

In certain embodiments, the compounds provided herein can be used in methods for the treatment of chronic liver disease including, NASH, NAFLD, PSC, PBC, alcoholic liver disease and viral liver diseases. In one embodiment, the methods and compounds provided herein are for treatment of clinical consequences of chronic liver disease. In one embodiment, the methods and compounds are for reducing fibrosis associated with chronic liver disease. In one embodiment, the methods and compounds are for reducing fibrosis in patients with liver transplants. In one embodiment, the methods and compounds are for reducing portal hypertension associated with chronic liver disease. In another embodiment, the methods and compounds are for the reduction of cirrhosis. In certain embodiments, the methods and compounds are for treating cirrhosis and/or for further reducing the symptoms associated with cirrhosis. Symptoms of cirrhosis can include, but are not limited to, portal hypertension, abnormal nerve function, ascites (build-up of fluid in the abdominal cavity), breast enlargement in men, coughing up or vomiting blood, curling of fingers (Dupuytren contracture of the palms), gallstones, hair loss, itching, jaundice, kidney failure, liver encephalopathy, muscle loss, poor appetite, redness of palms, salivary gland enlargement in cheeks, shrinking of testes, small spider-like veins in skin, weakness, weight loss, spider angiomas (a central arteriole from which numerous small branching vessels radiate), encephalopathy, and asterixis (flapping tremor).

In one embodiment of a method for treating chronic liver disease, the methods provided herein can lower the elevated level of liver enzyme, such as ALT and AST levels. Methods for measuring the level of elevated liver enzymes are well known in the art (see, e.g., Jeong S. Y. et al. Sandwich ELISA for measurement of cytosolic aspartate aminotransferase in sera from patients with liver diseases, *Clin Chem.*, 2003; 49(5):826 9 and Burin des Roziers N. et al. A microtiter plate assay for measurement of serum alanine aminotransferase in blood donors, *Transfusion.*, 1995; 35(4): 331 4, each of which is incorporated by reference herein in its entirety). In one embodiment, the elevated level of one or more liver enzyme, such as ALT or AST, or the total amount of elevated liver enzyme is reduced by more than about 90% or more than 95%. In one embodiment, the elevated level of one or more liver enzyme, such as elevated levels of ALT or AST, or the total amount of elevated liver enzyme is reduced by at least 95%, at least 90%, at least 80%, at least 70%, at least 60%, at least 50%, at least 40%, at least 30%, at least 20%, at least 10%, at least 5%, at least 2% or at least 1%.

In certain embodiments, provided are methods for treatment of NASH with a combination of current commercially available or experimental treatments for NASH and a caspase inhibitor provided herein. Exemplary compounds and current experimental therapies for treatment of NASH include selonsertib (GS-4997), cenicriviroc, ocaliva (obeticholic acid), elafibranor (GFT505), GS-0976, aramchol, IVA-337 (lanifibranor), saroglitazar, namodenoson (CF102), MN-001 (tipelukast), BI-1467335 (PXS-4782A), volixibat (SHP626), NGM282, GS-9674 (Px-104), LMB-763, LJN-452, semaglutide (NN-9931), IMM-124E, apararenone (MT-3995), MSDC-0602, MGL-3196.

In certain embodiments, provided are methods for treatment of cirrhosis with a combination of current commercially available or experimental treatments for portal hypertension and/or for cirrhosis, and a caspase inhibitor provided herein.

The claims set forth below are incorporated into this section.

4. DETAILED DESCRIPTION OF THE EMBODIMENTS

4.1. Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, "halogen" refers to all halogens, that is, a halogen substituent can be chloro (Cl), fluoro (F), bromo (Br) or iodo (I).

"hydroxyl" or "hydroxy" refer to the group —OH.

"thio" refers to the group —SH.

As used herein, "lower alkyl" means an alkane-derived radical containing from 1 to 6 carbon atoms (unless specifically defined) that includes a straight chain alkyl or branched alkyl. As used herein, the term "alkyl" means a straight or branched $C_1$ to $C_{10}$ carbon chain such as methyl, ethyl, tert-butyl, iso-propyl, n-octyl, and the like. The straight chain or branched alkyl group is chemically feasible and attached at any available point to produce a stable compound. In embodiments, a lower alkyl is a straight or branched alkyl group containing from 1-6, 1-4, or 1-2, carbon atoms, such as methyl, ethyl, propyl, isopropyl, butyl, t-butyl, and the like. A "substituted lower alkyl" denotes lower alkyl that is optionally independently substituted, unless indicated otherwise, with one or more, for example, 1, 2, 3, 4 or 5, also 1, 2, or 3 substituents, attached at any available atom to produce a stable compound, wherein the substituents are selected from the group consisting of —F, —OH, —$NH_2$, —$NO_2$, —CN, —C(O)—OH, —C(S)—OH, —C(O)—$NH_2$, —C(S)—$NH_2$, —S(O)$_2$—$NH_2$, —N(H)—C(O)—$NH_2$, —N(H)—C(S)—$NH_2$, —N(H)—S(O)$_2$—$NH_2$, —C(NH)—$NH_2$, —O—$R^o$, —S—$R^o$, —O—C(O)—$R^o$, —O—C(S)—$R^o$, —C(O)—$R^o$, —C(S)—$R^o$, —C(O)—O—$R^o$, —C(S)—O—$R^o$, —S(O)—$R^o$, —S(O)$_2$—$R^o$, —C(O)—N(H)—$R^o$, —C(S)—N(H)—$R^o$, —C(O)—N($R^o$)—$R^o$, —C(S)—N($R^o$)—$R^o$, —S(O)$_2$—N(H)—$R^o$, —S(O)$_2$—N($R^o$)—$R^o$, —C(NH)—N(H)—$R^o$, —C(NH)—N($R^P$)—$R^c$, —N(H)—C(O)—$R^o$, —N(H)—C(S)—$R^o$, —N($R^o$)—C(O)—$R^o$, —N($R^o$)—C(S)—$R^o$, —N(H)—S(O)$_2$—$R^o$, —N($R^o$)—S(O)$_2$—$R^o$, —N(H)—C(O)—N(H)—$R^o$, —N(H)—C(S)—N(H)—$R^o$, —N($R^o$)—C(O)—$NH_2$, —N($R^o$)—C(S)—$NH_2$, —N($R^o$)—C(O)—N(H)—$R^o$, —N($R^o$)—C(S)—N(H)—$R^o$, —N(H)—C(S)—N($R^o$)—$R^o$, —N(H)—C(S)—N($R^o$)—$R^o$, —N($R^o$)—C(O)—N($R^o$)—$R^o$, —N($R^o$)—C(S)—N($R^o$)—$R^o$, —N(H)—S(O)$_2$—N(H)—$R^o$, —N($R^o$)—S(O)$_2$—$NH_2$, —N($R^o$)—S(O)$_2$—N(H)—$R^o$, —N(H)—S(O)$_2$—N($R^o$)—$R^o$, —N($R^o$)—S(O)$_2$—N($R^o$)—$R^o$, —N(H)—$R^o$, —N($R^o$)—$R^o$, —$R^c$, —$R^f$, and —$R^g$.

"Lower alkylene" refer to a straight or branched divalent hydrocarbon chain consisting solely of carbon and hydrogen, containing no unsaturation and having from one to six carbon atoms, e.g., methylene, ethylene, propylene, n-butylene and the like. In certain embodiment, lower alkylene is substituted with one or more substituent described in the definition of alkyl agroup above.

"Lower alkenyl" alone or in combination means a straight or branched hydrocarbon containing 2-6 carbon atoms (unless specifically defined) and at least one, 1-3, 1-2, or only one, carbon to carbon double bond. The term "alkenyl" means a straight or branched $C_1$ to $C_{10}$ carbon chain containing at least one, 1-3, 1-2, or only one, carbon to carbon double bond. Carbon to carbon double bonds can either be contained within a straight chain or branched portion. The straight chain or branched lower alkenyl group is chemically feasible and attached at any available point to provide a stable compound. Examples of lower alkenyl groups include ethenyl, propenyl, isopropenyl, butenyl, and the like. A "substituted lower alkenyl" denotes lower alkenyl that is optionally independently substituted, unless indicated otherwise, with one or more, for example, 1, 2, 3, 4 or 5, also 1, 2, or 3 substituents, attached at any available atom to produce a stable compound, wherein the substituents are selected from the group consisting of —F, —OH, —$NH_2$, —$NO_2$, —CN, —C(O)—OH, —C(S)—OH, —C(O)—$NH_2$, —C(S)—$NH_2$, —S(O)$_2$—$NH_2$, —N(H)—C(O)—$NH_2$, —N(H)—C(S)—$NH_2$, —N(H)—S(O)$_2$—$NH_2$, —C(NH)—$NH_2$, —O—$R^o$, —S—$R^o$, —O—C(O)—$R^o$, —O—C(S)—$R^o$, —C(O)—$R^o$, —C(S)—$R^o$, —C(O)—O—$R^o$, —C(S)—O—$R^o$, —S(O)—$R^o$, —S(O)$_2$—$R^o$, —C(O)—N(H)—$R^o$, —C(S)—N(H)—$R^o$, —C(O)—N($R^o$)—$R^o$, —C(S)—N($R^o$)—$R^o$, —S(O)$_2$—N(H)—$R^o$, —S(O)$_2$—N($R^o$)—$R^o$, —C(NH)—N(H)—$R^o$, —C(NH)—N($R^P$)—$R^c$, —N(H)—C(O)—$R^o$, —N(H)—C(S)—$R^o$, —N($R^o$)—C(O)—$R^o$, —N($R^o$)—C(S)—$R^o$, —N(H)—S(O)$_2$—$R^o$, —N($R^o$)—S(O)$_2$—$R^o$, —N(H)—C(O)—N(H)—$R^o$, —N(H)—C(S)—N(H)—$R^o$, —N($R^o$)—C(O)—$NH_2$, —N($R^o$)—C(S)—$NH_2$, —N($R^o$)—C(O)—N(H)—$R^o$, —N($R^o$)—C(S)—N(H)—$R^o$, —N(H)—C(O)—N($R^o$)—$R^o$, —N(H)—C(S)—N($R^o$)—$R^o$, —N($R^o$)—C(O)—N($R^o$)—$R^o$, —N($R^o$)—C(S)—N($R^o$)—$R^o$, —N(H)—S(O)$_2$—N(H)—$R^o$, —N($R^o$)—S(O)$_2$—$NH_2$, —N($R^o$)—S(O)$_2$—N(H)—$R^o$, —N(H)—S(O)$_2$—N($R^o$)—$R^o$, —N($R^o$)—S(O)$_2$—N($R^o$)—$R^o$, —N(H)—$R^o$, —N($R^o$)—$R^o$, —$R^d$, —$R^f$, and —$R^g$.

"Lower alkynyl" alone or in combination means a straight or branched hydrocarbon containing 2-6 carbon atoms (unless specifically defined) containing at least one, or only one, carbon to carbon triple bond. The term "alkynyl" means a straight or branched $C_1$ to $C_{10}$ carbon chain containing at least one, or only one, carbon to carbon triple bond. The straight chain or branched lower alkynyl group is chemically feasible and attached at any available point to provide a stable compound. Examples of alkynyl groups include ethynyl, propynyl, butynyl, and the like. A "substituted lower alkynyl" denotes lower alkynyl that is optionally independently substituted, unless indicated otherwise, with one or more, for example, 1, 2, 3, 4 or 5, also 1, 2, or 3 substituents, attached at any available atom to produce a stable compound, wherein the substituents are selected from the group consisting of —F, —OH, —$NH_2$, —$NO_2$, —CN, —C(O)—OH, —C(S)—OH, —C(O)—$NH_2$, —C(S)—$NH_2$, —S(O)$_2$—$NH_2$, —N(H)—C(O)—$NH_2$, —N(H)—C(S)—$NH_2$, —N(H)—S(O)$_2$—$NH_2$, —C(NH)—$NH_2$, —O—$R^o$, —S—$R^o$, —O—C(O)—$R^o$, —O—C(S)—$R^o$, —C(O)—$R^o$, —C(S)—$R^o$, —C(O)—O—$R^o$, —C(S)—O—$R^o$, —S(O)—$R^o$, —S(O)$_2$—$R^o$, —C(O)—N(H)—$R^o$, —C(S)—N(H)—$R^o$, —C(O)—N($R^o$)—$R^o$, —C(S)—N($R^o$)—$R^o$, —S(O)$_2$—N(H)—$R^o$, —S(O)$_2$—N($R^o$)—$R^o$, —C(NH)—N(H)—$R^o$, —C(NH)—N($R^P$)—$R^c$, —N(H)—C(O)—$R^o$, —N(H)—C(S)—$R^o$, —N($R^o$)—C(O)—$R^o$, —N($R^o$)—C(S)—$R^o$, —N(H)—S(O)$_2$—$R^o$, —N($R^o$)—S(O)$_2$—$R^o$, —N(H)—C(O)—N(H)—$R^o$, —N(H)—C(S)—N(H)—$R^o$, —N($R^o$)—C(O)—$NH_2$, —N($R^o$)—C(S)—$NH_2$, —N($R^o$)—C(O)—N(H)—$R^o$, —N($R^o$)—C(S)—N(H)—$R^o$, —N(H)—C(O)—N($R^o$)—$R^o$, —N(H)—C(S)—N($R^o$)—$R^o$, —N($R^o$)—C(O)—N($R^o$)—$R^o$, —N($R^o$)—C(S)—N($R^o$)—$R^o$, —N(H)—S(O)$_2$—N(H)—$R^o$, —N($R^o$)—S(O)$_2$—$NH_2$, —N($R^o$)—S(O)$_2$—N(H)—$R^o$, —N(H)—S(O)$_2$—N($R^o$)—$R^o$, —N($R^o$)—S(O)$_2$—N($R^o$)—$R^o$, —N(H)—$R^o$, —N($R^o$)—$R^o$, —$R^d$, —$R^e$, and —$R^g$.

"Cycloalkyl" refers to saturated or unsaturated, non-aromatic monocyclic, bicyclic or tricyclic carbon ring systems of 3-10, also 3-8 or 3-6, ring members per ring, such as cyclopropyl, cyclopentyl, cyclohexyl, cycloheptyl, cyclooctyl, adamantyl, cis- or trans-decalin, bicyclo[2.2.1]hept-2-ene, cyclohex-1-enyl, cyclopent-1-enyl, 1,4-cyclooctadienyl and the like. The term "(cycloalkyl)alkyl" means the above-defined alkyl group substituted with a cycloalkyl ring. Examples of such a group include (cyclohexyl)methyl, 3-(cyclopropyl)-n-propyl, 5-(cyclopentyl)hexyl, 6-(adamantyl)hexyl, and the like.

A "substituted cycloalkyl" is a cycloalkyl that is optionally independently substituted, unless indicated otherwise, with one or more, for example, 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^P$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, —R$^f$, and —R$^g$ For example, "C$_{3-6}$ cycloalkyl" denotes cycloalkyl containing 3-6 carbon atoms, and "C$_{3-5}$ cycloalkyl" denotes cycloalkyl containing 3-5 carbon atoms.

"Heterocycloalkyl" refers to a saturated or unsaturated non-aromatic cycloalkyl group containing from 5 to 10 atoms in which from 1 to 3 carbon atoms in the ring are replaced by heteroatoms of O, S or N, and optionally are fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon can be oxo substituted, i.e., the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl. "Nitrogen containing heterocycloalkyl" refers to heterocycloalkyl wherein at least one heteroatom is N. The term "(heterocycloalkyl)alkyl" means the above-defined alkyl group substituted with a heterocycloalkyl ring.

A "substituted heterocycloalkyl" is a heterocycloalkyl that is optionally independently substituted, unless indicated otherwise, with one or more, for example, 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^P$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, —R$^f$, and —R$^g$. In some embodiments, the substituents are selected from among one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, lower alkyl, substituted lower alkyl, cycloalkyl, substituted cycloalkyl, (cycloalkyl)alkyl, substituted (cycloalkyl)alkyl, phenyl, substituted phenyl, phenylalkyl, and substituted phenylalkyl groups. In certain embodiments, the substituents are selected from among trifluoromethyl, trichloromethyl, tribromomethyl and triiodomethyl. In some embodiments, the substituents are one or more trifluoromethyl.

The term "substituted phenyl" specifies a phenyl group substituted with one or more substituents chosen from the above-identified "aryl" substituents. In embodiments, the substituents are selected from among halogen, hydroxy, protected hydroxy, cyano, nitro, trifluoromethyl, alkyl, alkoxy, acyl, acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-(lower alkyl)carboxamide, protected N-(lower alkyl)carboxamide, N,N-di(lower alkyl)carboxamide, N-((lower alkyl)sulfonyl) amino, N-(phenylsulfonyl)amino or by a substituted or unsubstituted phenyl group, such that in the latter case a biphenyl or naphthyl group results. Examples of the term "substituted phenyl" include a mono-, di-, tri- or tetra(halo)phenyl group such as 2-, 3- or 4-chlorophenyl, 2,6-dichlorophenyl, 2,5-dichlorophenyl, 3,4-dichlorophenyl, 2,3,5-trichlorophenyl, 2,3,5,6-tetrachlorophenyl, 2-, 3- or 4-bromophenyl, 2,6-dibromophenyl, 2,5-dibromophenyl, 3,4-dibromophenyl, 2,3,5-tribromophenyl, 2,3,5,6-tetrabromophenyl, 2-, 3- or 4-fluorophenyl, 2,6-difluorophenyl, 2,5-difluorophenyl, 3,4-difluorophenyl, 2,3,5-trifluorophenyl, 2,3,5,6-tetrafluorophenyl, 3-chloro-4-fluorophenyl and the like; a mono or di(hydroxy)phenyl group such as 2-, 3-, or 4-hydroxyphenyl, 2,4-dihydroxyphenyl, the protected-hydroxy derivatives thereof and the like; a nitrophenyl group such as 2-, 3-, or 4-nitrophenyl; a cyanophenyl group, for example, 2-, 3- or 4-cyanophenyl; a mono- or di(alkyl) phenyl group such as 2-, 3-, or 4-methylphenyl, 2,4-dimethylphenyl, 2-, 3- or 4-(isopropyl)phenyl, 2-, 3-, or 4-ethylphenyl, 2-, 3- or 4-(n-propyl)phenyl and the like; a mono or di(alkoxy)phenyl group, for example, 2,6-dimethoxyphenyl, 2-, 3- or 4-(isopropoxy)phenyl, 2-, 3- or 4-(t-butoxy) phenyl, 3-ethoxy-4-methoxyphenyl and the like; 2-, 3- or 4-trifluoromethylphenyl; a mono- or dicarboxyphenyl or (protected carboxyphenyl group such as 2-, 3- or 4-carboxyphenyl or 2,4-di(protected carboxy)phenyl; a mono- or di(hydroxymethyl)phenyl or (protected hydroxymethyl)phenyl such as 2-, 3- or 4-(protected hydroxymethyl)phenyl or 3,4-di(hydroxymethyl)phenyl; a mono- or di(aminomethyl) phenyl or (protected aminomethyl)phenyl such as 2-, 3- or 4-(aminomethyl) phenyl or 2,4-(protected aminomethyl) phenyl; or a mono- or di(N-(methylsulfonylamino))phenyl such as 2, 3 or 4-(N(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like.

The term "phenylalkyl" means one of the above phenyl groups attached to one of the above-described alkyl groups, and the term "substituted phenylalkyl" means that either the phenyl, or the alkyl, or both, are substituted with one or more of the above-defined substituents. Examples of "phenylalkyl" substituents include, for example, phenylmethyl (benzyl), phenylethyl, phenylpropyl, phenylisopropyl and the like. Examples of "substituted phenyl" groups include 2-phenyl-1-chloroethyl, 2-(4'-methoxyphenyl)ethyl, 4-(2', 6'-dihydroxy phenyl)n-hexyl, 2-(5'-cyano-3' methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynapth-2-yl)methyl, and the like.

The term "substituted naphthyl" means a naphthyl group substituted with one or more of the above-identified substituents for "aryl" or "phenyl," and the term "(1 or 2 naphthyl)alkyl" means a naphthyl (1 or 2) attached to one of the above-described alkyl groups.

"Heteroaryl" alone or in combination refers to a monocyclic aromatic ring structure containing 5 or 6 ring atoms, or a bicyclic aromatic group having 8 to 10 atoms, containing one or more, e.g., 1-4, 1-3 or 1-2 heteroatoms independently selected from the group consisting of O, S, and N, which optionally can be fused with a cycloalkyl of, for example, 5-7, or, for example, 5-6, ring members. Heteroaryl also is intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups (whether substituted or unsubstituted) include, but are not limited to, pyridinyl, pyridazinyl, pyrazinyl, quinoxalyl, indolizinyl, benzo [b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, pyrrolidinyl, thiadiazolyl, oxadiazolyl, thiatriazolyl, oxatriazolyl, pyridyl, oxazinyl, triazinyl, thiadiazinyl tetrazolo, 1,5-[b]pyridazinyl and purinyl, as well as benzo-fused derivatives, for example, benzoxazolyl, benzothiazolyl, benzimidazolyl, benzofuryl and indolyl. "Nitrogen containing heteroaryl" refers to heteroaryl wherein at least one heteroatom is N. In some instances, for example when R groups of a nitrogen combine with the nitrogen to form a 5 or 7 membered nitrogen containing heteroaryl, any heteroatoms in such 5 or 7 membered heteroaryl are N. An "optionally substituted heteroaryl" is a heteroaryl that is optionally independently substituted, unless indicated otherwise, with one or more, for example, 1, 2, 3, 4 or 5, also 1, 2, or 3 substituents, attached at any available atom to produce a stable compound, wherein the substituents are selected from the group consisting of halogen, —CF$_3$, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, —R$^f$, and —R$^g$.

Substituents for the above optionally substituted heteroaryl rings are as denoted above, e.g., for the "aryl," "phenyl," and "napthyl" groups. In embodiments, the substituents are selected from among one to three halo, trihalomethyl, amino, protected amino, amino salts, mono-substituted amino, di-substituted amino, carboxy, protected carboxy, carboxy late salts, hydroxy, protected hydroxy, salts of a hydroxy group, lower alkoxy, lower alkylthio, lower alkyl, substituted lower alkyl, cycloalkyl, substituted cycloalkyl, (cycloalkyl)alkyl, substituted (cycloalkyl)alkyl, phenyl, substituted phenyl, phenylalkyl, and substituted phenylalkyl groups.

"Pyridyl," as used herein, refers to a 6-membered aromatic ring with one "N" atom. As used herein, "pyridazinyl" refers to a 6-membered aromatic ring with two "N" atoms in the 1 and 2 positions, "pyrimidyl" refers to a 6-membered aromatic ring with two "N" atoms in the 1 and 3 positions and "pyrazinyl" refers to a 6-membered aromatic ring with two "N" atoms in the 1 and 4 positions.

Substituents for the above defined "pyridyl," "pyridazinyl," "pyrimidyl" and "pyrazinyl" groups are as denoted above, e.g., for the "aryl," "phenyl," "napthyl" and "heteroaryl" groups. In some embodiments, the substituents are selected from among one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, lower alkyl, substituted lower alkyl, cycloalkyl, substituted cycloalkyl, (cycloalkyl)alkyl, substituted (cycloalkyl)alkyl, phenyl, substituted phenyl, phenylalkyl, and substituted phenylalkyl groups. In certain embodiments, the substituents are selected from among trifluoromethyl, trichloromethyl, tribromomethyl and triiodomethyl. In some embodiments, the substituents are one or more trifluoromethyl.

The variables $R^o$, $R^p$, $R^c$, $R^d$, $R^e$, $R^f$ and $R^g$ as used in the description of optional substituents for alkyl, alkenyl, alkynyl, cycloalkyl, heterocycloalkyl, aryl, phenyl, napthyl and heteroaryl are defined as follows:

each $R^o$, $R^p$, and $R^c$ are independently selected from the group consisting of $R^d$, $R^e$, $R^f$, and $R^g$, or $R^p$ and $R^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, for example 1, 2, 3, 4 or 5, also 1, 2, or 3 substituents selected from the group consisting of halogen, —NO$_2$, —CN, —OH, —NH$_2$, —O—R$^u$, —S—R$^u$, —N(H)—R$^u$, —N(R$^u$)—R$^u$, —R$^x$, and —R$^y$;

each $R^d$ is independently lower alkyl, wherein lower alkyl is optionally substituted with one or more, for example 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^i$ and —R$^j$;

each $R^e$ is independently lower alkenyl, wherein lower alkenyl is optionally substituted with one or more, for example 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, and —R$^j$;

each $R^f$ is independently lower alkynyl, wherein lower alkynyl is optionally substituted with one or more, for example 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, and —R$^j$;

each $R^g$ is independently selected from the group consisting of cycloalkyl, heterocycloalkyl, aryl, and heteroaryl, wherein cycloalkyl, heterocycloalkyl, aryl, and heteroaryl are optionally substituted with one or more, for example 1, 2, 3, 4 or 5, also 1, 2 or 3 substituents selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N $(R^k)$—$R^k$, —N($R^k$)—S(O)$_2$—N($R^k$)—$R^k$, —N(H)—$R^k$, —N($R^k$)—$R^k$, —$R^h$, —$R^i$ and —$R^j$;

wherein $R^k$, $R^m$, and $R^n$ at each occurrence are independently selected from the group consisting of $R^h$, $R^i$, and $R^j$, or $R^m$ and $R^n$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, for example 1, 2, 3, 4 or 5, also 1, 2, or 3 substituents selected from the group consisting of halogen, —NO$_2$, —CN, —OH, —NH$_2$, —O—$R^u$, —S—$R^u$, —N(H)—$R^u$, —N$R^u R^u$, —$R^x$, and —$R^y$;

wherein each $R^h$ is independently lower alkyl optionally substituted with one or more, for example 1, 2, 3, 4 or 5, also 1, 2, or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—$R^r$, —S—$R^r$, —O—C(O)—$R^r$, —O—C(S)—$R^r$, —C(O)—$R^r$, —C(S)—$R^r$, —C(O)—O—$R^r$, —C(S)—O—$R^r$, —S(O)—$R^r$, —S(O)$_2$—$R^r$, —C(O)—N(H)—$R^r$, —C(S)—N(H)—$R^r$, —C(O)—N($R^r$)—$R^r$, —C(S)—N($R^r$)—$R^r$, —S(O)$_2$—N(H)—$R^r$, —S(O)$_2$—N($R^r$)—$R^r$, —C(NH)—N(H)—$R^r$, —C(NH)—N($R^s$)—$R^t$, —N(H)—C(O)—$R^r$, —N(H)—C(S)—$R^r$, —N($R^r$)—C(O)—$R^r$, —N($R^r$)—C(S)—$R^r$, —N(H)—S(O)$_2$—$R^r$, —N($R^r$)—S(O)$_2$—$R^r$, —N(H)—C(O)—N(H)—$R^r$, —N(H)—C(S)—N(H)—$R^r$, —N($R^r$)—C(O)—NH$_2$, —N($R^r$)—C(S)—NH$_2$, —N($R^r$)—C(O)—N(H)—$R^r$, —N($R^r$)—C(S)—N(H)—$R^r$, —N(H)—C(O)—N($R^r$)—$R^r$, —N(H)—C(S)—N($R^r$)—$R^r$, —N($R^r$)—C(O)—N($R^r$)—$R^r$, —N($R^r$)—C(S)—N($R^r$)—$R^r$, —N(H)—S(O)$_2$—N(H)—$R^r$, —N($R^r$)—S(O)$_2$—NH$_2$, —N($R^r$)—S(O)$_2$—N(H)—$R^r$, —N(H)—S(O)$_2$—N($R^r$)—$R^r$, —N($R^r$)—S(O)$_2$—N($R^r$)—$R^r$, —N(H)—$R^r$, —N($R^r$)—$R^r$, —$R^i$, and —$R^j$;

wherein each $R^i$ is independently selected from the group consisting of lower alkenyl and lower alkynyl, wherein lower alkenyl or lower alkynyl are optionally substituted with one or more, for example 1, 2, 3, 4 or 5, also 1, 2, or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—$R^r$, —S—$R^r$, —O—C(O)—$R^r$, —O—C(S)—$R^r$, —C(O)—$R^r$, —C(S)—$R^r$, —C(O)—O—$R^r$, —C(S)—O—$R^r$, —S(O)—$R^r$, —S(O)$_2$—$R^r$, —C(O)—N(H)—$R^r$, —C(S)—N(H)—$R^r$, —C(O)—N($R^r$)—$R^r$, —C(S)—N($R^r$)—$R^r$, —S(O)$_2$—N(H)—$R^r$, —S(O)$_2$—N($R^r$)—$R^r$, —C(NH)—N(H)—$R^r$, —C(NH)—N($R^s$)—$R^t$, —N(H)—C(O)—$R^r$, —N(H)—C(S)—$R^r$, —N($R^r$)—C(O)—$R^r$, —N($R^r$)—C(S)—$R^r$, —N(H)—S(O)$_2$—$R^r$, —N($R^r$)—S(O)$_2$—$R^r$, —N(H)—C(O)—N(H)—$R^r$, —N(H)—C(S)—N(H)—$R^r$, —N($R^r$)—C(O)—NH$_2$, —N($R^r$)—C(S)—NH$_2$, —N($R^r$)—C(O)—N(H)—$R^r$, —N($R^r$)—C(S)—N(H)—$R^r$, —N(H)—C(O)—N($R^r$)—$R^r$, —N(H)—C(S)—N($R^r$)—$R^r$, —N($R^r$)—C(O)—N($R^r$)—$R^r$, —N($R^r$)—C(S)—N($R^r$)—$R^r$, —N(H)—S(O)$_2$—N(H)—$R^r$, —N($R^r$)—S(O)$_2$—NH$_2$, —N($R^r$)—S(O)$_2$—N(H)—$R^r$, —N(H)—S(O)$_2$—N($R^r$)—$R^r$, —N($R^r$)—S(O)$_2$—N($R^r$)—$R^r$, —N(H)—$R^r$, —N($R^r$)—$R^r$, and —$R^j$;

wherein each $R^j$ is independently selected from the group consisting of cycloalkyl, heterocycloalkyl, aryl, and heteroaryl, wherein cycloalkyl, heterocycloalkyl, aryl, and heteroaryl are optionally substituted with one or more, for example 1, 2, 3, 4 or 5, also 1, 2 or 3 substituents selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—$R^r$, —S—$R^r$, —O—C(O)—$R^r$, —O—C(S)—$R^r$, —C(O)—$R^r$, —C(S)—$R^r$, —C(O)—O—$R^r$, —C(S)—O—$R^r$, —S(O)—$R^r$, —S(O)$_2$—$R^r$, —C(O)—N(H)—$R^r$, —C(S)—N(H)—$R^r$, —C(O)—N($R^r$)—$R^r$, —C(S)—N($R^r$)—$R^r$, —S(O)$_2$—N(H)—$R^r$, —S(O)$_2$—N($R^r$)—$R^r$, —C(NH)—N(H)—$R^r$, —C(NH)—N($R^s$)—$R^t$, —N(H)—C(O)—$R^r$, —N(H)—C(S)—$R^r$, —N($R^r$)—C(O)—$R^r$, —N($R^r$)—C(S)—$R^r$, —N(H)—S(O)$_2$—$R^r$, —N($R^r$)—S(O)$_2$—$R^r$, —N(H)—C(O)—N(H)—$R^r$, —N(H)—C(S)—N(H)—$R^r$, —N($R^r$)—C(O)—NH$_2$, —N($R^r$)—C(S)—NH$_2$, —N($R^r$)—C(O)—N(H)—$R^r$, —N($R^r$)—C(S)—N(H)—$R^r$, —N(H)—C(O)—N($R^r$)—$R^r$, —N(H)—C(S)—N($R^r$)—$R^r$, —N($R^r$)—C(O)—N($R^r$)—$R^r$, —N($R^r$)—C(S)—N($R^r$)—$R^r$, —N(H)—S(O)$_2$—N(H)—$R^r$, —N($R^r$)—S(O)$_2$—NH$_2$, —N($R^r$)—S(O)$_2$—N(H)—$R^r$, —N(H)—S(O)$_2$—N($R^r$)—$R^r$, —N($R^r$)—S(O)$_2$—N($R^r$)—$R^r$, —N($R^r$)—$R^r$, cycloalkylamino, and —$R^x$;

wherein each $R^r$, $R^s$, and $R^t$ at each occurrence are independently selected from the group consisting of lower alkyl, $C_{3-6}$ alkenyl, $C_{3-6}$ alkynyl, cycloalkyl, heterocycloalkyl, aryl and heteroaryl, wherein lower alkyl is optionally substituted with one or more, for example 1, 2, 3, 4 or 5, also 1, 2, or 3 substituents selected from the group consisting of —$R^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein $C_{3-6}$ alkenyl or $C_{3-6}$ alkynyl are optionally substituted with one or more, for example 1, 2, 3, 4 or 5, also 1, 2, or 3 substituents selected from the group consisting of —$R^y$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more, for example 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, or $R^s$ and $R^t$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, for example 1, 2, 3, 4 or 5, also 1, 2, or 3 substituents selected from the group consisting of halogen, —NO$_2$, —CN, —OH, —NH$_2$, —O—R$^u$, —S—R$^u$, —N(H)—R$^u$, —N(R$^u$)—R$^u$, —R$^x$, and —R$^y$;

wherein each R$^u$ is independently selected from the group consisting of lower alkyl, C$_{3-6}$ alkenyl, C$_{3-6}$ alkynyl, cycloalkyl, heterocycloalkyl, aryl, and heteroaryl, wherein lower alkyl is optionally substituted with one or more, for example 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein C$_{3-6}$ alkenyl or C$_{3-6}$ alkynyl are optionally substituted with one or more, for example 1, 2, 3, 4 or 5, also 1, 2, or 3 substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more, for example 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each R$^x$ is selected from the group consisting of lower alkyl, lower alkenyl and lower alkynyl, wherein lower alkyl is optionally substituted with one or more, for example 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein lower alkenyl or lower alkynyl are optionally substituted with one or more, for example 1, 2, 3, 4 or 5, also 1, 2, or 3 substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each R$^y$ is selected from the group consisting of cycloalkyl, heterocycloalkyl, aryl, and heteroaryl, wherein cycloalkyl, heterocycloalkyl, aryl, and heteroaryl are optionally substituted with one or more, for example 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted lower alkenyl, optionally substituted C$_{3-6}$ alkenyl, optionally substituted lower alkynyl, or optionally substituted C$_{3-6}$ alkynyl are optionally substituted with one or more, also 1, 2 or 3 groups or substituents selected from the group consisting of fluoro, —NO$_2$, —CN, —O—R$^{1a}$, —S—R$^{1a}$, —N(R$^{1a}$)—R$^{1a}$, —O—C(O)—R$^{1a}$, —O—C(S)—R$^{1a}$, —C(O)—R$^{1a}$, —C(S)—R$^{1a}$, —C(O)—O—R$^{1a}$, —C(S)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —C(NH)—N(R$^{1a}$)—R$^{1a}$, —N(R$^{1a}$)—C(O)—R$^{1a}$, —N(R$^{1a}$)—C(S)—R$^{1a}$, —N(R$^{1a}$)—S(O)$_2$—R$^{1a}$, —N(R$^{1a}$)—C(O)—N(R$^{1a}$)—R$^{1a}$, —N(R$^{1a}$)—C(S)—N(R$^{1a}$)—R$^{1a}$, —N(R$^{1a}$)—S(O)$_2$—N(R$^{1a}$)—R$^{1a}$, —S(O)—R$^{1a}$, —S(O)$_2$—R$^{1a}$, cycloalkyl, heterocycloalkyl, aryl and heteroaryl; wherein cycloalkyl, heterocycloalkyl, aryl and heteroaryl are optionally substituted with one or more, also 1, 2 or 3 groups or substituents selected from the group consisting of halogen, —NO$_2$, —CN, —O—R$^{1a}$, —S—R$^{1a}$, —N(R$^{1a}$)—R$^{1a}$, —O—C(O)—R$^{1a}$, —O—C(S)—R$^{1a}$, —C(O)—R$^{1a}$, —C(S)—R$^{1a}$, —C(O)—O—R$^{1a}$, —C(S)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —C(NH)—N(R$^{1a}$)—R$^{1a}$, —N(R$^{1a}$)—C(O)—R$^{1a}$, —N(R$^{1a}$)—C(S)—R$^{1a}$, —N(R$^{1a}$)—S(O)$_2$—R$^{1a}$, —N(R$^{1a}$)—C(O)—N(R$^{1a}$)—R$^{1a}$, —N(R$^{1a}$)—C(S)—N(R$^{1a}$)—R$^{1a}$, —N(R$^{1a}$)—S(O)$_2$—N(R$^{1a}$)—R$^{1a}$, —S(O)—R$^{1a}$, —S(O)$_2$—R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$; and all occurrences of optionally substituted cycloalkyl, optionally substituted heterocycloalkyl, optionally substituted 5-7 membered heterocycloalkyl, optionally substituted aryl, optionally substituted heteroaryl, or optionally substituted 5 or 7 membered nitrogen containing heteroaryl are optionally substituted with one or more, also 1, 2, or 3 groups or substituents selected from the group consisting of halogen, —NO$_2$, —CN, —O—R$^{1a}$, —S—R$^{1a}$, —N(R$^{1a}$)—R$^{1a}$, —O—C(O)—R$^{1a}$, —O—C(S)—R$^{1a}$, —C(O)—R$^{1a}$, —C(S)—R$^{1a}$, —C(O)—O—R$^{1a}$, —C(S)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —C(NH)—N(R$^{1a}$)—R$^{1a}$, —N(R$^{1a}$)—C(O)—R$^{1a}$, —N(R$^{1a}$)—C(S)—R$^{1a}$, —N(R$^{1a}$)—S(O)$_2$—R$^{1a}$, —N(R$^{1a}$)—C(O)—N(R$^{1a}$)—R$^{1a}$, —N(R$^{1a}$)—C(S)—N(R$^{1a}$)—R$^{1a}$, —N(R$^{1a}$)—S(O)$_2$—N(R$^{1a}$)—R$^{1a}$, —S(O)—R$^{1a}$, —S(O)$_2$—R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$; wherein R$^{1a}$ is selected from the group consisting of hydrogen, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, and wherein —R$^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted lower alkenyl, optionally substituted C$_{3-6}$ alkenyl, optionally substituted lower alkynyl, or optionally substituted C$_{3-6}$ alkynyl are optionally substituted with one or more, also 1, 2 or 3 groups or substituents selected from the group consisting of fluoro, —CN, —O—R$^{1a}$, —S—R$^{1a}$, —N(R$^{1a}$)—R$^{1a}$, —C(O)—R$^{1a}$, —C(S)—R$^{1a}$, —C(O)—O—R$^{1a}$, —C(O)—N(R$^{1a}$)—

$R^{1a}$, —C(S)—N($R^{1a}$)—$R^{1a}$, —S(O)$_2$—N($R^{1a}$)—$R^{1a}$, —N($R^{1a}$)—C(O)—$R^{1a}$, —N($R^{1a}$)—C(S)—$R^{1a}$, —N($R^{1a}$)—S(O)$_2$—$R^{1a}$, —S(O)—$R^{1a}$, —S(O)$_2$—$R^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —O—$R^{1a}$, —S—$R^{1a}$, —N($R^{1a}$)—$R^{1a}$, —C(O)—$R^{1a}$, —C(S)—$R^{1a}$, —C(O)—O—$R^{1a}$, —C(O)—N($R^{1a}$)—$R^{1a}$, —C(S)—N($R^{1a}$)—$R^{1a}$, —S(O)$_2$—N($R^{1a}$)—$R^{1a}$, —N($R^{1a}$)—C(O)—$R^{1a}$, —N($R^{1a}$)—C(S)—$R^{1a}$, —N($R^{1a}$)—S(O)$_2$—$R^{1a}$, —S(O)—$R^{1a}$, —S(O)$_2$—$R^{1a}$, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$; and all occurrences of optionally substituted cycloalkyl, optionally substituted heterocycloalkyl, optionally substituted 5-7 membered heterocycloalkyl, optionally substituted aryl, optionally substituted heteroaryl, or optionally substituted 5 or 7 membered nitrogen containing heteroaryl are optionally substituted with one or more, also 1, 2, or 3 groups or substituents selected from the group consisting of halogen, —CN, —O—$R^{1a}$, —S—$R^{1a}$, —N($R^{1a}$)—$R^{1a}$, —C(O)—$R^{1a}$, —C(S)—$R^{1a}$, —C(O)—O—$R^{1a}$, —C(O)—N($R^{1a}$)—$R^{1a}$, —C(S)—N($R^{1a}$)—$R^{1a}$, —S(O)$_2$—N($R^{1a}$)—$R^{1a}$, —N($R^{1a}$)—C(O)—$R^{1a}$, —N($R^{1a}$)—C(S)—$R^{1a}$, —N($R^{1a}$)—S(O)$_2$—$R^{1a}$, —S(O)—$R^{1a}$, —S(O)$_2$—$R^{1a}$, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$; wherein $R^{1a}$ is selected from the group consisting of hydrogen, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$, and wherein —$R^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

As used herein, "lower alkoxy" denotes the group —O$R^z$, where $R^z$ is lower alkyl. "Substituted lower alkoxy" denotes lower alkoxy in which $R^z$ is lower alkyl substituted with one or more substituents as indicated herein, for example, in the description of compounds of Formula I, including descriptions of substituted cycloalkyl, heterocycloalkyl, aryl and heteroaryl, attached at any available atom to provide a stable compound. In some embodiments, substitution of lower alkoxy is with 1, 2, 3, 4, or 5 substituents, also 1, 2, or 3 substituents. For example, "fluoro substituted lower alkoxy" denotes lower alkoxy in which the lower alkyl is substituted with one or more fluoro atoms, where in some embodiments, the lower alkoxy is substituted with 1, 2, 3, 4 or 5 fluoro atoms, also 1, 2, or 3 fluoro atoms. It is understood that substitutions on alkoxy are chemically feasible and attached at any available atom to provide a stable compound.

As used herein, "Lower alkylthio" denotes the group —S$R^{aa}$, where $R^{aa}$ is lower alkyl. "Substituted lower alkylthio" denotes lower alkylthio in which $R^{aa}$ is lower alkyl substituted with one or more substituents as indicated herein, for example, in the description of compounds of Formula I, including descriptions of substituted cycloalkyl, heterocycloalkyl, aryl and heteroaryl, attached at any available atom to provide a stable compound. In some embodiments, substitution of lower alkylthio is with 1, 2, 3, 4, or 5 substituents, also 1, 2, or 3 substituents. For example, "fluoro substituted lower alkylthio" denotes lower alkylthio in which the lower alkyl is substituted with one or more fluoro atoms, where in some embodiments the lower alkylthio is substituted with 1, 2, 3, 4 or 5 fluoro atoms, also 1, 2, or 3 fluoro atoms. It is understood that substitutions on alkylthio are chemically feasible and attached at any available atom to provide a stable compound.

As used herein, "amino" or "amine" denotes the group —NH$_2$. "Mono-alkylamino" denotes the group —NH$R^{bb}$ where $R^{bb}$ is lower alkyl. "Di-alkylamino" denotes the group —N$R^{bb}R^{cc}$, where $R^{bb}$ and $R^{cc}$ are independently lower alkyl. "Cycloalkylamino" denotes the group —N$R^{dd}R^{ee}$, where $R^{dd}$ and $R^{ee}$ combine with the nitrogen to form a 5-7 membered heterocycloalkyl, where the heterocycloalkyl can contain an additional heteroatom within the ring, such as O, N, or S, and can also be further substituted with lower alkyl. Examples of 5-7 membered heterocycloalkyl include, but are not limited to, piperidine, piperazine, 4-methylpiperazine, morpholine, and thiomorpholine. It is understood that when mono-alkylamino, di-alkylamino, or cycloalkylamino are substituents on other moieties, these are chemically feasible and attached at any available atom to provide a stable compound.

It is understood that all possible substitutions as defined above include subsets of these substitutions, such as are indicated herein, for example, in the description of compounds of Formula I, attached at any available atom to produce a stable compound. For example, "fluoro substituted phenyl" denotes a phenyl group substituted with one or more fluoro atoms where, for example, the phenyl is substituted with 1, 2, 3, 4 or 5 fluoro atoms, e.g., 2,3,5,6-tetrafluorophenyl. It also is understood that any of the substitutions made according to the definitions above are chemically feasible and attached at any available atom to provide a stable compound.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, (trimethylsilyl)ethyl, (di(n-butyl) methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups can be found in C. B. Reese and E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, methoxyethoxymethyl, methylthiomethyl, t-butyl, t-amyl, trityl, 4-methoxytrityl, 4,4'-dimethoxytrityl, 4,4',"'-trimethoxytrityl, benzyl, allyl, trimethylsilyl, (t-butyl) dimethylsilyl, 2, 2,2-trichloroethoxycarbonyl, and the like. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3. An exemplary hydroxy-protecting group is the tert-butyl group. The related term "protected hydroxy" denotes a hydroxy group bonded to one of the above hydroxy protecting groups.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom. Examples of such amino-protecting groups include the formyl ("For") group, the trityl group, the phthalimido group, the trichloroacetyl group, the trifluoroacetyl group, the chloroacetyl, bromoacetyl, and iodoacetyl groups, urethane-type protecting groups, such as t-butoxycarbonyl ("Boc"), 2-(4-biphenylyl)propyl-2-oxycarbonyl ("Bpoc"), 2-5 phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl) propyl-2-oxycarbonyl Ddz"), 2-p-toluyl)propyl-2-oxycarbonyl, cyclopentenyl-oxycarbonyl, 1-methylcyclopentanyl-oxycarbonyl, cyclohexanyloxycarbonyl, 1-methyl-cyclohexanyloxy-carbonyl, 2-methylcyclohexanyl-oxycarbonyl, 2-(4-toluylsulfonyl) ethoxycarbonyl, 2-(methylsulfonyl) ethoxycarbonyl, 2-(triphenylphosphino)-ethoxycarbonyl, 9-fluorenyl-methoxycarbonyl ("Fmoc"), 2-(trimethylsilyl) ethoxy carbonyl, allyloxycarbonyl, 1-(trimethylsilylmethyl) prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyl-oxycarbonyl ("Cbz"), 4-phenylbenzyloxycarbonyl, 2-methylbenzyloxycarbonyl, a-2,4,5,-tetramethylbenzyl-oxycarbonyl ("Tmz"), 4-methoxybenzyloxycarbonyl, 4-fluorobenzyl-oxycarbonyl, 4-chlorobenzyloxycarbonyl, 3-chlorobenzyloxycarbonyl, 2-chlorobenzyloxy-carbonyl, 2,4-dichlorobenzyloxycarbonyl, 4-bromobenzyloxycarbonyl, 3-bromobenzyloxy-carbonyl, 4-nitrobenzyloxycarbonyl, 4-cyanobenzyloxycarbonyl, 4-(decyloxy)benzyloxycarbonyl and the like; the benzoylmethylsulfonyl group, the 2,2,5,7,8-pentamethylchroman-6-sulfonyl group ("PMC"), the dithiasuccinoyl ("Dts") group, the 2-(nitro)phenyl-sulfenyl group ("Nps"), the diphenylphosphine oxide group, and like amino-protecting groups. The species of amino protecting group employed is not critical so long as the derivatized amino group is stable to the conditions of the subsequent reaction(s) and can be removed at the appropriate point without disrupting the remainder of the molecule. Exemplary amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised Ed., Springer-Verlag, New 65 York, N.Y., 1984 and 1993, and J. M. Stewart and J. D. Chemical Co., Rockford, Ill., 1984, E. Atherton and R. C. Shephard, "Solid Phase Peptide Synthesis—A Practical Approach" IRL Press, Oxford, England (1989), each of which is incorporated herein by reference. The related term "protected amino" defines an amino group substituted with an amino-protecting group discussed above.

It is to be understood that the compounds provided herein can contain chiral centers. Such chiral centers can be of either the (R) or (S) configuration, or can be a mixture thereof. Thus, the compounds provided herein can be enantiomerically pure, or be stereoisomeric or diastereomeric mixtures. As such, one of skill in the art will recognize that administration of a compound in its (R) form is equivalent, for compounds that undergo epimerization in vivo, to administration of the compound in its (S) form.

As used herein, "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers can be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

In certain embodiments, the compound used in the methods provided herein is "stereochemically pure." A stereochemically pure compound or has a level of stereochemical purity that would be recognized as "pure" by those of skill in the art. In certain embodiments, "stereochemically pure" designates a compound that is substantially free of alternate isomers. In particular embodiments, the compound is 85%, 90%, 91%, 92%, 93%, 94%, 95%, 96%, 97%, 98%, 99%, 99.5% or 99.9% free of other isomers.

The singular forms "a," "an," and "the" include plural references, unless the context clearly dictates otherwise.

As used herein "subject" is an animal, such as a mammal, including human, such as a patient.

As used herein, "biological activity" refers to the in vitro or in vivo activities of a compound, or physiological responses that result upon in vivo administration of a compound, composition or other mixture. Biological activity, thus, encompasses therapeutic effects and pharmacokinetic behavior of such compounds, compositions and mixtures. Biological activities can be observed in in vitro and in vitro systems designed to test for such activities.

As used herein, "pharmaceutically acceptable derivatives" of a compound include salts, esters, acetals, ketals, orthoesters, hemiacetals, hemiketals, acids, bases, solvates, hydrates or prodrugs thereof. Such derivatives can readily be prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable solvates and hydrates are complexes of a compound with one or more solvent or water molecules, or 1 to about 100, or 1 to about 10, or one to about 2, 3 or 4, solvent or water molecules.

As used herein, "treatment" means any manner in which a disease or disorder, or one or more of the symptoms of a disease or disorder, are ameliorated or otherwise beneficially altered. Treatment also encompasses any pharmaceutical use of the compositions herein, such as use for treating cancer.

As used herein, "prevention" means any manner in which the risk of contracting a disease or disorder, or of experiencing one or more of the symptoms of a disease or disorder, is reduced. Such risk can be reduced by, for example, between about 5% to 100%, such as by about 5, 10, 15, 20, 25, 30, 35, 40, 45, 50, 55, 60, 65, 70, 75, 80, 85, 90, 95 or 100%.

As used herein, "amelioration" or "mitigation" of the symptoms of a particular disorder by administration of a particular compound or pharmaceutical composition are used interchangeably and refers to any lessening of the symptoms, whether permanent or temporary, lasting or transient that can be attributed to or associated with administration of the compound or composition.

As used herein, "complication" refers to a condition that develops in association with a condition or disease. The complication can be as a direct result caused by the condition or disease, or can be associated with the existence of the primary condition or disease. In some embodiments, the complications of a disease can be manifested as a symptom and, in those instances, the two terms are used interchangeably herein.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, the term "in combination" refers to the use of more than one therapies (e.g., a caspase inhibitor and other agents). The use of the term "in combination" does not restrict the order in which therapies (e.g., a caspase inhibitor and other agents) are administered to a subject with a disorder. A first therapy (e.g., a caspase inhibitor and other agents) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of other therapy (e.g., a caspase inhibitor and other agents) to a subject with a disorder.

The term "parenteral" as used herein includes administration of a compound to a subject using subcutaneous, intracutaneous, intravenous, intramuscular, intraarticular, intrasynovial, intrasternal, intrathecal, intralesional and intracranial injection or infusion techniques.

As used herein, the term "synergistic" refers to a combination of a caspase inhibitor with another agent, which is more effective than the additive effects of the administration of the two compounds as monotherapies. A synergistic effect of a combination of therapies (e.g., a caspase inhibitor and another agent) permits the use of lower dosages of one or more of the therapies and/or less frequent administration of the therapies to a subject with a disorder. The ability to utilize lower dosages of a therapy (e.g., a caspase inhibitor and another agent) and/or to administer the therapy less frequently reduces the toxicity associated with the administration of the therapy to a subject without reducing the efficacy of the therapy in the prevention or treatment of a disorder. In addition, a synergistic effect can result in improved efficacy of agents in the prevention or treatment of a disorder. Finally, a synergistic effect of a combination of therapies (e.g., a caspase inhibitor and another agent) can avoid or reduce adverse or unwanted side effects associated with the use of either therapy alone.

4.2. Caspases in Medicine

There are ten known human caspases. Interleukin converting enzyme (ICE), also known as caspase-1, was the first identified caspase. The caspases have been classified in two groups, based on their effects: proapoptotic caspases (caspases 2, 3, 6, 7, 8, 9 and 10) or proinflammatory caspases (caspases 1, 4 and 5).

Caspases are implicated in several conditions based on their effects through various pathways, including, apoptotic, non-apoptotic and inflammatory. Inhibitors of caspases have been shown to prevent apoptosis of cells in tissue culture studies and in various animal models of disease as described in Hoglen, N. et al. Characterization of IDN-6556 (3-{2-(2-tert-butylphenylaminooxalyl)-amino]-propionylamino}-4-oxo-5-(2,3,5,6-tetrafluoropenoxy)-pentanoic acid): a liver-targeted caspase inhibitor. *J. Pharm. Exp. Therapeutics.* 2003; 309: 634-640. However, it also is known that caspases regulate multiple processes in addition to apoptosis Connolly, P. et al. New roles for old enzymes: killer caspases as the engine of cell behavior changes. *Frontiers in Physiology* 2014; 5: doi. 10.3389/fphys.2014.00149.

The multi-pronged effects of caspases generate a variety of potential medical applications for caspase inhibitors. For example, it is known that proapoptotic caspases are involved in the pathogenesis of many cardiovascular disorders. Caspase-1 plays an important role in pathogenic infection as well as in inflammatory and autoimmune disorders. Caspases also play a role in neurodegenerative diseases and trauma. For example, the caspase-3 cascade is activated due to the traumatic spinal cord injury. The activation of caspase-1 and caspase-3 in Amyotrophic Lateral Sclerosis (ALS) patients and the activation of caspase-7, -8, and -9 in a mouse model at the end stage of ALS have been reported. Increased levels of apoptosis and caspase activity (especially caspase-3) are reported to be frequently observed at sites of cellular damage in both acute (e.g., sepsis, myocardial infarction (MI), Ischemic Stroke, Spinal cord injury (SCI), traumatic Brain Injury (TBI)) and neurodegenerative disease (e.g., Alzheimer's, Parkinson's and Huntington's diseases, and multiple sclerosis (MS)).

Caspase inhibitor compounds, such as those provided herein, also can be used to reduce apoptosis, inflammation and tissue damage in models of liver disease. For example, caspase inhibitors can be used to improve liver function in subjects with chronic liver disease and/or to treat, prevent or ameliorate of one or more clinical consequences of a chronic liver disease. Chronic liver diseases include, but are not limited to, liver disease caused by viral infection, fatty liver, non-alcoholic fatty liver disease (NAFLD), non-alcoholic steatohepatitis (NASH), hepatitis, including viral and alcoholic hepatitis, primary biliary cholangitis, primary sclerosing cholangitis, Budd-Chiari syndrome and alpha1-antitrypsin deficiency. Chronic liver disease can lead to liver fibrosis and liver cirrhosis. The cytokines interleukins 1 beta, (IL-1β) and interleukin 18 (IL-18), mediate inflammation in the liver and are linked to chronic liver disease. Thus, prevention or suppression of inflammation in the liver is a component in the treatment of chronic liver disease. IL-1β and IL-18 require the action of caspases to activate their individual inflammatory activities from their respective precursor proteins, pro-IL1 beta and pro-IL-18. The precursor proteins, pro-IL1 beta and pro-IL-18, lack inflammatory activity. Without being bound by any particular theory, it is believed that in certain instances, the prevention or suppression of excessive inflammation in the liver by caspase inhibitor compounds, such as those provided herein, can contribute to reducing liver damage associated with chronic liver disease.

In addition, caspase inhibitors can prevent, ameliorate or treat portal hypertension, which can result from chronic liver disease and is characterized by elevated blood pressure in the liver, as measured by a hepatic venous pressure gradient (HVPG) of greater than 5 mmHg. High HVPG is predictive of the development of seriously debilitating and potentially life-threatening conditions such as esophageal varices, ascites, hepatic encephalopathy and variceal hemorrhage. Without being bound by any particular theory, it is believed that the caspase inhibitors provided herein can act by inhibiting apoptosis and/or inflammation and the generation and signaling of vasoactive cytokines that affect the liver and intestinal vascular system that leads to portal hypertension.

In view of the multiple uses for caspase inhibitors, and the challenges in selectively treating various conditions in which caspases are implicated, there is a constant need to develop new, more effective compounds for use in therapies.

4.3. Caspase Inhibitor Compounds

Provided herein are compounds of Formula I:

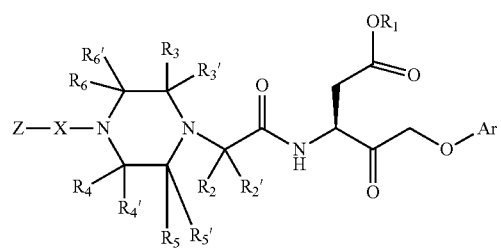

Formula I or pharmaceutically acceptable salts, solvates, tautomers or isomers thereof, wherein:

Z is aryl, arylalkyl, heteroaryl or heteroarylalkyl, each of which is optionally substituted;

Ar is phenyl, phenylalkyl, naphthyl, naphthylalkyl or heteroaryl, each of which is optionally substituted;

X is a bond, $SO_2$, SO, CO, or optionally substituted lower alkylene;

$R_1$ is hydrogen, lower alkyl, cycloalkyl, (cycloalkyl)alkyl or optionally substituted phenylalkyl;

$R_2$ and $R_{2'}$ are selected as follows:
  i) $R_2$ and $R_{2'}$ are each independently hydrogen, fluoro, —OH, —$NH_2$, lower alkyl, lower alkoxy, lower alklylthio, mono-alkylamino or di-alkylamino, wherein the alkyl chain(s) of lower alkyl, lower alkoxy, lower alkylthio, mono-alkylamino, or di-alkylamino are optionally substituted with one or more substituents selected from the group consisting of halogen, —OH, —$NH_2$, lower alkoxy, halogen substituted lower alkoxy, lower alkylthio, halogen substituted lower alkylthio, mono-alkylamino, di-alkylamino, and cycloalkylamino; or
  ii) $R_2$ and $R_{2'}$ combine with the carbon to which they are attached to form a 3-7 membered monocyclic cycloalkyl or 5-7 membered monocyclic heterocycloalkyl, wherein the monocyclic cycloalkyl or monocyclic heterocycloalkyl are optionally substituted with one or more substituents selected from the group consisting of halogen, —OH, —$NH_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

$R_3$, $R_{3'}$, $R_4$, $R_{4'}$, $R_5$, $R_{5'}$, $R_6$ and $R_{6'}$ are selected as follows:
  i) $R_3$, $R_{3'}$, $R_4$, $R_{4'}$, $R_5$, $R_{5'}$, $R_6$ and $R_{6'}$ are each independently hydrogen, optionally substituted lower alkyl, optionally substituted $C_{2-6}$ alkenyl, optionally substituted $C_{2-6}$ alkynyl, optionally substituted aryl, optionally substituted heteroaryl, optionally substituted arylalkyl or optionally substituted heteroarylalkyl;
  ii) $R_3$, $R_{3'}$ and $R_6$, $R_{6'}$ together form an optionally substituted aryl, optionally substituted heteroaryl ring, and $R_4$, $R_{4'}$, $R_5$ and $R_{5'}$ are each independently hydrogen, optionally substituted lower alkyl, optionally substituted $C_{2-6}$ alkenyl, optionally substituted $C_{2-6}$ alkynyl, optionally substituted aryl, optionally substituted heteroaryl, optionally substituted arylalkyl or optionally substituted heteroarylalkyl;

iii) $R_4$, $R_{4'}$ and $R_5$, $R_{5'}$ together form an optionally substituted aryl or optionally substituted heteroaryl ring, and $R_3$, $R_{3'}$, $R_6$ and $R_{6'}$ are each independently hydrogen, optionally substituted lower alkyl, optionally substituted $C_{2-6}$ alkenyl, optionally substituted $C_{2-6}$ alkynyl, optionally substituted aryl, optionally substituted heteroaryl, optionally substituted arylalkyl or optionally substituted heteroarylalkyl, with the proviso that when $R_3$, $R_{3'}$ and $R_6$, $R_{6'}$ together form an aryl, substituted aryl, heteroaryl or substituted heteroaryl ring, $R_4$, $R_{4'}$ and $R_5$, $R_{5'}$ cannot together form an aryl, substituted aryl, heteroaryl or substituted heteroaryl ring and when $R_4$, $R_{4'}$ and $R_5$, $R_{5'}$ together form an aryl, substituted aryl, heteroaryl or substituted heteroaryl ring, $R_3$, $R_{3'}$ and $R_6$, $R_{6'}$ cannot together form an aryl, substituted aryl, heteroaryl or substituted heteroaryl ring; or iv) $R_3$ and $R_{3'}$ together, $R_4$ and $R_{4'}$ together, $R_5$ and $R_{5'}$ together or $R_6$ and $R_{6'}$ together is oxo (i.e., =O), and all substituents for $R_3$, $R_{3'}$, $R_4$, $R_{4'}$, $R_5$, $R_{5'}$, $R_6$ and $R_{6'}$ other than the oxo being as defined in i), ii) and iii) above, with the proviso that:

when $R_3$ and $R_{3'}$ together is oxo, none or one of $R_4$ and $R_{4'}$ together, $R_5$ and $R_{5'}$ together and $R_6$ and $R_{6'}$ together is oxo, when $R_4$ and $R_{4'}$ together is oxo, none or one of $R_3$ and $R_{3'}$ together, $R_5$ and $R_{5'}$ together and $R_6$ and $R_{6'}$ together is oxo, when $R_5$ and $R_{5'}$ together is oxo, none or one of $R_3$ and $R_{3'}$ together, $R_4$ and $R_{4'}$ together and $R_6$ and $R_{6'}$ together is oxo, and when $R_6$ and $R_{6'}$ together is oxo, none or one of $R_3$ and $R_{3'}$ together, $R_4$ and $R_{4'}$ together and $R_5$ and $R_{5'}$ together is oxo, wherein, unless specified otherwise, the substituents on cycloalkyl, aryl, heterocycloalkyl, and heteroaryl groups, when present are selected from one or more, in one embodiment, 1 to 5, in one embodiment, 1 to 4, or in one embodiment, 1 to 3, substituents $Q^1$, wherein each $Q^1$ is independently selected from halogen, —OH, —$NH_2$, —$NO_2$, —CN, —C(O)—OH, —C(S)—OH, —C(O)—$NH_2$, —C(S)—$NH_2$, —S(O)$_2$—$NH_2$, —N(H)—C(O)—$NH_2$, —N(H)—C(S)—$NH_2$, —N(H)—S(O)$_2$—$NH_2$, —C(NH)—$NH_2$, —O—$R^o$, —S—$R^o$, —O—C(O)—$R^o$, —S—$R^o$, —O—C(O)—$R^o$, —O—C(S)—$R^o$, —C(O)—$R^o$, —C(S)—$R^o$, —C(O)—O—$R^o$, —C(S)—O—$R^o$, —S(O)—$R^o$, —S(O)$_2$—$R^o$, —C(O)—N(H)—$R^o$, —C(S)—N(H)—$R^o$, —C(O)—N($R^o$)—$R^o$, —C(S)—N($R^o$)—$R^o$, —S(O)$_2$—N(H)—$R^o$, —S(O)$_2$—N($R^o$)—$R^o$, —C(NH)—N(H)—$R^o$, —C(NH)—N($R^p$)—$R^c$, —N(H)—C(O)—$R^o$, —N(H)—C(S)—$R^o$, —N($R^o$)—C(O)—$R^o$, —N($R^o$)—C(S)—$R^o$, —N(H)—S(O)$_2$—$R^o$, —N($R^o$)—S(O)$_2$—$R^o$, —N(H)—C(O)—N(H)—$R^o$, —N(H)—C(S)—N(H)—$R^o$, —N($R^o$)—C(O)—$NH_2$, —N($R^o$)—C(S)—$NH_2$, —N($R^o$)—C(O)—N(H)—$R^o$, —N($R^o$)—C(S)—N(H)—$R^o$, —N(H)—C(O)—N($R^o$)—$R^o$, —N(H)—C(S)—N($R^o$)—$R^o$, —N($R^o$)—C(O)—N($R^o$)—$R^o$, —N($R^o$)—C(S)—N($R^o$)—$R^o$, —N(H)—S(O)$_2$—N(H)—$R^o$, —N(H)—S(O)$_2$—$NH_2$, —N($R^o$)—S(O)$_2$—N(H)—$R^o$, —N(H)—S(O)$_2$—N($R^o$)—$R^o$, —N($R^o$)—S(O)$_2$—N($R^o$)—$R^o$, —N(H)—$R^o$, —N($R^o$)—$R^o$, —$R^d$, —$R^e$, —$R^f$, and —$R^g$;

unless specified otherwise, the substituents on alkyl, alkenyl and alkynyl groups, when present are selected from one or more, in one embodiment, 1 to 5, in one embodiment, 1 to 4, or in one embodiment, 1 to 3, substituents $Q^2$, wherein each $Q^2$ is independently selected from —F, —OH, —$NH_2$, —$NO_2$, —CN, —C(O)—OH, —C(S)—OH, —C(O)—$NH_2$, —C(S)—$NH_2$, —S(O)$_2$—$NH_2$, —N(H)—C(O)—$NH_2$, —N(H)—C(S)—$NH_2$, —N(H)—S(O)$_2$—$NH_2$, —C(NH), —$NH_2$, —O—$R^o$, —S—$R^o$, —O—C(O)—$R^o$, —O—C(S)—$R^o$, —C(O)—$R^o$, —C(S)—$R^o$, —C(O)—O—$R^o$, —C(S)—O—$R^o$, —S(O)—$R^o$, —S(O)$_2$—$R^o$, —C(O)—N(H)—$R^o$, —C(S)—N(H)—$R^o$, —C(O)—N($R^o$)—$R^o$, —C(S)—N($R^o$)—$R^o$, —S(O)$_2$—N(H)—$R^o$, —S(O)$_2$—N($R^o$)—$R^o$, —C(NH)—N(H)—$R^o$, —C(NH)—N($R^p$)—$R^c$, —N(H)—C(O)—$R^o$, —N(H)—C(S)—$R^o$, —N($R^o$)—C(O)—$R^o$, —N($R^o$)—C(S)—$R^o$, —N(H)—S(O)$_2$—$R^o$, —N($R^o$)—S(O)$_2$—$R^o$, —N(H)—C(O)—N(H)—$R^o$, —N(H)—C(S)—N(H)—$R^o$, —N($R^o$)—C(O)—$NH_2$, —N($R^o$)—C(S)—$NH_2$, —N($R^o$)—C(O)—N(H)—$R^o$, —N($R^o$)—C(S)—N(H)—$R^o$, —N(H)—C(O)—N($R^o$)—$R^o$, —N(H)—C(S)—N($R^o$)—$R^o$, —N($R^o$)—C(O)—N($R^o$)—$R^o$, —N($R^o$)—C(S)—N($R^o$)—$R^o$, —N(H)—S(O)$_2$—N(H)—$R^o$, —N($R^o$)—S(O)$_2$—$NH_2$, —N($R^o$)—S(O)$_2$—N(H)—$R^o$, —N(H)—S(O)$_2$—N($R^o$)—$R^o$, —N($R^o$)—S(O)$_2$—N($R^o$)—$R^o$, —N(H)—$R^o$, —N($R^o$)—$R^o$, —$R^c$, —$R^f$, and —$R^g$;

each $R^o$, $R^p$, and $R^c$ are independently selected from the group consisting of $R^d$, $R^e$, $R^f$, and $R^g$, or $R^p$ and $R^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, for example 1, 2, 3, 4 or 5, also 1, 2, or 3 substituents selected from the group consisting of halogen, —$NO_2$, —CN, —OH, —$NH_2$, —O—$R^u$, —S—$R^u$, —N(H)—$R^u$, —N($R^u$)—$R^u$, —$R^x$, and —$R^y$;

each $R^d$ is independently lower alkyl, wherein lower alkyl is optionally substituted with one or more, for example 1, 2, 3, 4 or 5, also 1, 2 or 3 substituents selected from the group consisting of fluoro, —OH, —$NH_2$, —$NO_2$, —CN, —C(O)—OH, —C(S)—OH, —C(O)—$NH_2$, —C(S)—$NH_2$, —S(O)$_2$—$NH_2$, —N(H)—C(O)—$NH_2$, —N(H)—C(S)—$NH_2$, —N(H)—S(O)$_2$—$NH_2$, —C(NH)—$NH_2$, —O—$R^k$, —S—$R^k$, —O—C(O)—$R^k$, —O—C(S)—$R^k$, —C(O)—$R^k$, —C(S)—$R^k$, —C(O)—O—$R^k$, —C(S)—O—$R^k$, —S(O)—$R^k$, —S(O)$_2$—$R^k$, —C(O)—N(H)—$R^k$, —C(S)—N(H)—$R^k$, —C(O)—N($R^k$)—$R^k$, —C(S)—N($R^k$)—$R^k$, —S(O)$_2$—N(H)—$R^k$, —S(O)$_2$—N($R^k$)—$R^k$, —C(NH)—N(H)—$R^k$, —C(NH)—N($R^m$)—$R^n$, —N(H)—C(O)—$R^k$, —N(H)—C(S)—$R^k$, —N($R^k$)—C(O)—$R^k$, —N($R^k$)—C(S)—$R^k$, —N(H)—S(O)$_2$—$R^k$, —N($R^k$)—S(O)$_2$—$R^k$, —N(H)—C(O)—N(H)—$R^k$, —N(H)—C(S)—N(H)—$R^k$, —N($R^k$)—C(O)—$NH_2$, —N($R^k$)—C(S)—$NH_2$, —N($R^k$)—C(O)—N(H)—$R^k$, —N($R^k$)—C(S)—N(H)—$R^k$, —N(H)—C(O)—N($R^k$)—$R^k$, —N(H)—C(S)—N($R^k$)—$R^k$, —N($R^k$)—C(O)—N($R^k$)—$R^k$, —N($R^k$)—C(S)—N($R^k$)—$R^k$, —N(H)—S(O)$_2$—N(H)—$R^k$, —N($R^k$)—S(O)$_2$—$NH_2$, —N($R^k$)—S(O)$_2$—N(H)—$R^k$, —N(H)—S(O)$_2$—N($R^k$)—$R^k$, —N($R^k$)—S(O)$_2$—N($R^k$)—$R^k$, —N(H)—$R^k$, —N($R^k$)—$R^k$, —$R^i$ and —$R^j$;

each $R^e$ is independently lower alkenyl, wherein lower alkenyl is optionally substituted with one or more, for example 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, and —R$^j$;

each $R^f$ is independently lower alkynyl, wherein lower alkynyl is optionally substituted with one or more, for example 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, and —R$^j$;

each $R^g$ is independently selected from the group consisting of cycloalkyl, heterocycloalkyl, aryl, and heteroaryl, wherein cycloalkyl, heterocycloalkyl, aryl, and heteroaryl are optionally substituted with one or more, for example 1, 2, 3, 4 or 5, also 1, 2 or 3 substituents selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, —R$^i$ and —R$^j$;

$R^k$, $R^m$, and $R^n$ are each independently selected from the group consisting of $R^h$, $R^i$, and $R^j$, or $R^m$ and $R^n$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, for example 1, 2, 3, 4 or 5, also 1, 2, or 3 substituents selected from the group consisting of halogen, —NO$_2$, —CN, —OH, —NH$_2$, —O—R$^u$, —S—R$^u$, —N(H)—R$^u$, —NR$^u$R$^u$, —R$^x$, and —R$^y$;

each $R^h$ is independently lower alkyl optionally substituted with one or more, for example 1, 2, 3, 4 or 5, also 1, 2, or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R$^r$)—R$^r$, —S(O)$_2$—N(H)—R$^r$, —S(O)$_2$—N(R$^r$)—R$^r$, —C(NH)—N(H)—R$^r$, —C(NH)—N(R$^s$)—R$^t$, —N(H)—C(O)—R$^r$, —N(H)—C(S)—R$^r$, —N(R$^r$)—C(O)—R$^r$, —N(R$^r$)—C(S)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)$_2$—N(H)—R$^r$, —N(R$^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(H)—R$^r$, —N(R$^r$)—R$^r$, —R$^i$ and —R$^j$;

each $R^i$ is independently selected from the group consisting of lower alkenyl and lower alkynyl, wherein lower alkenyl or lower alkynyl are optionally substituted with one or more, for example 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—

$NH_2$, —C(NH)—$NH_2$, —O—$R^r$, —S—$R^r$, —O—C(O)—$R^r$, —O—C(S)—$R^r$, —C(O)—$R^r$, —C(S)—$R^r$, —C(O)—O—$R^r$, —C(S)—O—$R^r$, —S(O)—$R^r$, —S(O)$_2$—$R^r$, —C(O)—N(H)—$R^r$, —C(S)—N(H)—$R^r$, —C(O)—N($R'$)—$R^r$, —C(S)—N($R'$)—$R^r$, —S(O)$_2$—N(H)—$R^r$, —S(O)$_2$—N($R'$)—$R^r$, —C(NH)—N(H)—$R^r$, —C(NH)—N($R^s$)—$R^t$, —N(H)—C(O)—$R^r$, —N(H)—C(S)—$R^r$, —N($R'$)—C(O)—$R^r$, —N($R'$)—C(S)—$R^r$, —N(H)—S(O)$_2$—$R^r$, —N($R'$)—S(O)$_2$—$R^r$, —N(H)—C(O)—N(H)—$R^r$, —N(H)—C(S)—N(H)—$R^r$, —N($R'$)—C(O)—$NH_2$, —N($R'$)—C(S)—$NH_2$, —N($R'$)—C(O)—N(H)—$R^r$, —N($R'$)—C(S)—N(H)—$R^r$, —N(H)—C(O)—N($R'$)—$R^r$, —N(H)—C(S)—N($R'$)—$R^r$, —N($R'$)—C(O)—N($R'$)—$R^r$, —N($R'$)—C(S)—N($R'$)—$R^r$, —N(H)—S(O)$_2$—N(H)—$R^r$, —N($R'$)—S(O)$_2$—$NH_2$, —N($R'$)—S(O)$_2$—N(H)—$R^r$, —N(H)—S(O)$_2$—N($R'$)—$R^r$, —N($R'$)—S(O)$_2$—N($R'$)—$R^r$, —N(H)—$R^r$, —N($R'$)—$R^r$, and —$R^j$;

each $R^j$ is independently selected from the group consisting of cycloalkyl, heterocycloalkyl, aryl, and heteroaryl, wherein cycloalkyl, heterocycloalkyl, aryl, and heteroaryl are optionally substituted with one or more, for example 1, 2, 3, 4 or 5, also 1, 2 or 3 substituents selected from the group consisting of halogen, —OH, —$NH_2$, —$NO_2$, —CN, —C(O)—OH, —C(S)—OH, —C(O)—$NH_2$, —C(S)—$NH_2$, —S(O)$_2$—$NH_2$, —N(H)—C(O)—$NH_2$, —N(H)—C(S)—$NH_2$, —N(H)—S(O)$_2$—$NH_2$, —C(NH)—$NH_2$, —O—$R^r$, —S—$R^r$, —O—C(O)—$R^r$, —O—C(S)—$R^r$, —C(O)—$R^r$, —C(S)—$R^r$, —C(O)—O—$R^r$, —C(S)—O—$R^r$, —S(O)—$R^r$, —S(O)$_2$—$R^r$, —C(O)—N(H)—$R^r$, —C(S)—N(H)—$R^r$, —C(O)—N($R'$)—$R^r$, —C(S)—N($R'$)—$R^r$, —S(O)$_2$—N(H)—$R^r$, —S(O)$_2$—N($R'$)—$R^r$, —C(NH)—N(H)—$R^r$, —C(NH)—N($R^s$)—$R^t$, —N(H)—C(O)—$R^r$, —N(H)—C(S)—$R^r$, —N($R'$)—C(O)—$R^r$, —N($R'$)—C(S)—$R^r$, —N(H)—S(O)$_2$—$R^r$, —N($R'$)—S(O)$_2$—$R^r$, —N(H)—C(O)—N(H)—$R^r$, —N(H)—C(S)—N(H)—$R^r$, —N($R'$)—C(O)—$NH_2$, —N($R'$)—C(S)—$NH_2$, —N($R'$)—C(O)—N(H)—$R^r$, —N($R'$)—C(S)—N(H)—$R^r$, —N(H)—C(O)—N($R'$)—$R^r$, —N(H)—C(S)—N($R'$)—$R^r$, —N($R'$)—C(O)—N($R'$)—$R^r$, —N($R'$)—C(S)—N($R'$)—$R^r$, —N(H)—S(O)$_2$—N(H)—$R^r$, —N($R'$)—S(O)$_2$—$NH_2$, —N($R'$)—S(O)$_2$—N(H)—$R^r$, —N(H)—S(O)$_2$—N($R'$)—$R^r$, —N($R'$)—S(O)$_2$—N($R'$)—$R^r$, —N($R'$)—$R^r$, cycloalkylamino, and —$R^x$;

each $R^r$, $R^s$, and $R^t$ at each occurrence are independently selected from the group consisting of lower alkyl, $C_{3-6}$ alkenyl, $C_{3-6}$ alkynyl, cycloalkyl, heterocycloalkyl, aryl and heteroaryl, wherein lower alkyl is optionally substituted with one or more, for example 1, 2, 3, 4 or 5, also 1, 2, or 3 substituents selected from the group consisting of —$R^y$, fluoro, —OH, —$NH_2$, lower alkoxy, fluoro substituted lower alkoxy, lower alkylthio, fluoro substituted lower alkylthio, mono-alkylamino, di-alkylamino, and cycloalkylamino, and wherein $C_{3-6}$ alkenyl or $C_{3-6}$ alkynyl are optionally substituted with one or more, for example 1, 2, 3, 4 or 5, also 1, 2, or 3 substituents selected from the group consisting of —$R^y$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more, for example 1, 2, 3, 4 or 5, also 1, 2, or 3 substituents selected from the group consisting of halogen, —OH, —$NH_2$, —$NO_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, or $R^s$ and $R^t$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, for example 1, 2, 3, 4 or 5, also 1, 2, or 3 substituents selected from the group consisting of halogen, —$NO_2$, —CN, —OH, —$NH_2$, —O—$R^u$, —S—$R^u$, —N(H)—$R^u$, —N($R^u$)—$R^u$, —$R^x$, and —$R^y$;

each $R^u$ is independently selected from the group consisting of lower alkyl, $C_{3-6}$ alkenyl, $C_{3-6}$ alkynyl, cycloalkyl, heterocycloalkyl, aryl, and heteroaryl, wherein lower alkyl is optionally substituted with one or more, for example 1, 2, 3, 4 or 5, also 1, 2, or 3 substituents selected from the group consisting of —$R^y$, fluoro, —OH, —$NH_2$, lower alkoxy, fluoro substituted lower alkoxy, lower alkylthio, fluoro substituted lower alkylthio, mono-alkylamino, di-alkylamino, and cycloalkylamino, and wherein $C_{3-6}$ alkenyl or $C_{3-6}$ alkynyl are optionally substituted with one or more, for example 1, 2, 3, 4 or 5, also 1, 2, or 3 substituents selected from the group consisting of —$R^y$, fluoro, —OH, —$NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more, for example 1, 2, 3, 4 or 5, also 1, 2, or 3 substituents selected from the group consisting of halogen, —OH, —$NH_2$, —$NO_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

each $R^x$ is selected from the group consisting of lower alkyl, lower alkenyl and lower alkynyl, wherein lower alkyl is optionally substituted with one or more, for example 1, 2, 3, 4 or 5, also 1, 2, or 3 substituents selected from the group consisting of —$R^y$, fluoro, —OH, —$NH_2$, lower alkoxy, fluoro substituted lower alkoxy, lower alkylthio, fluoro substituted lower alkylthio, mono-alkylamino, di-alkylamino, and cycloalkylamino, and wherein lower alkenyl or lower alkynyl are optionally substituted with one or more, for example 1, 2, 3, 4 or 5, also 1, 2, or 3 substituents selected from the group consisting of —$R^y$, fluoro, —OH, —$NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; and each $R^y$ is selected from the group consisting of cycloalkyl, heterocycloalkyl, aryl, and heteroaryl, wherein cycloalkyl, heterocycloalkyl, aryl, and heteroaryl are optionally substituted with one or more, for example 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

Provided herein are compounds of Formula I:

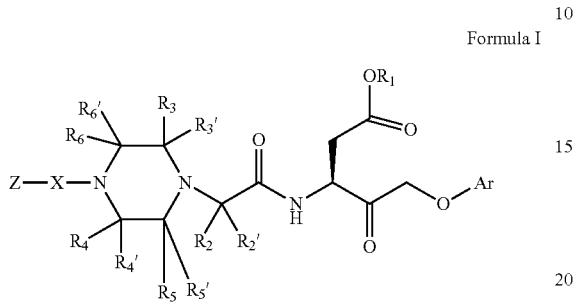

Formula I or pharmaceutically acceptable salts, solvates, tautomers or isomers thereof, wherein:

Z is aryl, arylalkyl, heteroaryl or heteroarylalkyl, each of which is optionally substituted;

Ar is phenyl, phenylalkyl, naphthyl, naphthylalkyl or heteroaryl, each of which is optionally substituted;

X is a bond, SO$_2$, SO or optionally substituted lower alkylene;

R$_1$ is hydrogen, lower alkyl, cycloalkyl, (cycloalkyl)alkyl or optionally substituted phenylalkyl;

R$_2$ and R$_{2'}$ are selected as follows:
  i) R$_2$ and R$_{2'}$ are each independently hydrogen, fluoro, —OH, —NH$_2$, lower alkyl, lower alkoxy, lower alklylthio, mono-alkylamino or di-alkylamino, wherein the alkyl chain(s) of lower alkyl, lower alkoxy, lower alkylthio, mono-alkylamino, or di-alkylamino are optionally substituted with one or more substituents selected from the group consisting of halogen, —OH, —NH$_2$, lower alkoxy, halogen substituted lower alkoxy, lower alkylthio, halogen substituted lower alkylthio, mono-alkylamino, di-alkylamino, and cycloalkylamino;
  ii) R$_2$ and R$_{2'}$ combine with the carbon to which they are attached to form a 3-7 membered monocyclic cycloalkyl or 5-7 membered monocyclic heterocycloalkyl, wherein the monocyclic cycloalkyl or monocyclic heterocycloalkyl are optionally substituted with one or more substituents selected from the group consisting of halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

R$_3$, R$_{3'}$, R$_4$, R$_{4'}$, R$_5$, R$_{5'}$, R$_6$ and R$_{6'}$ are selected as follows:
  i) R$_3$, R$_{3'}$, R$_4$, R$_{4'}$, R$_5$, R$_{5'}$, R$_6$ and R$_{6'}$ are each independently hydrogen, optionally substituted lower alkyl, optionally substituted C$_{2-6}$ alkenyl, optionally substituted C$_{2-6}$ alkynyl, optionally substituted aryl, optionally substituted heteroaryl, optionally substituted arylalkyl or optionally substituted heteroarylalkyl;
  ii) R$_3$, R$_{3'}$ and R$_6$, R$_{6'}$ together form an optionally substituted aryl, optionally substituted heteroaryl ring, and R$_4$, R$_{4'}$, R$_5$ and R$_{5'}$ are each independently hydrogen, optionally substituted lower alkyl, optionally substituted C$_{2-6}$ alkenyl, optionally substituted C$_{2-6}$ alkynyl, optionally substituted aryl, optionally substituted heteroaryl, optionally substituted arylalkyl or optionally substituted heteroarylalkyl;
  iii) R$_4$, R$_{4'}$ and R$_5$, R$_{5'}$ together form an optionally substituted aryl or optionally substituted heteroaryl ring, and R$_3$, R$_{3'}$, R$_6$ and R$_{6'}$ are each independently hydrogen, optionally substituted lower alkyl, optionally substituted C$_{2-6}$ alkenyl, optionally substituted C$_{2-6}$ alkynyl, optionally substituted aryl, optionally substituted heteroaryl, optionally substituted arylalkyl or optionally substituted heteroarylalkyl, with the proviso that when R$_3$, R$_{3'}$ and R$_6$, R$_{6'}$ together form an aryl, substituted aryl, heteroaryl or substituted heteroaryl ring, R$_4$, R$_{4'}$ and R$_5$, R$_{5'}$ cannot together form an aryl, substituted aryl, heteroaryl or substituted heteroaryl ring and when R$_4$, R$_{4'}$ and R$_5$, R$_{5'}$ together form an aryl, substituted aryl, heteroaryl or substituted heteroaryl ring, R$_3$, R$_{3'}$ and R$_6$, R$_{6'}$ cannot together form an aryl, substituted aryl, heteroaryl or substituted heteroaryl ring; or iv) R$_3$ and R$_{3'}$ together, R$_4$ and R$_{4'}$ together, R$_5$ and R$_{5'}$ together or R$_6$ and R$_{6'}$ together is oxo (i.e., =O), and all substituents for R$_3$, R$_{3'}$, R$_4$, R$_{4'}$, R$_5$, R$_{5'}$, R$_6$ and R$_{6'}$ other than the oxo being as defined in i), ii) and iii) above, with the proviso that:

when R$_3$ and R$_{3'}$ together is oxo, none or one of R$_4$ and R$_{4'}$ together, R$_5$ and R$_{5'}$ together and R$_6$ and R$_{6'}$ together is oxo, when R$_4$ and R$_{4'}$ together is oxo, none or one of R$_3$ and R$_{3'}$ together, R$_5$ and R$_{5'}$ together and R$_6$ and R$_{6'}$ together is oxo, when R$_5$ and R$_{5'}$ together is oxo, none or one of R$_3$ and R$_{3'}$ together, R$_4$ and R$_{4'}$ together and R$_6$ and R$_{6'}$ together is oxo, and when R$_6$ and R$_{6'}$ together is oxo, none or one of R$_3$ and R$_{3'}$ together, R$_4$ and R$_{4'}$ together and R$_5$ and R$_{5'}$ together is oxo, wherein, unless specified otherwise, the substituents on cycloalkyl, aryl, heterocycloalkyl, and heteroaryl groups, when present are selected from one or more, in one embodiment, 1 to 5, in one embodiment, 1 to 4, or in one embodiment, 1 to 3, substituents Q$^1$, wherein each Q$^1$ is independently selected from halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^P$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—

S(O)$_2$—N(R$^o$)—R$^o$, —N(H)—R$^o$, —N(R$^o$)—R$^o$, —R$^d$, —R$^e$, —R$^f$, and —R$^g$;

unless specified otherwise, the substituents on alkyl, alkenyl and alkynyl groups, when present are selected from one or more, in one embodiment, 1 to 5, in one embodiment, 1 to 4, or in one embodiment, 1 to 3, substituents Q$^2$, wherein each Q$^2$ is independently selected from —F, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH), —NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^c$, —R$^f$, and —R$^g$;

each R$^o$, R$^p$, and R$^c$ are independently selected from the group consisting of R$^d$, R$^e$, R$^f$, and R$^g$, or R$^p$ and R$^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, for example 1, 2, 3, 4 or 5, also 1, 2, or 3 substituents selected from the group consisting of halogen, —NO$_2$, —CN, —OH, —NH$_2$, —O—R$^u$, —S—R$^u$, —N(H)—R$^u$, —N(R$^u$)—R$^u$, —R$^x$, and —R$^y$;

each R$^d$ is independently lower alkyl, wherein lower alkyl is optionally substituted with one or more, for example 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^i$ and —R$^j$;

each R$^e$ is independently lower alkenyl, wherein lower alkenyl is optionally substituted with one or more, for example 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, and —R$^j$;

each R$^f$ is independently lower alkynyl, wherein lower alkynyl is optionally substituted with one or more, for example 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, and —R$^j$;

each R$^g$ is independently selected from the group consisting of cycloalkyl, heterocycloalkyl, aryl, and heteroaryl, wherein cycloalkyl, heterocycloalkyl, aryl, and heteroaryl are optionally substituted with one or more, for example 1, 2, 3, 4 or 5, also 1, 2 or 3 substituents selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, —R$^i$ and —R$^j$;

R$^k$, R$^m$, and R$^n$ are each independently selected from the group consisting of R$^h$, R$^i$, and R$^j$, or R$^m$ and R$^n$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, for example 1, 2, 3, 4 or 5, also 1, 2, or 3 substituents selected from the group consisting of halogen, —NO$_2$, —CN, —OH, —NH$_2$, —O—R$^u$, —S—R$^u$, —N(H)—R$^u$, —NR$^u$R$^u$, —R$^x$, and —R$^y$;

each R$^h$ is independently lower alkyl optionally substituted with one or more, for example 1, 2, 3, 4 or 5, also 1, 2, or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R$^r$)—R$^r$, —S(O)$_2$—N(H)—R$^r$, —S(O)$_2$—N(R$^r$)—R$^r$, —C(NH)—N(H)—R$^r$, —C(NH)—N(R$^s$)—R$^t$, —N(H)—C(O)—R$^r$, —N(H)—C(S)—R$^r$, —N(R$^r$)—C(O)—R$^r$, —N(R$^r$)—C(S)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)$_2$—N(H)—R$^r$, —N(R$^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(H)—R$^r$, —N(R$^r$)—R$^r$, —R$^i$ and —R$^j$;

each R$^i$ is independently selected from the group consisting of lower alkenyl and lower alkynyl, wherein lower alkenyl or lower alkynyl are optionally substituted with one or more, for example 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—S(O)$_2$—NH$_2$, —C(NH)—NH$_2$, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R$^r$)—R$^r$, —S(O)$_2$—N(H)—R$^r$, —S(O)$_2$—N(R$^r$)—R$^r$, —C(NH)—N(H)—R$^r$, —C(NH)—N(R$^s$)—R$^t$, —N(H)—C(O)—R$^r$, —N(H)—C(S)—R$^r$, —N(R$^r$)—C(O)—R$^r$, —N(R$^r$)—C(S)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^r$, —N(R$^r$)—C(S)—N(H)—R$^r$, —N(H)—C(O)—N(R$^1$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)$_2$—N(H)—R$^r$, —N(R$^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(H)—R$^r$, —N(R$^r$)—R$^r$, and —R$^j$;

each R$^j$ is independently selected from the group consisting of cycloalkyl, heterocycloalkyl, aryl, and heteroaryl, wherein cycloalkyl, heterocycloalkyl, aryl, and heteroaryl are optionally substituted with one or more, for example 1, 2, 3, 4 or 5, also 1, 2 or 3 substituents selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R$^r$)—R$^r$, —S(O)$_2$—N(H)—R$^r$, —S(O)$_2$—N(R$^r$)—R$^r$, —C(NH)—N(H)—R$^r$, —C(NH)—N(R$^s$)—R$^t$, —N(H)—C(O)—R$^r$, —N(H)—C(S)—R$^r$, —N(R$^r$)—C(O)—R$^r$, —N(R$^r$)—C(S)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)$_2$—N(H)—R$^r$, —N(R$^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(R$^r$)—R$^r$, cycloalkylamino, and —R$^x$;

each R$^r$, R$^s$, and R$^t$ at each occurrence are independently selected from the group consisting of lower alkyl, C$_{3-6}$ alkenyl, C$_{3-6}$alkynyl, cycloalkyl, heterocycloalkyl, aryl and heteroaryl, wherein lower alkyl is optionally substituted with one or more, for example 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein C$_{3-6}$ alkenyl or C$_{3-6}$ alkynyl are optionally substituted with one or more, for example 1, 2, 3, 4 or 5, also 1, 2, or 3 substituents selected from the group consisting of —R$^y$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more, for example 1, 2, 3, 4 or 5, also 1, 2, or 3 substituents selected from the group consisting of halogen, —OH, —$NH_2$, —$NO_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, or $R^s$ and $R^t$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, for example 1, 2, 3, 4 or 5, also 1, 2, or 3 substituents selected from the group consisting of halogen, —$NO_2$, —CN, —OH, —$NH_2$, —O—$R^u$, —S—$R^u$, —N(H)—$R^u$, —N($R^u$)—$R^u$, —$R^x$, and —$R^y$;

each $R^u$ is independently selected from the group consisting of lower alkyl, $C_{3-6}$ alkenyl, $C_{3-6}$ alkynyl, cycloalkyl, heterocycloalkyl, aryl, and heteroaryl, wherein lower alkyl is optionally substituted with one or more, for example 1, 2, 3, 4 or 5, also 1, 2, or 3 substituents selected from the group consisting of —$R^y$, fluoro, —OH, —$NH_2$, lower alkoxy, fluoro substituted lower alkoxy, lower alkylthio, fluoro substituted lower alkylthio, mono-alkylamino, di-alkylamino, and cycloalkylamino, and wherein $C_{3-6}$ alkenyl or $C_{3-6}$ alkynyl are optionally substituted with one or more, for example 1, 2, 3, 4 or 5, also 1, 2, or 3 substituents selected from the group consisting of —$R^y$, fluoro, —OH, —$NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more, for example 1, 2, 3, 4 or 5, also 1, 2, or 3 substituents selected from the group consisting of halogen, —OH, —$NH_2$, —$NO_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

each $R^x$ is selected from the group consisting of lower alkyl, lower alkenyl and lower alkynyl, wherein lower alkyl is optionally substituted with one or more, for example 1, 2, 3, 4 or 5, also 1, 2, or 3 substituents selected from the group consisting of —$R^y$, fluoro, —OH, —$NH_2$, lower alkoxy, fluoro substituted lower alkoxy, lower alkylthio, fluoro substituted lower alkylthio, mono-alkylamino, di-alkylamino, and cycloalkylamino, and wherein lower alkenyl or lower alkynyl are optionally substituted with one or more, for example 1, 2, 3, 4 or 5, also 1, 2, or 3 substituents selected from the group consisting of —$R^y$, fluoro, —OH, —$NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; and each $R^y$ is selected from the group consisting of cycloalkyl, heterocycloalkyl, aryl, and heteroaryl, wherein cycloalkyl, heterocycloalkyl, aryl, and heteroaryl are optionally substituted with one or more, for example 1, 2, 3, 4 or 5, also 1, 2, or 3 substituents selected from the group consisting of halogen, —OH, —$NH_2$, —$NO_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

In one embodiment, provided herein is a compound of Formula I or pharmaceutically acceptable salts, solvates, tautomers or isomers thereof, wherein:

Z is aryl, substituted aryl, phenyl, substituted phenyl, phenylalkyl, substituted phenylalkyl, naphthyl, substituted naphthyl, (1 or 2-naphthyl)alkyl, heteroaryl or (heteroaryl)alkyl;

Ar is phenyl, substituted phenyl, phenylalkyl, substituted phenylalkyl, naphthyl, substituted naphthyl (1 or 2-naphthyl)alkyl, heteroaryl or optionally substituted heteroaryl;

X is a bond, $SO_2$, SO, CO, or optionally substituted lower alkylene;

$R_1$ is hydrogen, lower alkyl, cycloalkyl, (cycloalkyl)alkyl, phenylalkyl or substituted phenylalkyl;

$R_2$ and $R_{2'}$ are independently hydrogen, fluoro, —OH, —$NH_2$, lower alkyl, lower alkoxy, lower alklylthio, mono-alkylamino or di-alkylamino, wherein the alkyl chain(s) of lower alkyl, lower alkoxy, lower alkylthio, mono-alkylamino, or di-alkylamino are optionally substituted with one or more substituents selected from the group consisting of halogen, —OH, —$NH_2$, lower alkoxy, halogen substituted lower alkoxy, lower alkylthio, halogen substituted lower alkylthio, mono-alkylamino, di-alkylamino, and cycloalkylamino; or $R_2$ and $R_{2'}$ combine with the carbon to which they are attached to form a 3-7 membered monocyclic cycloalkyl or 5-7 membered monocyclic heterocycloalkyl, wherein the monocyclic cycloalkyl or monocyclic heterocycloalkyl are optionally substituted with one or more substituents selected from the group consisting of halogen, —OH, —$NH_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

$R_3$, $R_{3'}$, $R_4$, $R_{4'}$, $R_5$, $R_{5'}$, $R_6$ and $R_{6'}$ are each independently hydrogen, optionally substituted lower alkyl, optionally substituted $C_{2-6}$ alkenyl, optionally substituted $C_{2-6}$ alkynyl, optionally substituted aryl, optionally substituted heteroaryl, optionally substituted arylalkyl or optionally substituted heteroaryl alkyl; or $R_3$, $R_{3'}$ and $R_6$, $R_{6'}$ together form an aryl, substituted aryl, heteroaryl or substituted heteroaryl ring, substituents for $R_4$, $R_{4'}$, $R_5$ and $R_{5'}$ being as defined above, or $R_4$, $R_{4'}$ and $R_5$, $R_{5'}$ together form an aryl, substituted aryl, heteroaryl or substituted heteroaryl ring, substituents for $R_3$, $R_{3'}$, $R_6$ and $R_{6'}$ being as defined above, with the proviso that when $R_3$, $R_{3'}$ and $R_6$, $R_{6'}$ together form an aryl, substituted aryl, heteroaryl or substituted heteroaryl ring, $R_4$, $R_{4'}$ and $R_5$, $R_{5'}$ cannot together form an aryl, substituted aryl, heteroaryl or substituted heteroaryl ring and when $R_4$, $R_{4'}$ and $R_5$, $R_{5'}$ together form an aryl, substituted aryl, heteroaryl or substituted heteroaryl ring, $R_3$, $R_{3'}$ and $R_6$, $R_{6'}$ cannot together form an aryl, substituted aryl, heteroaryl or substituted heteroaryl ring; or $R_3$ and $R_{3'}$ together, $R_4$ and $R_{4'}$ together, $R_5$ and $R_{5'}$ together or $R_6$ and $R_{6'}$ together is oxo (i.e., =O), all substituents for $R_3$, $R_{3'}$, $R_4$, $R_{4'}$, $R_5$, $R_{5'}$, $R_6$ and $R_{6'}$ other than the oxo being as defined in the above two paragraphs, with the proviso that:

when $R_3$ and $R_{3'}$ together is oxo, none or one of $R_4$ and $R_{4'}$ together, $R_5$ and $R_{5'}$ together and $R_6$ and $R_{6'}$ together is oxo, when $R_4$ and $R_{4'}$ together is oxo, none or one of $R_3$ and $R_{3'}$ together, $R_5$ and $R_{5'}$ together and $R_6$ and $R_{6'}$ together is oxo, when $R_5$ and $R_{5'}$ together is oxo, none or one of $R_3$ and $R_{3'}$ together, $R_4$ and $R_{4'}$ together and $R_6$ and $R_{6'}$ together is oxo, and when $R_6$ and $R_{6'}$ together is oxo, none or one of $R_3$ and $R_{3'}$ together, $R_4$ and $R_{4'}$ together and $R_5$ and $R_{5'}$ together is oxo.

In one embodiment, provided herein is a compound of Formula I or pharmaceutically acceptable salts, solvates, tautomers or isomers thereof, wherein:

Z is aryl, substituted aryl, phenyl, substituted phenyl, phenylalkyl, substituted phenylalkyl, naphthyl, substituted naphthyl, (1 or 2-naphthyl)alkyl, heteroaryl or (heteroaryl)alkyl;

Ar is phenyl, substituted phenyl, phenylalkyl, substituted phenylalkyl, naphthyl, substituted naphthyl (1 or 2-naphthyl)alkyl, heteroaryl or optionally substituted heteroaryl;

X is a bond, $SO_2$, SO, or optionally substituted lower alkylene;

$R_1$ is hydrogen, lower alkyl, cycloalkyl, (cycloalkyl)alkyl, phenylalkyl or substituted phenylalkyl;

$R_2$ and $R_{2'}$ are independently hydrogen, fluoro, —OH, —$NH_2$, lower alkyl, lower alkoxy, lower alklylthio, mono-alkylamino or di-alkylamino, wherein the alkyl chain(s) of lower alkyl, lower alkoxy, lower alkylthio, mono-alkylamino, or di-alkylamino are optionally substituted with one or more substituents selected from the group consisting of halogen, —OH, —$NH_2$, lower alkoxy, halogen substituted lower alkoxy, lower alkylthio, halogen substituted lower alkylthio, mono-alkylamino, di-alkylamino, and cycloalkylamino; or $R_2$ and $R_{2'}$ combine with the carbon to which they are attached to form a 3-7 membered monocyclic cycloalkyl or 5-7 membered monocyclic heterocycloalkyl, wherein the monocyclic cycloalkyl or monocyclic heterocycloalkyl are optionally substituted with one or more substituents selected from the group consisting of halogen, —OH, —$NH_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

$R_3$, $R_{3'}$, $R_4$, $R_{4'}$, $R_5$, $R_{5'}$, $R_6$ and $R_{6'}$ are each independently hydrogen, optionally substituted lower alkyl, optionally substituted $C_{2-6}$ alkenyl, optionally substituted $C_{2-6}$ alkynyl, optionally substituted aryl, optionally substituted heteroaryl, optionally substituted arylalkyl or optionally substituted heteroaryl alkyl; or $R_3$, $R_{3'}$ and $R_6$, $R_{6'}$ together form an aryl, substituted aryl, heteroaryl or substituted heteroaryl ring, substituents for $R_4$, $R_{4'}$, $R_5$ and $R_{5'}$ being as defined above, or $R_4$, $R_{4'}$ and $R_5$, $R_{5'}$ together form an aryl, substituted aryl, heteroaryl or substituted heteroaryl ring, substituents for $R_3$, $R_{3'}$, $R_6$ and $R_{6'}$ being as defined above, with the proviso that when $R_3$, $R_{3'}$ and $R_6$, $R_{6'}$ together form an aryl, substituted aryl, heteroaryl or substituted heteroaryl ring, $R_4$, $R_{4'}$ and $R_5$, $R_{5'}$ cannot together form an aryl, substituted aryl, heteroaryl or substituted heteroaryl ring and when $R_4$, $R_{4'}$ and $R_5$, $R_{5'}$ together form an aryl, substituted aryl, heteroaryl or substituted heteroaryl ring, $R_3$, $R_{3'}$ and $R_6$, $R_{6'}$ cannot together form an aryl, substituted aryl, heteroaryl or substituted heteroaryl ring; or $R_3$ and $R_{3'}$ together, $R_4$ and $R_{4'}$ together, $R_5$ and $R_{5'}$ together or $R_6$ and $R_{6'}$ together is oxo (i.e., =O), all substituents for $R_3$, $R_{3'}$, $R_4$, $R_{4'}$, $R_5$, $R_{5'}$, $R_6$ and $R_{6'}$ other than the oxo being as defined in the above two paragraphs, with the proviso that:

when $R_3$ and $R_{3'}$ together is oxo, none or one of $R_4$ and $R_{4'}$ together, $R_5$ and $R_{5'}$ together and $R_6$ and $R_{6'}$ together is oxo, when $R_4$ and $R_{4'}$ together is oxo, none or one of $R_3$ and $R_{3'}$ together, $R_5$ and $R_{5'}$ together and $R_6$ and $R_{6'}$ together is oxo, when $R_5$ and $R_{5'}$ together is oxo, none or one of $R_3$ and $R_{3'}$ together, $R_4$ and $R_{4'}$ together and $R_6$ and $R_{6'}$ together is oxo, and when $R_6$ and $R_{6'}$ together is oxo, none or one of $R_3$ and $R_{3'}$ together, $R_4$ and $R_{4'}$ together and $R_5$ and $R_{5'}$ together is oxo.

The compounds of Formula I also can exist as pharmaceutically acceptable salts, solvates, tautomers, isomers and hydrates. Thus, these compounds can crystallize with, for example, waters of hydration, or one, a number of, or any fraction thereof of molecules of the mother liquor solvent. The salts, solvates, tautomers, isomers and hydrates of such compounds are included within the scope of the compounds provided herein, including, the compounds of Formula I, and those of the sub-genuses and related formulae as described below.

In some embodiments, the compound of Formula I has the sub-generic structure of Formula Ia

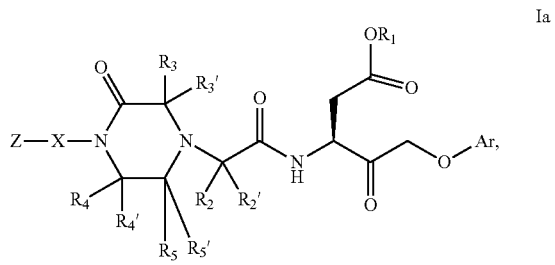

or pharmaceutically acceptable salts, solvates, tautomers and isomers thereof, wherein Ar, Z, X, $R_1$, $R_2$, $R_{2'}$, $R_3$, $R_{3'}$, $R_4$, $R_{4'}$, $R_5$ and $R_{5'}$ are as defined for Formula I.

In some embodiments of the compounds of Formula Ia, $R_3$, $R_{3'}$, $R_4$, $R_{4'}$, $R_5$ and $R_{5'}$ are each independently hydrogen or optionally substituted lower alkyl. In other embodiments of the compounds of Formula Ia, $R_3$, $R_{3'}$, $R_4$, $R_{4'}$, $R_5$ and $R_{5'}$ are each hydrogen. In some embodiments of the compounds of Formula Ia, $R_3$ and $R_{3'}$ together are oxo. In other embodiments of the compounds of Formula Ia, $R_5$ and $R_{5'}$ together are oxo.

In some embodiments, the compound of Formula I has the sub-generic structure of Formula Ib,

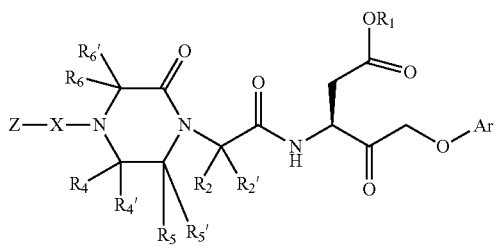

Ib or pharmaceutically acceptable salts, solvates, tautomers and isomers thereof, wherein Ar, Z, X, $R_1$, $R_2$, $R_{2'}$, $R_4$, $R_{4'}$, $R_5$, $R_{5'}$, $R_6$ and $R_{6'}$ are as defined for Formula I.

In some embodiments of the compounds of Formula Ib or pharmaceutically acceptable salts, solvates, tautomers and isomers thereof, $R_4$, $R_{4'}$, $R_5$, $R_{5'}$, $R_6$ and $R_{6'}$ are each independently hydrogen or optionally substituted lower alkyl. In further embodiments of the compounds of Formula Ib, $R_4$, $R_{4'}$, $R_5$, $R_{5'}$, $R_6$ and $R_{6'}$ are each hydrogen. In some embodiments of the compounds of Formula Ib, $R_6$ and $R_{6'}$ together are oxo. In other embodiments of the compounds of Formula Ib, $R_4$ and $R_{4'}$ together are oxo.

In some embodiments, the compound of Formula I has the sub-generic structure of Formula Ic,

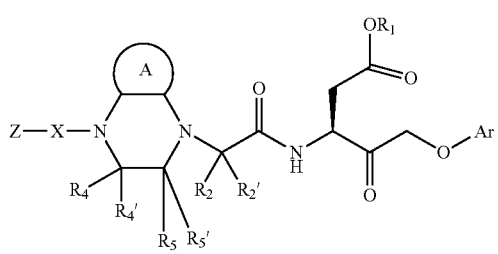

Ic or pharmaceutically acceptable salts, solvates, tautomers and isomers thereof, wherein Ar, Z, X, $R_1$, $R_2$, $R_{2'}$, $R_4$, $R_{4'}$, $R_5$ are as defined for Formula I, and ring A is aryl or heteroaryl, each of which is optionally substituted with 1 to 3 substituents $Q^1$. In certain embodiments, in the compounds of Formula Ic provided herein, ring A is a benzene ring optionally substituted with 1 to 3 substituents $Q^1$.

In some embodiments, the compound of Formula I has the sub-generic structure of Formula Id,

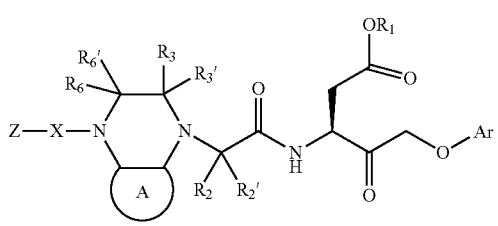

Id or pharmaceutically acceptable salts, solvates, tautomers and isomers thereof, wherein Ar, Z, X, $R_1$, $R_2$, $R_{2'}$, $R_3$, $R_{3'}$, $R_6$ and $R_{6'}$ are as defined for Formula I, and ring A is aryl or heteroaryl, each of which is optionally substituted with 1 to 3 substituents $Q^1$. In certain embodiments, in the compounds of Formula Id provided herein, ring A is a benzene ring optionally substituted with 1 to 3 substituents $Q^1$.

In certain embodiments, the compounds provided herein have the structure of Formula I, Formula Ia, Formula Ib, Formula Ic or Formula Id, wherein X is a bond, and remaining variables are as described elsewhere herein.

In certain embodiments, the compounds provided herein have the structure of Formula I, Formula Ia, Formula Ib, Formula Ic or Formula Id, wherein X is lower alkylene, and remaining variables are as described elsewhere herein.

In certain embodiments, the compounds provided herein have the structure of Formula I, Formula Ia, Formula Ib, Formula Ic or Formula Id, wherein X is methylene, and remaining variables are as described elsewhere herein.

In certain embodiments, the compounds provided herein have the structure of Formula I, Formula Ia, Formula Ib, Formula Ic or Formula Id, wherein X is $SO_2$, and remaining variables are as described elsewhere herein.

In certain embodiments, the compounds provided herein have the structure of Formula I, Formula Ia, Formula Ib, Formula Ic or Formula Id, wherein X is CO, and remaining variables are as described elsewhere herein.

In further embodiments, the compounds provided herein have the structure of Formula II-1

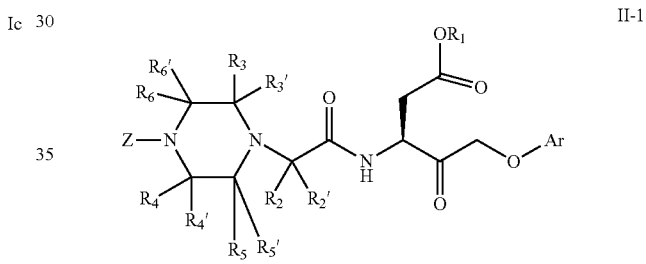

II-1 or pharmaceutically acceptable salts, solvates, tautomers and isomers thereof, wherein Ar, Z, Ra, $R_2$, $R_{2'}$, $R_3$, $R_{3'}$, $R_4$, $R_{4'}$, $R_5$, $R_{5'}$, $R_6$ and $R_{6'}$ are as defined elsewhere herein.

In further embodiments, the compounds provided herein have the structure of Formula IIa-1

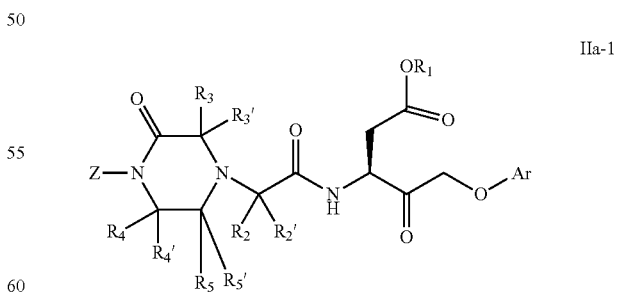

IIa-1 or pharmaceutically acceptable salts, solvates, tautomers and isomers thereof, wherein Ar, Z, $R_1$, $R_2$, $R_{2'}$, $R_3$, $R_{3'}$, $R_4$, $R_{4'}$, $R_5$, and $R_{5'}$ are as defined elsewhere herein.

In further embodiments, the compounds provided herein have the structure of Formula IIb-1

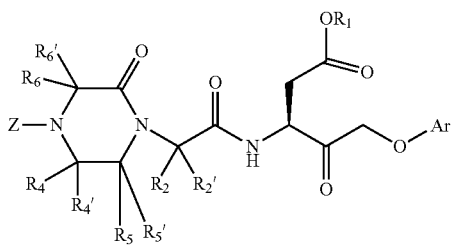

IIb-1 or pharmaceutically acceptable salts, solvates, tautomers and isomers thereof, wherein Ar, Z, $R_1$, $R_2$, $R_{2'}$, $R_4$, $R_{4'}$, $R_5$, $R_{5'}$, $R_6$ and $R_{6'}$ are as defined elsewhere herein.

In further embodiments, the compounds provided herein have the structure of Formula IIc-1

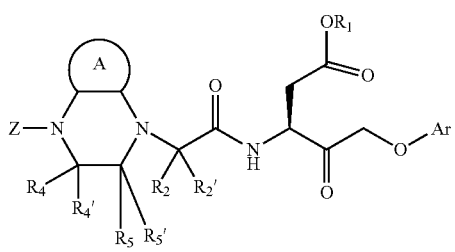

IIc-1 or pharmaceutically acceptable salts, solvates, tautomers and isomers thereof, wherein Ar, Z, $R_1$, $R_2$, $R_{2'}$, $R_4$, $R_{4'}$, $R_5$, $R_{5'}$, and ring A are as defined elsewhere herein.

In further embodiments, the compounds provided herein have the structure of Formula IId-1

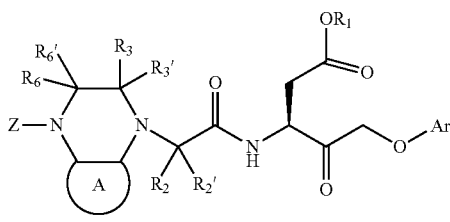

IId-1 or pharmaceutically acceptable salts, solvates, tautomers and isomers thereof, wherein Ar, Z, $R_1$, $R_2$, $R_{2'}$, $R_3$, $R_{3'}$, $R_6$, $R_{6'}$ and ring A are as defined elsewhere herein.

In further embodiments, the compounds provided herein have the structure of Formula II-2

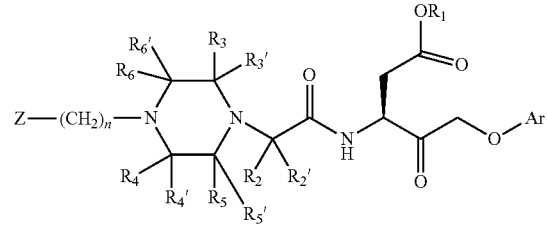

II-2 or pharmaceutically acceptable salts, solvates, tautomers and isomers thereof, wherein n is 1-4, Ar, Z, $R_1$, $R_2$, $R_{2'}$, $R_3$, $R_{3'}$, $R_4$, $R_{4'}$, $R_5$, $R_{5'}$, $R_6$ and $R_{6'}$ are as defined elsewhere herein.

In further embodiments, the compounds provided herein have the structure of Formula IIa-2

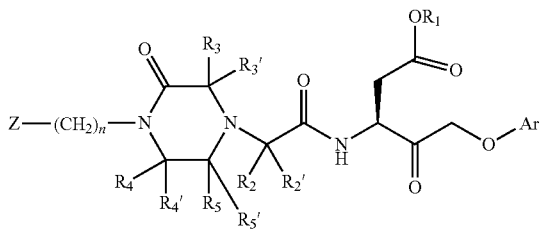

IIa-2 or pharmaceutically acceptable salts, solvates, tautomers and isomers thereof, wherein n is 1-4, Ar, Z, $R_1$, $R_2$, $R_{2'}$, $R_3$, $R_{3'}$, $R_4$, $R_{4'}$, $R_5$, and $R_{5'}$ are as defined elsewhere herein.

In further embodiments, the compounds provided herein have the structure of Formula IIb-2

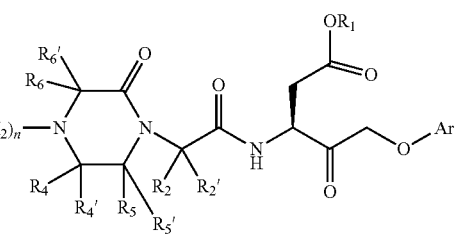

IIb-2 or pharmaceutically acceptable salts, solvates, tautomers and isomers thereof, wherein n is 1-4, Ar, Z, $R_1$, $R_2$, $R_{2'}$, $R_4$, $R_{4'}$, $R_5$, $R_{5'}$, $R_6$ and $R_{6'}$ are as defined elsewhere herein.

In further embodiments, the compounds provided herein have the structure of Formula IIc-2

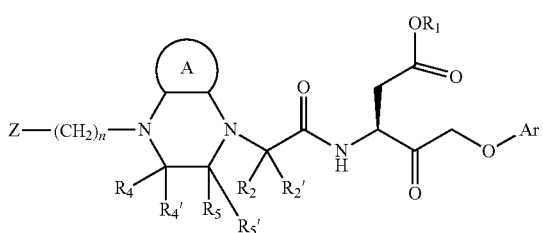

IIc-2 or pharmaceutically acceptable salts, solvates, tautomers and isomers thereof, wherein n is 1-4, Ar, Z, $R_1$, $R_2$, $R_{2'}$, $R_4$, $R_{4'}$, $R_5$, $R_{5'}$, and ring A are as defined elsewhere herein.

In further embodiments, the compounds provided herein have the structure of Formula IId-2

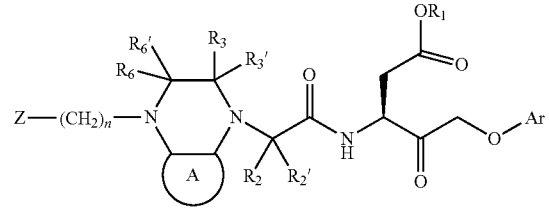

IId-2 or pharmaceutically acceptable salts, solvates, tautomers and isomers thereof, wherein n is 1-4, Ar, Z, $R_1$, $R_2$, $R_{2'}$, $R_3$, $R_{3'}$, $R_6$, $R_{6'}$ and ring A are as defined elsewhere herein.

In further embodiments, the compounds provided herein have the structure of Formula II-3

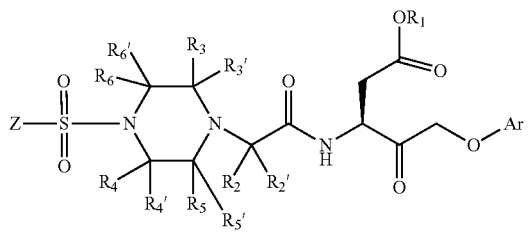

II-3 or pharmaceutically acceptable salts, solvates, tautomers and isomers thereof, wherein Ar, Z, $R_1$, $R_2$, $R_{2'}$, $R_3$, $R_{3'}$, $R_4$, $R_{4'}$, $R_5$, $R_{5'}$, $R_6$ and $R_{6'}$ are as defined elsewhere herein.

In further embodiments, the compounds provided herein have the structure of Formula IIa-3

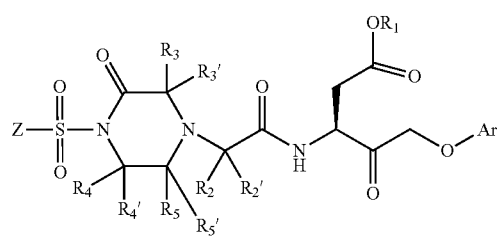

IIa-3 or pharmaceutically acceptable salts, solvates, tautomers and isomers thereof, wherein Ar, Z, $R_1$, $R_2$, $R_{2'}$, $R_3$, $R_{3'}$, $R_4$, $R_{4'}$, $R_5$, and $R_{5'}$ are as defined elsewhere herein.

In further embodiments, the compounds provided herein have the structure of Formula IIb-3

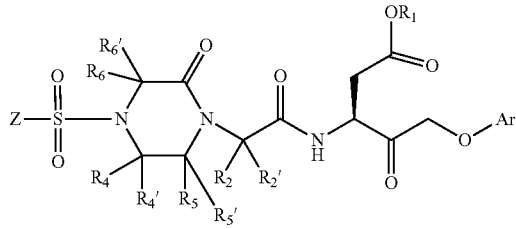

IIb-3 or pharmaceutically acceptable salts, solvates, tautomers and isomers thereof, wherein Ar, Z, $R_1$, $R_2$, $R_{2'}$, $R_4$, $R_{4'}$, $R_5$, $R_{5'}$, $R_6$ and $R_{6'}$ are as defined elsewhere herein.

In further embodiments, the compounds provided herein have the structure of Formula IIc-3

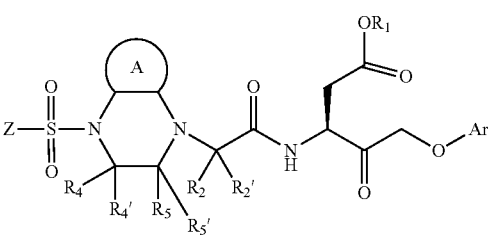

IIc-3 or pharmaceutically acceptable salts, solvates, tautomers and isomers thereof, wherein Ar, Z, $R_1$, $R_2$, $R_{2'}$, $R_4$, $R_{4'}$, $R_5$, $R_{5'}$, and ring A are as defined elsewhere herein.

In further embodiments, the compounds provided herein have the structure of Formula IId-3

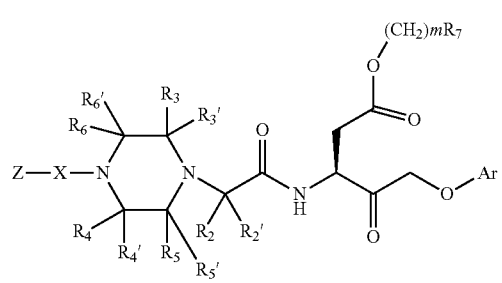

IId-3 or pharmaceutically acceptable salts, solvates, tautomers and isomers thereof, wherein Ar, Z, Ra, $R_2$, $R_{2'}$, $R_3$, $R_{3'}$, $R_6$, $R_{6'}$ and ring A are as defined elsewhere herein.

In certain embodiment, provided herein are compounds of Formula III

III or pharmaceutically acceptable salts, solvates, tautomers and isomers thereof, wherein $R_7$ is hydrogen or optionally substituted phenyl, wherein the substituents when present are selected from 1 to 4 groups $Q^1$;

m is 0-6;

Ar, Z, X, $R_2$, $R_{2'}$, $R_3$, $R_{3'}$, $R_4$, $R_{4'}$, $R_5$, $R_{5'}$, $R_6$, $R_{6'}$ and $Q^1$ are as defined elsewhere herein.

In certain embodiment, provided herein are compounds of Formula IIIa

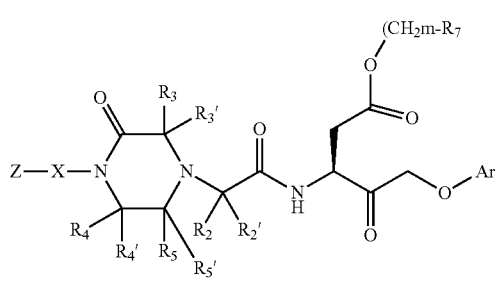

or pharmaceutically acceptable salts, solvates, tautomers and isomers thereof, wherein $R_7$ is hydrogen or optionally substituted phenyl, wherein the substituents when present are selected from 1 to 4 groups $Q^1$;

m is 0-6;

Ar, Z, X, $R_2$, $R_{2'}$, $R_3$, $R_{3'}$, $R_4$, $R_{4'}$, $R_5$, $R_{5'}$ and $Q^1$ are as defined elsewhere herein.

In certain embodiment, provided herein are compounds of Formula IIIb

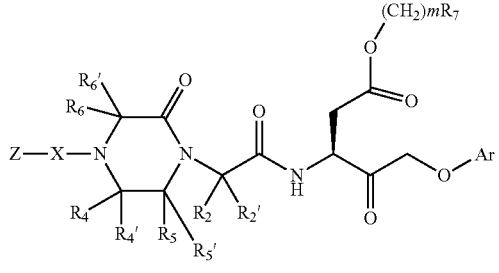

or pharmaceutically acceptable salts, solvates, tautomers and isomers thereof, wherein $R_7$ is hydrogen or optionally substituted phenyl, wherein the substituents when present are selected from 1 to 4 groups $Q^1$;

m is 0-6;

Ar, Z, X, $R_2$, $R_{2'}$, $R_4$, $R_{4'}$, $R_5$, $R_{5'}$, $R_6$, $R_{6'}$ and $Q^1$ are as defined elsewhere herein.

In certain embodiment, provided herein are compounds of Formula IIIc

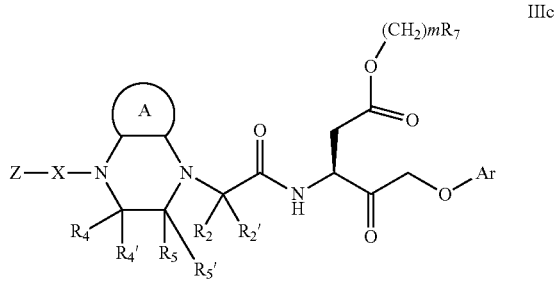

or pharmaceutically acceptable salts, solvates, tautomers and isomers thereof, wherein $R_7$ is hydrogen or optionally substituted phenyl, wherein the substituents when present are selected from 1 to 4 groups $Q^1$;

m is 0-6;

Ar, Z, X, $R_2$, $R_{2'}$, $R_4$, $R_{4'}$, $R_5$, $R_{5'}$, ring A and $Q^1$ are as defined elsewhere herein.

In certain embodiment, provided herein are compounds of Formula IIId

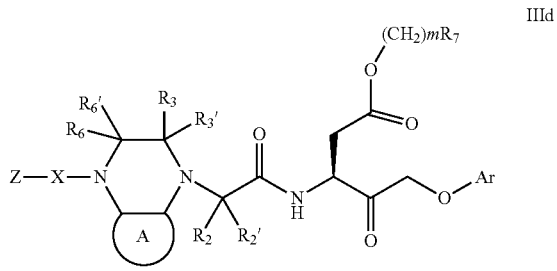

or pharmaceutically acceptable salts, solvates, tautomers and isomers thereof, wherein $R_7$ is hydrogen or optionally substituted phenyl, wherein the substituents when present are selected from 1 to 4 groups $Q^1$;

m is 0-6;

Ar, Z, X, $R_2$, $R_{2'}$, $R_3$, $R_{3'}$, $R_6$, $R_{6'}$, ring A and $Q^1$ are as defined elsewhere herein.

In certain embodiments, the compounds provided herein have the structure of Formula III, Formula IIIa, Formula IIIb, Formula IIIc or Formula IIId, wherein m is 0 and $R_7$ is hydrogen.

In certain embodiments, the compounds provided herein have the structure of Formula III, Formula IIIa, Formula IIIb, Formula IIIc or Formula IIId, wherein m is 0-1, and $R_7$ is phenyl.

In certain embodiments, the compounds provided herein have the structure of Formula III, Formula IIIa, Formula IIIb, Formula IIIc or Formula IIId, wherein m is 1, and $R_7$ is phenyl.

In certain embodiment, provided herein are compounds of Formula IV

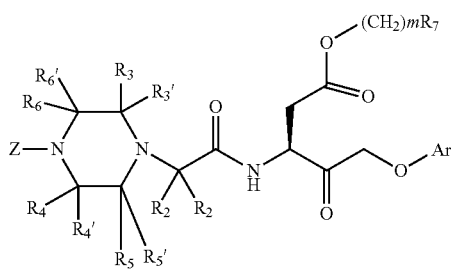

IV or pharmaceutically acceptable salts, solvates, tautomers and isomers thereof,
wherein $R_7$ is hydrogen, optionally substituted phenyl, wherein the substituents when present are selected from 1 to 4 groups $Q^1$;
m is 0-6;
Ar, Z, $R_2$, $R_{2'}$, $R_3$, $R_{3'}$, $R_4$, $R_{4'}$, $R_5$, $R_{5'}$, $R_6$, $R_{6'}$ and $Q^1$ are as defined elsewhere herein.

In certain embodiment, provided herein are compounds of Formula IVa

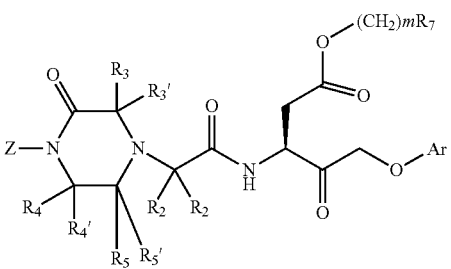

IVa or pharmaceutically acceptable salts, solvates, tautomers and isomers thereof,
wherein $R_7$ is hydrogen, optionally substituted phenyl, wherein the substituents when present are selected from 1 to 4 groups $Q^1$;
m is 0-6;
Ar, Z, $R_2$, $R_{2'}$, $R_3$, $R_{3'}$, $R_4$, $R_{4'}$, $R_5$, $R_{5'}$, and $Q^1$ are as defined elsewhere herein.

In certain embodiment, provided herein are compounds of Formula IVb

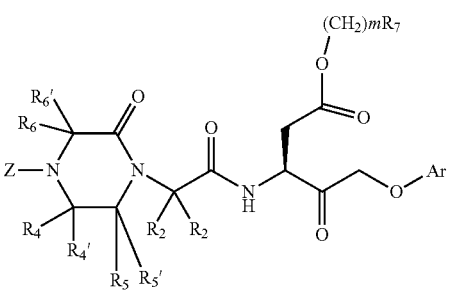

IVb or pharmaceutically acceptable salts, solvates, tautomers and isomers thereof,
wherein $R_7$ is hydrogen, optionally substituted phenyl, wherein the substituents when present are selected from 1 to 4 groups $Q^1$;
m is 0-6;
Ar, Z, $R_2$, $R_{2'}$, $R_4$, $R_{4'}$, $R_5$, $R_{5'}$, $R_6$, $R_{6'}$ and $Q^1$ are as defined elsewhere herein.

In certain embodiment, provided herein are compounds of Formula IVc

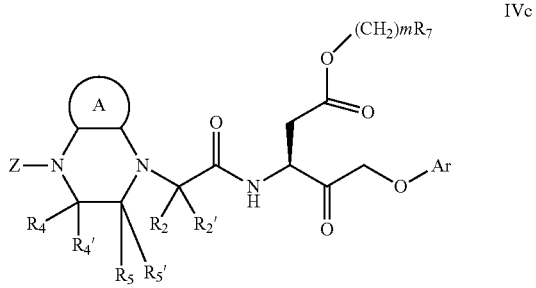

IVc or pharmaceutically acceptable salts, solvates, tautomers and isomers thereof,
wherein $R_7$ is hydrogen, optionally substituted phenyl, wherein the substituents when present are selected from 1 to 4 groups $Q^1$;
m is 0-6;
Ar, Z, $R_2$, $R_{2'}$, $R_4$, $R_{4'}$, $R_5$, $R_{5'}$, ring A and $Q^1$ are as defined elsewhere herein.

In certain embodiment, provided herein are compounds of Formula IVd

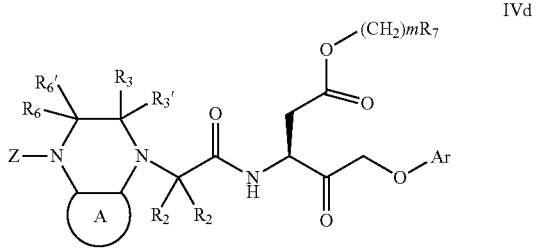

IVd or pharmaceutically acceptable salts, solvates, tautomers and isomers thereof,
wherein $R_7$ is hydrogen, optionally substituted phenyl, wherein the substituents when present are selected from 1 to 4 groups $Q^1$;
m is 0-6;
Ar, Z, $R_2$, $R_{2'}$, $R_3$, $R_{3'}$, $R_6$, $R_{6'}$, ring A and $Q^1$ are as defined elsewhere herein.

In certain embodiments, the compounds provided herein have the structure of Formula IV, Formula IVa, Formula IVb, Formula IVc or Formula IVd, wherein m is 0 and $R_7$ is hydrogen.

In certain embodiments, the compounds provided herein have the structure of Formula IV, Formula IVa, Formula IVb, Formula IVc or Formula IVd, wherein m is 0-4, and $R_7$ is phenyl.

In certain embodiments, the compounds provided herein have the structure of Formula IV, Formula IVa, Formula IVb, Formula IVc or Formula IVd, wherein m is 1, and $R_7$ is phenyl.

In some embodiments, provided herein are compounds of Formula I, Ia, Ib, Ic or Id, wherein $R_2$ and $R_{2'}$ combine with the carbon to which they are attached to form a 3-7 membered monocyclic cycloalkyl or 5-7 membered monocyclic heterocycloalkyl, wherein the monocyclic cycloalkyl or monocyclic heterocycloalkyl are optionally substituted with one or more substituents selected from the group consisting of halogen, —OH, —NH$_2$, lower alkyl, halogen substituted lower alkyl, lower alkoxy, halogen substituted lower alkoxy, lower alkylthio, halogen substituted lower alkylthio, monoalkylamino, di-alkylamino, and cycloalkylamino; and Ar, Z, X, R$_1$, R$_3$, R$_3$', R$_4$, R$_4$', R$_5$, R$_5$', R$_6$ and R$_6$' are as defined for Formula I, Formula Ia, Formula Ib, Formula Ic and Formula Id, including embodiments thereof, respectively. In some embodiments, R$_2$ and R$_2$' combine with the carbon to which they are attached to form a 3-7 membered monocyclic cycloalkyl. In further embodiments, R$_2$ and R$_2$' combine with the carbon to which they are attached to form a cyclopentyl.

In certain embodiment, provided herein are compounds of Formula V

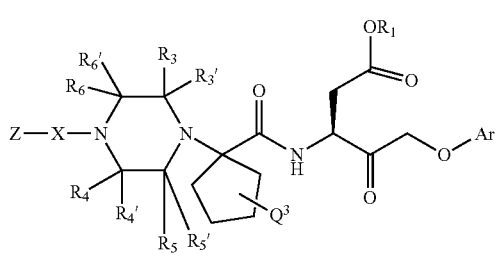

V or pharmaceutically acceptable salts, solvates, tautomers and isomers thereof, wherein Q$^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, monoalkylamino, di-alkylamino, and cycloalkylamino;

Ar, Z, X, R$_1$, R$_3$, R$_3$', R$_4$, R$_4$', R$_5$, R$_5$', R$_6$ and R$_6$' are as defined elsewhere herein.

In certain embodiment, provided herein are compounds of Formula Va

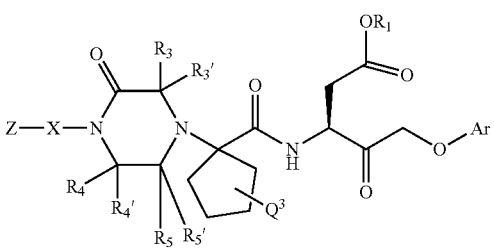

Va or pharmaceutically acceptable salts, solvates, tautomers and isomers thereof, wherein Q$^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, monoalkylamino, di-alkylamino, and cycloalkylamino;

Ar, Z, X, R$_1$, R$_3$, R$_3$', R$_4$, R$_4$', R$_5$, R$_5$', R$_6$ and R$_6$' are as defined elsewhere herein.

In certain embodiment, provided herein are compounds of Formula Vb

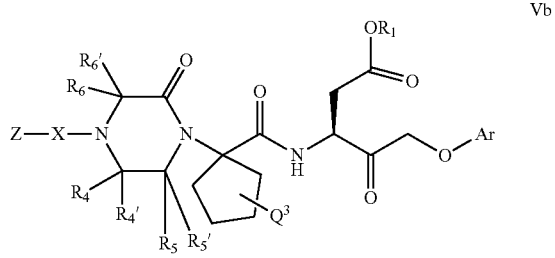

Vb or pharmaceutically acceptable salts, solvates, tautomers and isomers thereof, wherein Q$^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, monoalkylamino, di-alkylamino, and cycloalkylamino;

Ar, Z, X, R$_1$, R$_3$, R$_3$', R$_4$, R$_4$', R$_5$, R$_5$', R$_6$ and R$_6$' are as defined elsewhere herein.

In certain embodiment, provided herein are compounds of Formula Vc

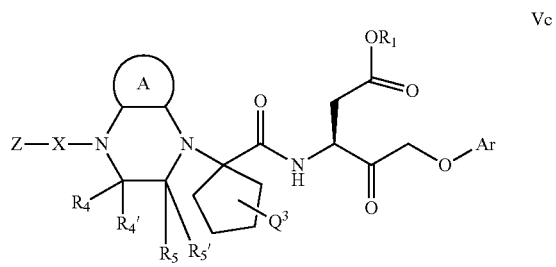

Vc or pharmaceutically acceptable salts, solvates, tautomers and isomers thereof, wherein Q$^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, monoalkylamino, di-alkylamino, and cycloalkylamino;

Ar, Z, X, R$_1$, R$_3$, R$_3$', R$_4$, R$_4$', R$_5$, R$_5$', R$_6$ and R$_6$' are as defined elsewhere herein.

In certain embodiment, provided herein are compounds of Formula Vd

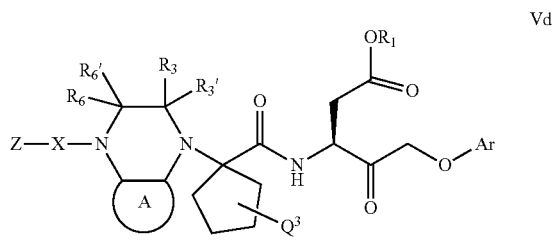

Vd or pharmaceutically acceptable salts, solvates, tautomers and isomers thereof, wherein Q$^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, monoalkylamino, di-alkylamino, and cycloalkylamino;

Ar, Z, X, $R_1$, $R_3$, $R_{3'}$, $R_4$, $R_{4'}$, $R_5$, $R_{5'}$, $R_6$ and $R_{6'}$ are as defined elsewhere herein.

In some embodiments, provided herein are compounds of Formula II, IIa, IIb, IIc or IId, wherein, $R_2$ and $R_{2'}$ combine with the carbon to which they are attached to form a 3-7 membered monocyclic cycloalkyl or 5-7 membered monocyclic heterocycloalkyl, wherein the monocyclic cycloalkyl or monocyclic heterocycloalkyl are optionally substituted with one or more substituents selected from the group consisting of halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, X, $R_1$, $R_3$, $R_{3'}$, $R_4$, $R_{4'}$, $R_5$, $R_{5'}$, $R_6$ and $R_{6'}$ are as defined for Formula II, Formula IIa, Formula IIb, Formula IIc and Formula IId, including embodiments thereof, respectively. In some embodiments, $R_2$ and $R_{2'}$ combine with the carbon to which they are attached to form a 3-7 membered monocyclic cycloalkyl. In further embodiments, $R_2$ and $R_{2'}$ combine with the carbon to which they are attached to form a cyclopentyl.

In certain embodiment, provided herein are compounds of Formula VI-1

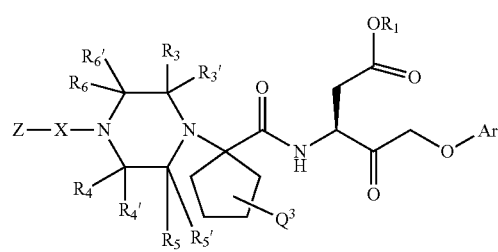

VI-1 or pharmaceutically acceptable salts, solvates, tautomers and isomers thereof,
wherein $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;
Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula VIa-1

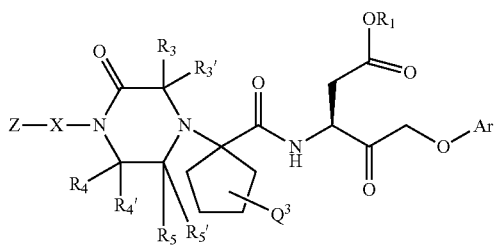

VIa-1 or pharmaceutically acceptable salts, solvates, tautomers and isomers thereof,
wherein $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;
Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula VIb-1

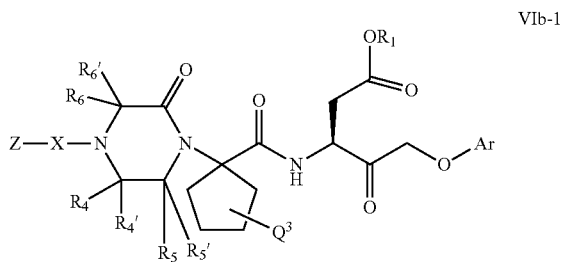

VIb-1 or pharmaceutically acceptable salts, solvates, tautomers and isomers thereof,
wherein $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;
Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula VIc-1

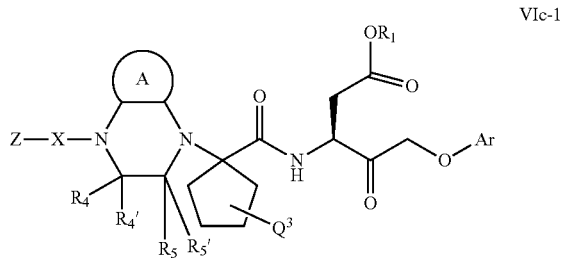

VIc-1 or pharmaceutically acceptable salts, solvates, tautomers and isomers thereof,
wherein $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;
Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula VId-1

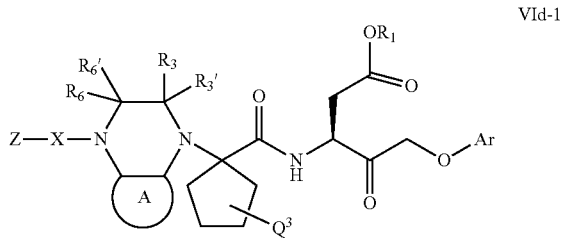

VId-1 or pharmaceutically acceptable salts, solvates, tautomers and isomers thereof, wherein $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula VI-2

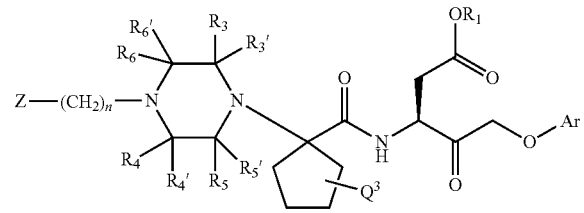

VI-2 or pharmaceutically acceptable salts, solvates, tautomers and isomers thereof, wherein n is 1-4, $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula VIa-2

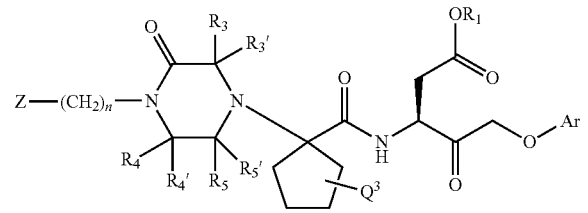

VIa-2 or pharmaceutically acceptable salts, solvates, tautomers and isomers thereof, wherein n is 1-4, $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula VIb-2

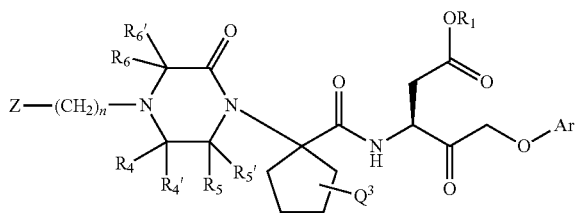

VIb-2 or pharmaceutically acceptable salts, solvates, tautomers and isomers thereof, wherein n is 1-4, $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula VIc-2

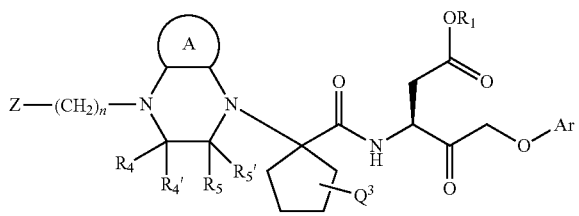

VIc-2 or pharmaceutically acceptable salts, solvates, tautomers and isomers thereof, wherein n is 1-4, $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment provided herein are compounds of Formula VId-2

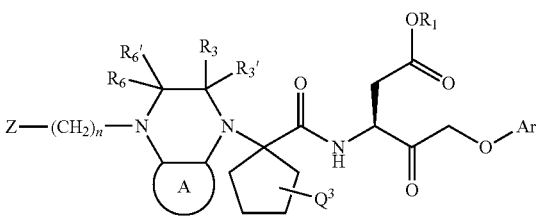

VId-2 or pharmaceutically acceptable salts, solvates, tautomers and isomers thereof, wherein n is 1-4, $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment provided herein are compounds of Formula VI-3

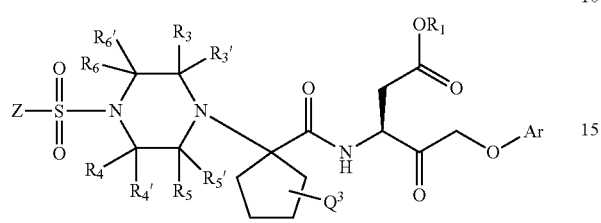

VI-3 or pharmaceutically acceptable salts, solvates, tautomers and isomers thereof, wherein $Q^3$ is selected from halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, $R_1$, $R_3$, $R_{3'}$, $R_4$, $R_{4'}$, $R_5$, $R_{5'}$, $R_6$ and $R_{6'}$ are as defined elsewhere herein.

In certain embodiment provided herein are compounds of Formula VIa-3

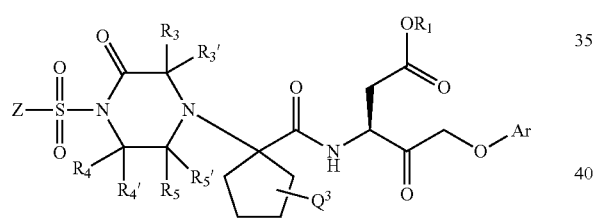

VIa-3 or pharmaceutically acceptable salts, solvates, tautomers and isomers thereof, wherein $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, $R_1$, $R_3$, $R_{3'}$, $R_4$, $R_{4'}$, $R_5$, $R_{5'}$, $R_6$ and $R_{6'}$ are as defined elsewhere herein.

In certain embodiment provided herein are compounds of Formula VIb-3

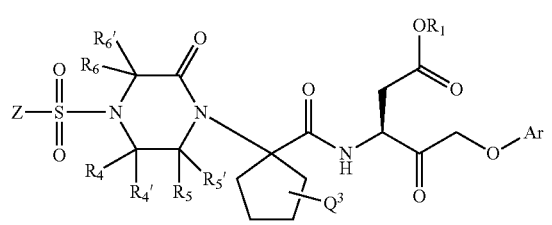

VIb-3 or pharmaceutically acceptable salts, solvates, tautomers and isomers thereof, wherein $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula VIc-2

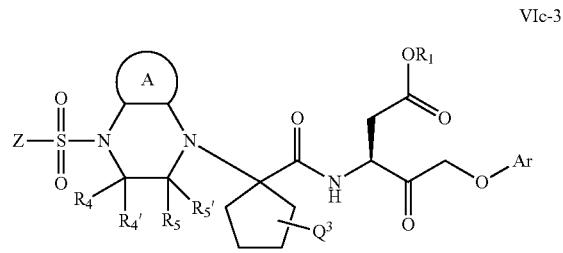

VIc-3 or pharmaceutically acceptable salts, solvates, tautomers and isomers thereof, wherein $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula VId-3

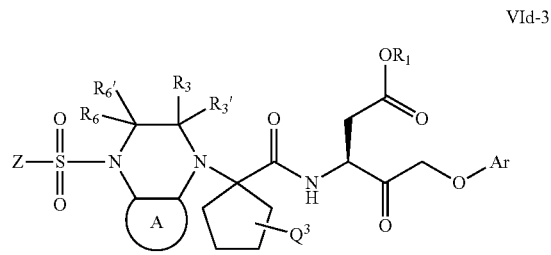

VId-3 or pharmaceutically acceptable salts, solvates, tautomers and isomers thereof, wherein $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, $R_1$, $R_3$, $R_{3'}$, $R_4$, $R_{4'}$, $R_5$, $R_{5'}$, $R_6$ and $R_{6'}$ are as defined elsewhere herein.

In further embodiments, provided herein are compounds of Formula III, Formula IIIa, Formula IIIb, Formula IIIc or Formula Hid, wherein $R_2$ and $R_{2'}$ combine with the carbon to which they are attached to form a 3-7 membered monocyclic cycloalkyl or 5-7 membered monocyclic heterocycloalkyl, wherein the monocyclic cycloalkyl or monocyclic heterocycloalkyl are optionally substituted with one or more substituents selected from the group consisting of halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

R$_7$ is hydrogen or optionally substituted phenyl, wherein the substituents when present are selected from 1 to 4 groups Q;

m is 0-6;

Ar, Z, X, R$_1$, R$_3$, R$_{3'}$, R$_4$, R$_{4'}$, R$_5$, R$_{5'}$, R$_6$ and R$_{6'}$ are as defined for Formula III, Formula IIIa, Formula IIIb, Formula IIIc and Formula IIId, including embodiments thereof, respectively. In some embodiments, R$_2$ and R$_{2'}$ combine with the carbon to which they are attached to form a 3-7 membered monocyclic cycloalkyl. In further embodiments, R$_2$ and R$_{2'}$ combine with the carbon to which they are attached to form a cyclopentyl.

In certain embodiment, provided herein are compounds of Formula VII

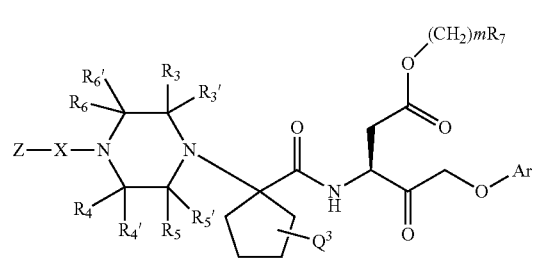

VII or pharmaceutically acceptable salts, solvates, tautomers and isomers thereof, wherein R$_7$ is hydrogen or optionally substituted phenyl, wherein the substituents when present are selected from 1 to 4 groups Q$^1$;

m is 0-6;

Q$^3$ is hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, X, R$_1$, R$_3$, R$_{3'}$, R$_4$, R$_{4'}$, R$_5$, R$_{5'}$, R$_6$, R$_{6'}$ and Q$^1$ are as defined elsewhere herein.

In certain embodiment, provided herein are compounds of Formula VIIa

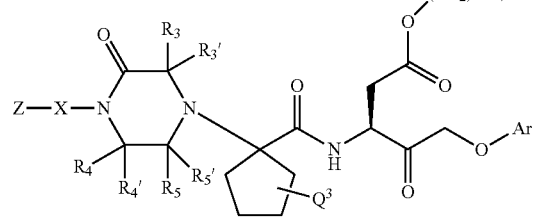

VIIa or pharmaceutically acceptable salts, solvates, tautomers and isomers thereof, wherein R7 is hydrogen or optionally substituted phenyl, wherein the substituents when present are selected from 1 to 4 groups Q$^1$;

m is 0-6;

Q$^3$ is hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, X, R$_3$, R$_{3'}$, R$_4$, R$_{4'}$, R$_5$, R$_{5'}$, and Q$^1$ are as defined elsewhere herein.

In certain embodiment, provided herein are compounds of Formula VIIb

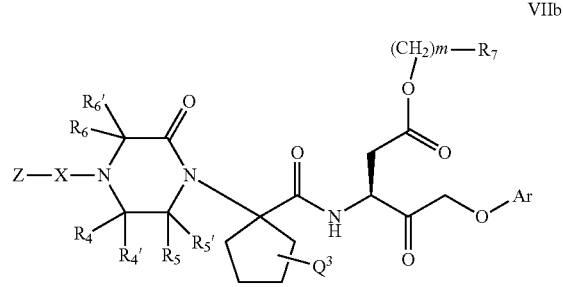

VIIb or pharmaceutically acceptable salts, solvates, tautomers and isomers thereof, wherein R7 is hydrogen or optionally substituted phenyl, wherein the substituents when present are selected from 1 to 4 groups Q$^1$;

m is 0-6;

Q$^3$ is hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, X, R$_4$, R$_{4'}$, R$_5$, R$_{5'}$, R$_6$, R$_{6'}$ and Q$^1$ are as defined elsewhere herein.

In certain embodiment, provided herein are compounds of Formula VIIc

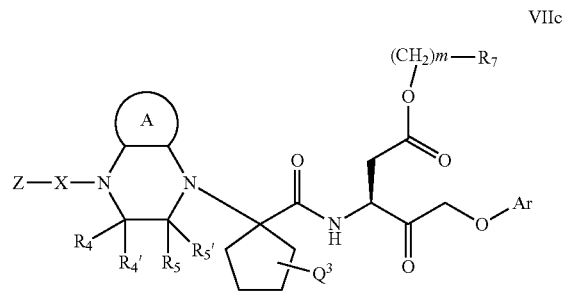

VIIc or pharmaceutically acceptable salts, solvates, tautomers and isomers thereof, wherein R$_7$ is hydrogen or optionally substituted phenyl, wherein the substituents when present are selected from 1 to 4 groups Q$^1$;

m is 0-6;

Q$^3$ is hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, X, R$_4$, R$_{4'}$, R$_5$, R$_{5'}$, ring A and Q$^1$ are as defined elsewhere herein.

In certain embodiment, provided herein are compounds of Formula VIId

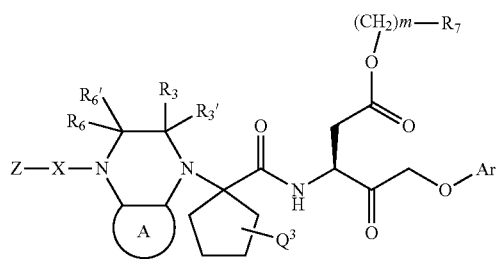

or pharmaceutically acceptable salts, solvates, tautomers and isomers thereof, wherein $R_7$ is hydrogen or optionally substituted phenyl, wherein the substituents when present are selected from 1 to 4 groups $Q^1$;

m is 0-6;

$Q^3$ is hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, X, $R_3$, $R_{3'}$, $R_6$, $R_{6'}$, ring A and $Q^1$ are as defined elsewhere herein.

In certain embodiment, provided herein are compounds of Formula VIII

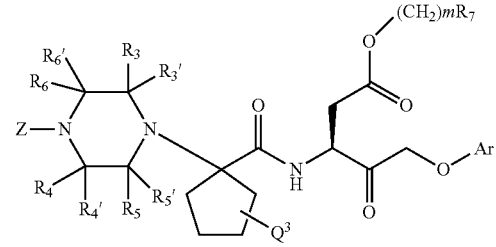

or pharmaceutically acceptable salts, solvates, tautomers and isomers thereof, wherein $R_7$ is hydrogen or optionally substituted phenyl, wherein the substituents when present are selected from 1 to 4 groups $Q^1$;

m is 0-6;

$Q^3$ is hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, $R_3$, $R_{3'}$, $R_4$, $R_{4'}$, $R_5$, $R_{5'}$, $R_6$, $R_{6'}$ and $Q^1$ are as defined elsewhere herein.

In certain embodiment, provided herein are compounds of Formula VIIIa

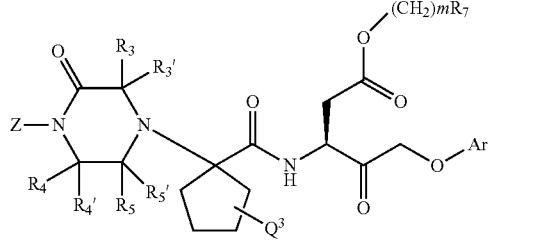

or pharmaceutically acceptable salts, solvates, tautomers and isomers thereof, wherein $R_7$ is hydrogen or optionally substituted phenyl, wherein the substituents when present are selected from 1 to 4 groups $Q^1$;

m is 0-6;

$Q^3$ is hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, $R_3$, $R_{3'}$, $R_4$, $R_{4'}$, $R_5$, $R_{5'}$, and $Q^1$ are as defined elsewhere herein.

In certain embodiment, provided herein are compounds of Formula VIIIb

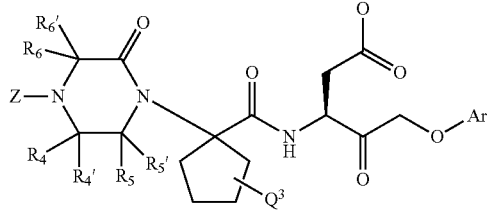

or pharmaceutically acceptable salts, solvates, tautomers and isomers thereof, wherein $R_7$ is hydrogen or optionally substituted phenyl, wherein the substituents when present are selected from 1 to 4 groups $Q^1$;

m is 0-6;

$Q^3$ is hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, $R_4$, $R_{4'}$, $R_5$, $R_{5'}$, $R_6$, $R_{6'}$ and $Q^1$ are as defined elsewhere herein.

In certain embodiment, provided herein are compounds of Formula VIIIc

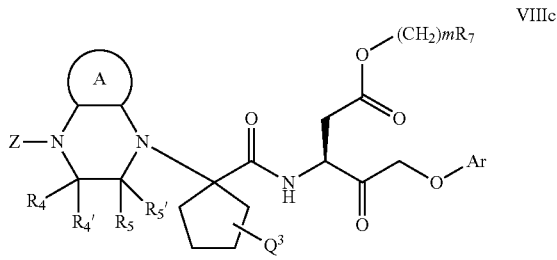

VIIIc or pharmaceutically acceptable salts, solvates, tautomers and isomers thereof, wherein $R_7$ is hydrogen or optionally substituted phenyl, wherein the substituents when present are selected from 1 to 4 groups $Q^1$;

m is 0-6;

$Q^3$ is hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, $R_4$, $R_{4'}$, $R_5$, $R_{5'}$, ring A and $Q^1$ are as defined elsewhere herein.

In certain embodiment, provided herein are compounds of Formula VIIId

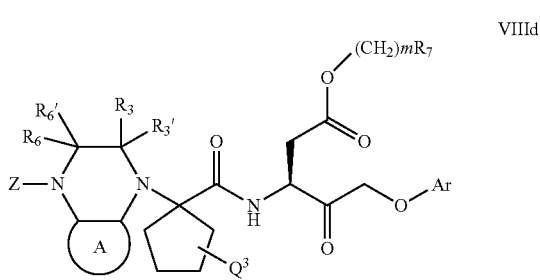

VIIId or pharmaceutically acceptable salts, solvates, tautomers and isomers thereof, wherein $R_7$ is hydrogen or optionally substituted phenyl, wherein the substituents when present are selected from 1 to 4 groups $Q^1$;

m is 0-6;

$Q^3$ is hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, $R_3$, $R_{3'}$, $R_6$, $R_{6'}$, ring A and $Q^1$ are as defined elsewhere herein.

In certain embodiments, the compounds provided herein have the structure of Formula VIII, Formula VIIIa, Formula VIIIb, Formula VIIIc or Formula VIIId, wherein m is 0 and $R_7$ is hydrogen.

In certain embodiments, the compounds provided herein have the structure of Formula VIII, Formula VIIIa, Formula VIIIb, Formula VIIIc or Formula VIIId, wherein m is 0-4, and $R_7$ is phenyl.

In certain embodiments, the compounds provided herein have the structure of Formula VIII, Formula VIIIa, Formula VIIIb, Formula VIIIc or Formula VIIId, wherein m is 1, and $R_7$ is phenyl.

In certain embodiments, the compounds provided herein have the structure of Formula V, Formula Va, Formula Vb, Formula Vc, Formula Vd, Formula VIa-1, Formula VIb-1, Formula VIc-1, Formula VId-1, Formula VI-2, Formula VIa-2, Formula VIb-2, Formula VIc-2, Formula VId-2, Formula VI-3, Formula VIa-3, Formula VIb-3, Formula VIc-3, Formula VId-3, Formula VII, Formula VIIa, Formula VIIb, Formula VIIc, Formula VIId, Formula VIII, Formula VIIIa, Formula VIIIb, Formula VIIIc or Formula VIIId, wherein $Q^3$ is hydrogen.

In some embodiments, provided herein are compounds of Formula I, Formula Ia, Formula Ib, Formula Ic, Formula Id, Formula II-1, Formula IIa-1, Formula IIb-1, Formula IIc-1, Formula IId-1, Formula II-2, Formula IIa-2, Formula IIb-2, Formula IIc-2, Formula IId-2, Formula II-3, Formula IIa-3, Formula IIb-3, Formula IIc-3, Formula IId-3, Formula IV, Formula IVa, Formula IVb, Formula IVc, Formula IVd, Formula V, Formula Va, Formula Vb, Formula Vc, Formula Vd, Formula VIa-1, Formula VIb-1, Formula VIc-1, Formula VId-1, Formula VI-2, Formula VIa-2, Formula VIb-2, Formula VIc-2, Formula VId-2, Formula VI-3, Formula VIa-3, Formula VIb-3, Formula VIc-3, Formula VId-3, Formula VII, Formula VIIa, Formula VIIb, Formula VIIc, Formula VIId, Formula VIII, Formula VIIIa, Formula VIIIb, Formula VIIIc or Formula VIIId, wherein:

Z is aryl or substituted aryl; and

Ar, X, $R_1$, $R_2$, $R_{2'}$, $R_3$, $R_{3'}$, $R_4$, $R_{4'}$, $R_5$, $R_{5'}$, $R_6$ and $R_{6'}$ are as defined for Formula I, Formula Ia, Formula Ib, Formula Ic and Formula Id, including embodiments thereof, respectively. In some embodiments, Z is phenyl or substituted phenyl. In further embodiments, Z is phenyl. In embodiments, Z is benzyl or substituted benzyl. In some embodiments, Z is benzyl.

In some embodiments, provided herein are compounds of Formula IX

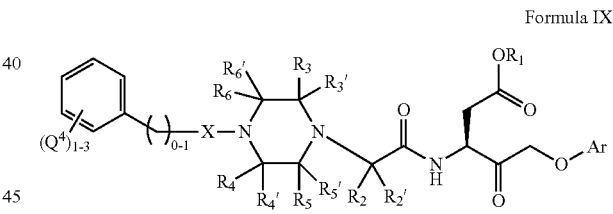

Formula IX or pharmaceutically acceptable salts, solvates, tautomers or isomers thereof, wherein $Q^4$ is hydrogen or $Q^1$, $Q^1$, Ar, Z, X, $R_1$, $R_2$, $R_{2'}$, $R_3$, $R_{3'}$, $R_4$, $R_{4'}$, $R_5$, $R_{5'}$, $R_6$ and $R_{6'}$ are as defined elsewhere herein.

In some embodiments, provided herein are compounds of Formula IXa

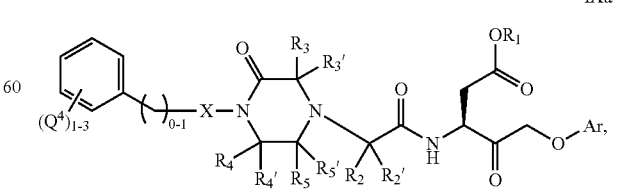

IXa or pharmaceutically acceptable salts, solvates, tautomers and isomers thereof, wherein $Q^4$ is hydrogen or $Q^1$, $Q^1$, Ar, Z, X, $R_1$, $R_2$, $R_{2'}$, $R_3$, $R_{3'}$, $R_4$, $R_{4'}$, $R_5$ and $R_{5'}$ are as defined elsewhere herein.

In some embodiments, provided herein are compounds of Formula IXb,

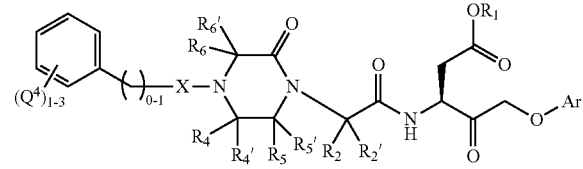

IXb or pharmaceutically acceptable salts, solvates, tautomers and isomers thereof, wherein $Q^1$, Ar, Z, X, $R_1$, $R_2$, $R_{2'}$, $R_4$, $R_{4'}$, $R_5$, $R_{5'}$, $R_6$ and $R_{6'}$ are as defined elsewhere herein.

In some embodiments, provided herein are compounds of Formula IXc,

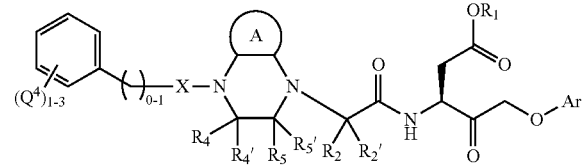

IXc or pharmaceutically acceptable salts, solvates, tautomers and isomers thereof, wherein $Q^4$ is hydrogen or $Q^1$, $Q^1$, Ar, Z, X, $R_1$, $R_2$, $R_{2'}$, $R_4$, $R_{4'}$, $R_5$ are as defined elsewhere herein, and ring A is aryl or heteroaryl, each of which is optionally substituted with 1 to 3 substituents $Q^1$.

In some embodiments, the compound of Formula I has the sub-generic structure of Formula IXd,

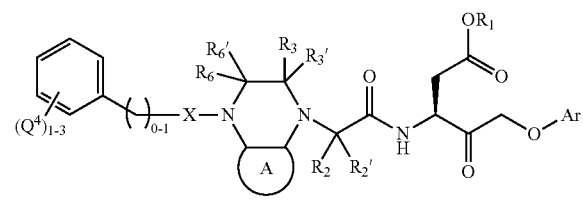

IXd or pharmaceutically acceptable salts, solvates, tautomers and isomers thereof, wherein $Q^4$ is hydrogen or $Q^1$, $Q^1$, Ar, Z, X, $R_1$, $R_2$, $R_{2'}$, $R_3$, $R_{3'}$, $R_6$ and $R_{6'}$ are as defined elsewhere herein, and ring A is aryl or heteroaryl, each of which is optionally substituted with 1 to 3 substituents $Q^1$.

In further embodiments, the compounds provided herein have the structure of Formula X-1

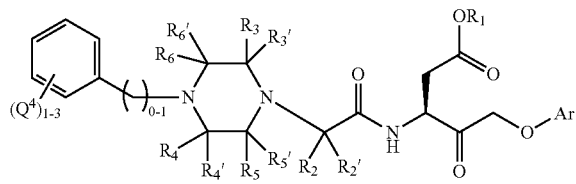

X-1 or pharmaceutically acceptable salts, solvates, tautomers and isomers thereof, wherein $Q^4$ is hydrogen or $Q^1$, $Q^1$, Ar, Z, $R_1$, $R_2$, $R_{2'}$, $R_3$, $R_{3'}$, $R_4$, $R_{4'}$, $R_5$, $R_{5'}$, $R_6$ and $R_{6'}$ are as defined elsewhere herein.

In further embodiments, the compounds provided herein have the structure of Formula Xa-1

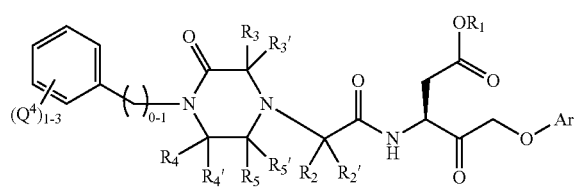

Xa-1 or pharmaceutically acceptable salts, solvates, tautomers and isomers thereof, wherein $Q^4$ is hydrogen or $Q^1$, $Q^1$, Ar, Z, $R_1$, $R_2$, $R_{2'}$, $R_3$, $R_{3'}$, $R_4$, $R_{4'}$, $R_5$, and $R_{5'}$ are as defined elsewhere herein.

In further embodiments, the compounds provided herein have the structure of Formula Xb-1

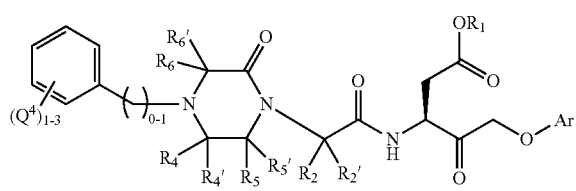

Xb-1 or pharmaceutically acceptable salts, solvates, tautomers and isomers thereof, wherein $Q^4$ is hydrogen or $Q^1$, $Q^1$, Ar, Z, $R_1$, $R_2$, $R_{2'}$, $R_4$, $R_{4'}$, $R_5$, $R_{5'}$, $R_6$ and $R_{6'}$ are as defined elsewhere herein.

In further embodiments, the compounds provided herein have the structure of Formula Xc-1

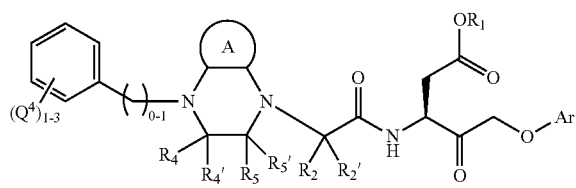

Xc-1 or pharmaceutically acceptable salts, solvates, tautomers and isomers thereof, wherein $Q^4$ is hydrogen or $Q^1$, $Q^1$, Ar, Z, $R_1$, $R_2$, $R_{2'}$, $R_4$, $R_{4'}$, $R_5$, $R_{5'}$ and ring A are as defined elsewhere herein.

In further embodiments, the compounds provided herein have the structure of Formula Xd-1

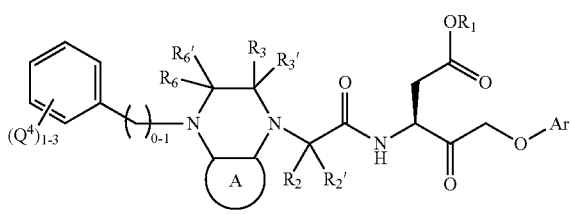

Xd-1 or pharmaceutically acceptable salts, solvates, tautomers and isomers thereof, wherein $Q^4$ is hydrogen or $Q^1$, $Q^1$, Ar, Z, $R_1$, $R_2$, $R_{2'}$, $R_3$, $R_{3'}$, $R_6$, $R_{6'}$ and ring A are as defined elsewhere herein.

In further embodiments, the compounds provided herein have the structure of Formula X-3

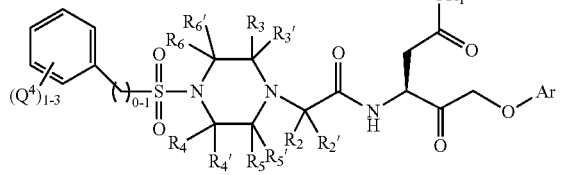

X-3 or pharmaceutically acceptable salts, solvates, tautomers and isomers thereof, wherein $Q^4$ is hydrogen or $Q^1$, $Q^1$, Ar, Z, $R_1$, $R_2$, $R_{2'}$, $R_3$, $R_{3'}$, $R_4$, $R_{4'}$, $R_5$, $R_{5'}$, $R_6$ and $R_{6'}$ are as defined elsewhere herein.

In further embodiments, the compounds provided herein have the structure of Formula Xa-3

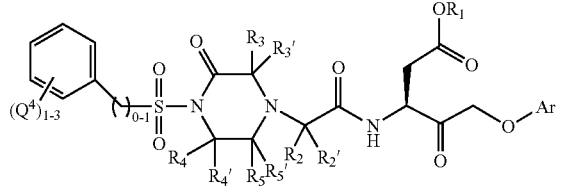

Xa-3 or pharmaceutically acceptable salts, solvates, tautomers and isomers thereof, wherein $Q^4$ is hydrogen or $Q^1$, $Q^1$, Ar, Z, $R_1$, $R_2$, $R_{2'}$, $R_3$, $R_{3'}$, $R_4$, $R_{4'}$, $R_5$, and $R_{5'}$ are as defined elsewhere herein.

In further embodiments, the compounds provided herein have the structure of Formula Xb-3

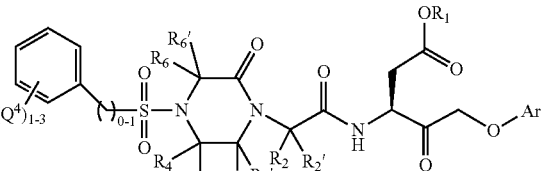

Xb-3 or pharmaceutically acceptable salts, solvates, tautomers and isomers thereof, wherein $Q^4$ is hydrogen or $Q^1$, $Q^1$, Ar, Z, $R_1$, $R_2$, $R_{2'}$, $R_4$, $R_{4'}$, $R_5$, $R_{5'}$, $R_6$ and $R_{6'}$ are as defined elsewhere herein.

In further embodiments, the compounds provided herein have the structure of Formula Xc-3

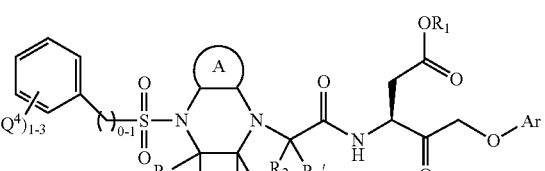

Xc-3 or pharmaceutically acceptable salts, solvates, tautomers and isomers thereof, wherein $Q^4$ is hydrogen or $Q^1$, $Q^1$, Ar, Z, $R_1$, $R_2$, $R_{2'}$, $R_4$, $R_{4'}$, $R_5$, $R_{5'}$, and ring A are as defined elsewhere herein.

In further embodiments, the compounds provided herein have the structure of Formula Xd-3

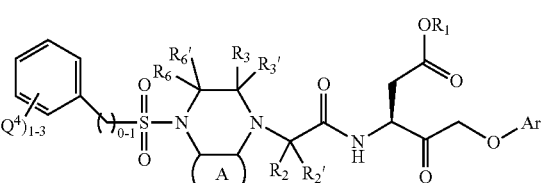

Xd-3 or pharmaceutically acceptable salts, solvates, tautomers and isomers thereof, wherein $Q^4$ is hydrogen or $Q^1$, $Q^1$, Ar, Z, $R_1$, $R_2$, $R_{2'}$, $R_3$, $R_{3'}$, $R_6$, $R_{6'}$ and ring A are as defined elsewhere herein.

In some embodiments, provided herein are compounds of Formula IX, IXa, IXb, IXc, IXd, X-1, Xa-1, Xb-1, Xc-1, Xd-1, X-3, Xa-3, Xb-3, Xc-3, Xd-3, wherein $Q^4$ is hydrogen or $Q^1$, $Q^1$ is halo, alkyl, or haloalkyl, $R_1$ is hydrogen or phenyl, and Ar is phenyl of pyrimidyl, each Ar is optionally substituted with one to four halo or haloalkyl.

In certain embodiment, provided herein are compounds of Formula XI

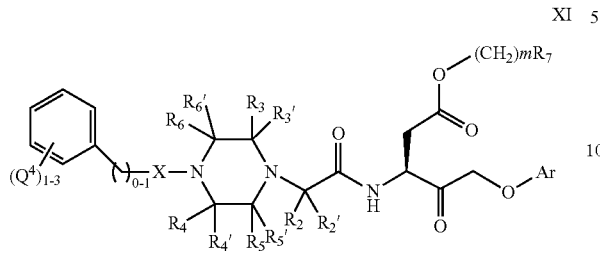

XI or pharmaceutically acceptable salts, solvates, tautomers and isomers thereof,
wherein
$Q^4$ is hydrogen or $Q^1$,
$R_7$ is hydrogen or optionally substituted phenyl, wherein the substituents when present are selected from 1 to 4 groups $Q^1$;
m is 0-6;
Ar, Z, X, $R_2$, $R_{2'}$, $R_3$, $R_{3'}$, $R_4$, $R_{4'}$, $R_5$, $R_{5'}$, $R_6$, $R_{6'}$ and $Q^1$ are as defined elsewhere herein.

In certain embodiment, provided herein are compounds of Formula XIa

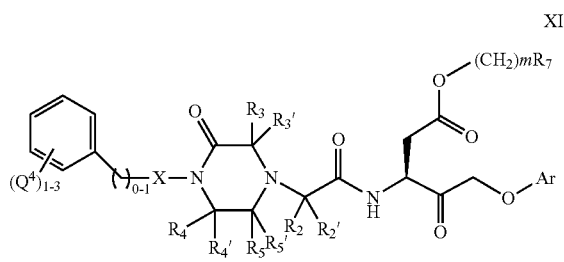

XIa or pharmaceutically acceptable salts, solvates, tautomers and isomers thereof,
wherein
$Q^4$ is hydrogen or $Q^1$,
$R_7$ is hydrogen or optionally substituted phenyl, wherein the substituents when present are selected from 1 to 4 groups $Q^1$;
m is 0-6;
Ar, Z, X, $R_2$, $R_{2'}$, $R_3$, $R_{3'}$, $R_4$, $R_{4'}$, $R_5$, $R_{5'}$, and $Q^1$ are as defined elsewhere herein.

In certain embodiment, provided herein are compounds of Formula XIb

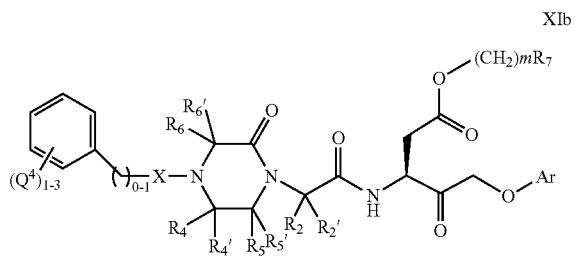

XIb or pharmaceutically acceptable salts, solvates, tautomers and isomers thereof,
wherein
$Q^4$ is hydrogen or $Q^1$,
$R_7$ is hydrogen or optionally substituted phenyl, wherein the substituents when present are selected from 1 to 4 groups $Q^1$;
m is 0-6;
Ar, Z, X, $R_2$, $R_{2'}$, $R_4$, $R_{4'}$, $R_5$, $R_{5'}$, $R_6$, $R_{6'}$ and $Q^1$ are as defined elsewhere herein.

In certain embodiment, provided herein are compounds of Formula XIc

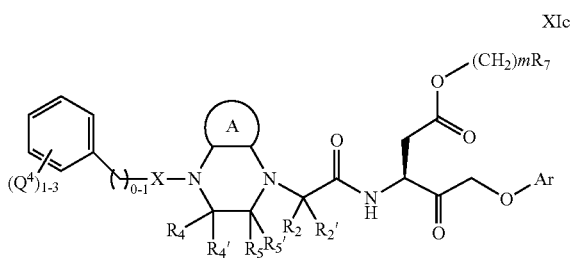

XIc or pharmaceutically acceptable salts, solvates, tautomers and isomers thereof,
wherein $Q^4$ is hydrogen or $Q^1$,
$R_7$ is hydrogen or optionally substituted phenyl, wherein the substituents when present are selected from 1 to 4 groups $Q^1$;
m is 0-6;
Ar, Z, X, $R_2$, $R_{2'}$, $R_4$, $R_{4'}$, $R_5$, $R_{5'}$, ring A and $Q^1$ are as defined elsewhere herein.

In certain embodiment, provided herein are compounds of Formula XId

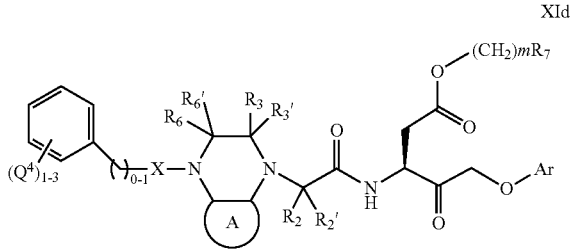

XId or pharmaceutically acceptable salts, solvates, tautomers and isomers thereof,
wherein $Q^4$ is hydrogen or $Q^1$,
$R_7$ is hydrogen or optionally substituted phenyl, wherein the substituents when present are selected from 1 to 4 groups $Q^1$;
m is 0-6;
Ar, Z, X, $R_2$, $R_{2'}$, $R_3$, $R_{3'}$, $R_6$, $R_{6'}$, ring A and $Q^1$ are as defined elsewhere herein.

In certain embodiments, the compounds provided herein have the structure of Formula XI, Formula XIa, Formula XIb, Formula XIc or Formula XId, wherein m is 0 and $R_7$ is hydrogen.

In certain embodiments, the compounds provided herein have the structure of Formula XI, Formula XIa, Formula XIb, Formula XIc or Formula XId, wherein m is 0-4, and $R_7$ is phenyl.

In certain embodiments, the compounds provided herein have the structure of Formula XI, Formula XIa, Formula XIb, Formula XIc or Formula XId, wherein nisi, and $R_7$ is phenyl.

In some embodiments, provided herein are compounds of Formula XI, XIa, XIb, XIc, XId, wherein $Q^4$ is hydrogen or $Q^1$, $Q^1$ is halo, alkyl, or haloalkyl, and Ar is phenyl of pyrimidyl, each Ar is optionally substituted with one to four halo or haloalkyl.

In certain embodiment, provided herein are compounds of Formula XII

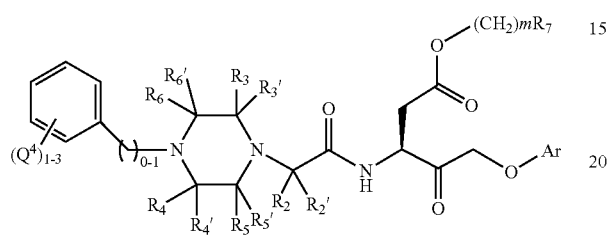

XII or pharmaceutically acceptable salts, solvates, tautomers and isomers thereof, wherein $Q^4$ is hydrogen or $Q^1$, $R_7$ is hydrogen or optionally substituted phenyl, wherein the substituents when present are selected from 1 to 4 groups $Q^1$;

m is 0-6;

Ar, Z, $R_2$, $R_{2'}$, $R_3$, $R_{3'}$, $R_4$, $R_{4'}$, $R_5$, $R_{5'}$, $R_6$, $R_{6'}$ and $Q^1$ are as defined elsewhere herein.

In certain embodiment, provided herein are compounds of Formula XIIa

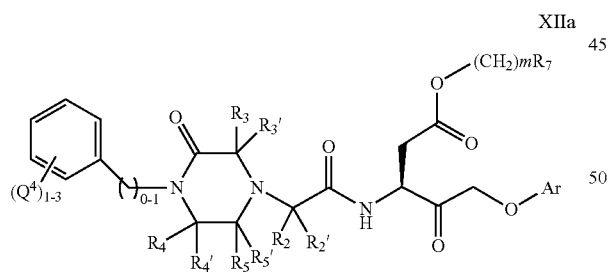

XIIa or pharmaceutically acceptable salts, solvates, tautomers and isomers thereof, wherein $Q^4$ is hydrogen or $Q^1$, $R_7$ is hydrogen or optionally substituted phenyl, wherein the substituents when present are selected from 1 to 4 groups $Q^1$;

m is 0-6;

Ar, Z, $R_2$, $R_{2'}$, $R_3$, $R_{3'}$, $R_4$, $R_{4'}$, $R_5$, $R_{5'}$, and $Q^1$ are as defined elsewhere herein.

In certain embodiment, provided herein are compounds of Formula XIIb

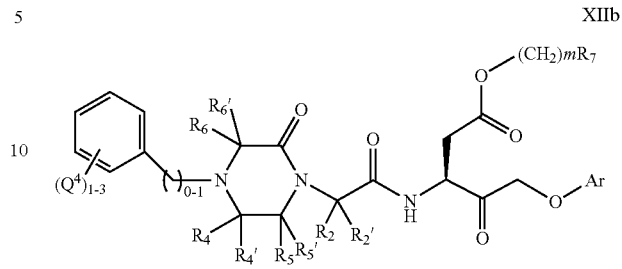

XIIb or pharmaceutically acceptable salts, solvates, tautomers and isomers thereof, wherein $Q^4$ is hydrogen or $Q^1$, $R_7$ is hydrogen or optionally substituted phenyl, wherein the substituents when present are selected from 1 to 4 groups $Q^1$;

m is 0-6;

Ar, Z, $R_2$, $R_{2'}$, $R_4$, $R_{4'}$, $R_5$, $R_{5'}$, $R_6$, $R_{6'}$ and $Q^1$ are as defined elsewhere herein.

In certain embodiment, provided herein are compounds of Formula XIIc

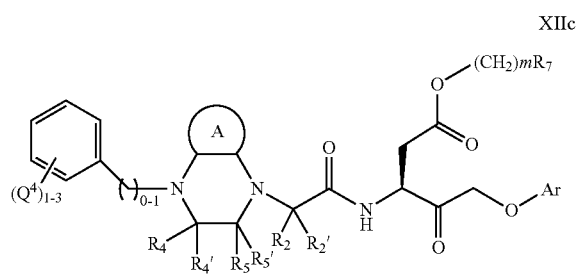

XIIc or pharmaceutically acceptable salts, solvates, tautomers and isomers thereof, wherein $Q^4$ is hydrogen or $Q^1$, $R_7$ is hydrogen or optionally substituted phenyl, wherein the substituents when present are selected from 1 to 4 groups $Q^1$;

m is 0-6;

Ar, Z, $R_2$, $R_{2'}$, $R_4$, $R_{4'}$, $R_5$, $R_{5'}$, ring A and $Q^1$ are as defined elsewhere herein.

In certain embodiment, provided herein are compounds of Formula XIId

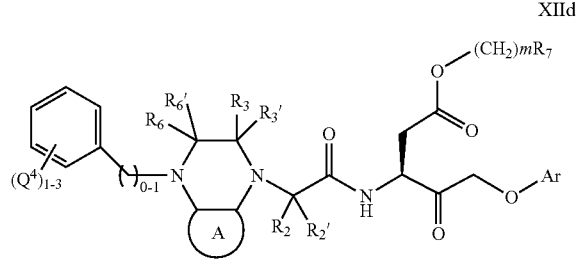

XIId or pharmaceutically acceptable salts, solvates, tautomers and isomers thereof, wherein Q⁴ is hydrogen or Q¹, R₇ is hydrogen or optionally substituted phenyl, wherein the substituents when present are selected from 1 to 4 groups Q¹;

m is 0-6;

Ar, Z, R₂, R₂', R₃, R₃', R₆, R₆', ring A and Q¹ are as defined elsewhere herein.

In certain embodiments, the compounds provided herein have the structure of Formula XII, Formula XIIa, Formula XIIb, Formula XIIc or Formula XIId, wherein m is 0 and R₇ is hydrogen.

In certain embodiments, the compounds provided herein have the structure of Formula XII, Formula XIIa, Formula XIIb, Formula XIIc or Formula XIId, wherein m is 0-4, and R₇ is phenyl.

In certain embodiments, the compounds provided herein have the structure of Formula XII, Formula XIIa, Formula XIIb, Formula XIIc or Formula XIId, wherein m is 1, and R₇ is phenyl.

In some embodiments, provided herein are compounds of Formula XII, XIIa, XIIb, XIIc, XIId, wherein Q⁴ is hydrogen or Q¹, Q¹ is halo, alkyl, or haloalkyl, and Ar is phenyl of pyrimidyl, each Ar is optionally substituted with one to four halo or haloalkyl.

In certain embodiment, provided herein are compounds of Formula XIII

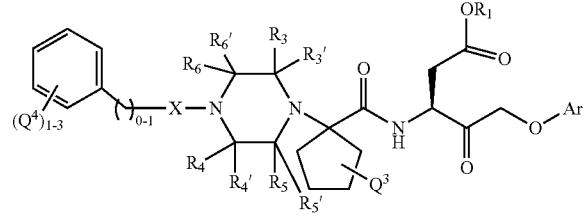

XIII or pharmaceutically acceptable salts, solvates, tautomers and isomers thereof, wherein Q⁴ is hydrogen or Q¹, Q³ is selected from hydrogen, halogen, —OH, —NH₂, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, X, R₁, R₃, R₃', R₄, R₄', R₅, R₅', R₆ and R₆' are as defined elsewhere herein.

In certain embodiment, provided herein are compounds of Formula XIIIa

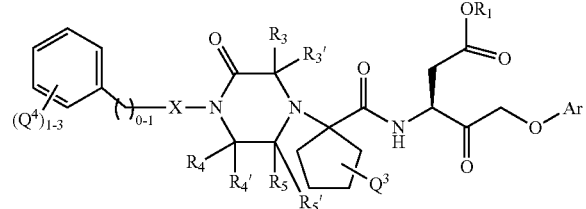

XIIIa or pharmaceutically acceptable salts, solvates, tautomers and isomers thereof, wherein Q⁴ is hydrogen or Q¹, Q³ is selected from hydrogen, halogen, —OH, —NH₂, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, X, R₁, R₃, R₃', R₄, R₄', R₅, R₅', R₆ and R₆' are as defined elsewhere herein.

In certain embodiment, provided herein are compounds of Formula XIIIb

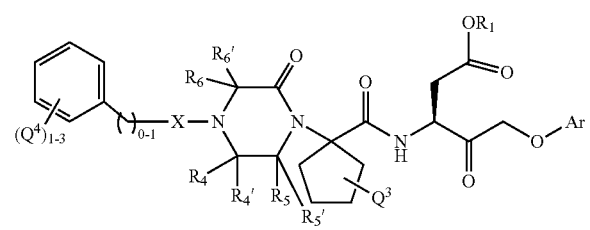

XIIIb or pharmaceutically acceptable salts, solvates, tautomers and isomers thereof, wherein Q⁴ is hydrogen or Q¹, Q³ is selected from hydrogen, halogen, —OH, —NH₂, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, X, R₁, R₃, R₃', R₄, R₄', R₅, R₅', R₆ and R₆' are as defined elsewhere herein.

In certain embodiment, provided herein are compounds of Formula XIIIc

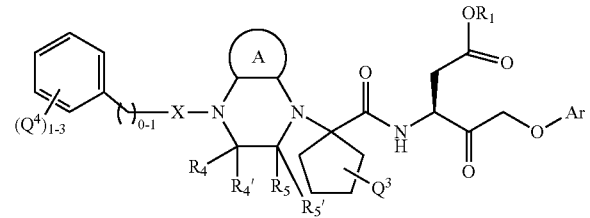

XIIIc or pharmaceutically acceptable salts, solvates, tautomers and isomers thereof, wherein Q⁴ is hydrogen or Q¹, Q³ is selected from hydrogen, halogen, —OH, —NH₂, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, X, R₁, R₃, R₃', R₄, R₄', R₅, R₅', R₆ and R₆' are as defined elsewhere herein.

In certain embodiment, provided herein are compounds of Formula XIIId

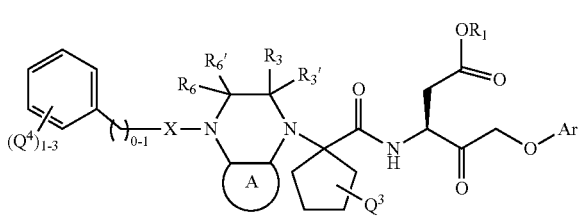

XIIId or pharmaceutically acceptable salts, solvates, tautomers and isomers thereof, wherein $Q^4$ is hydrogen or $Q^1$, $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, X, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula XIV-1

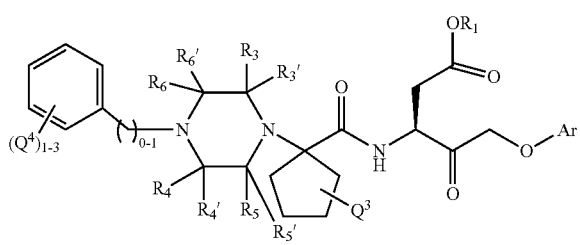

XIV-1 or pharmaceutically acceptable salts, solvates, tautomers and isomers thereof, wherein $Q^4$ is hydrogen or $Q^1$, $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula XIVa-1

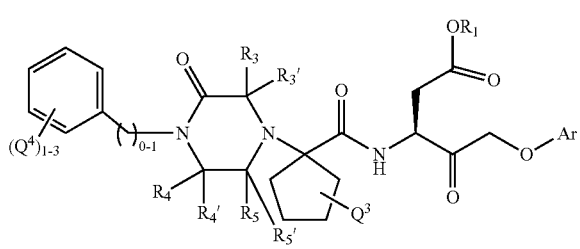

XIVa-1 or pharmaceutically acceptable salts, solvates, tautomers and isomers thereof, wherein $Q^4$ is hydrogen or $Q^1$, $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula XIVb-1

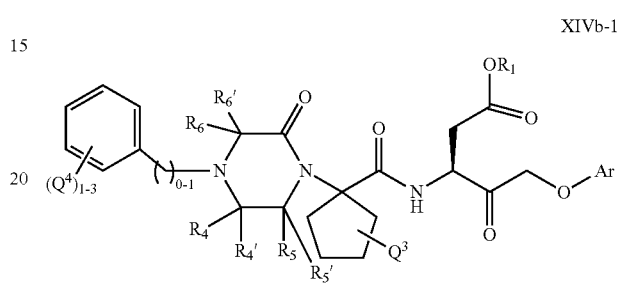

XIVb-1 or pharmaceutically acceptable salts, solvates, tautomers and isomers thereof, wherein $Q^4$ is hydrogen or $Q^1$, $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula XIVc-1

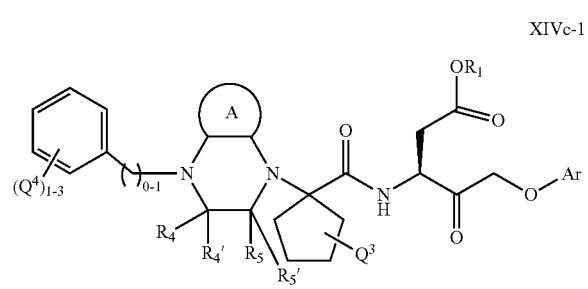

XIVc-1 or pharmaceutically acceptable salts, solvates, tautomers and isomers thereof, wherein $Q^4$ is hydrogen or $Q^1$, $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula XIVd-1

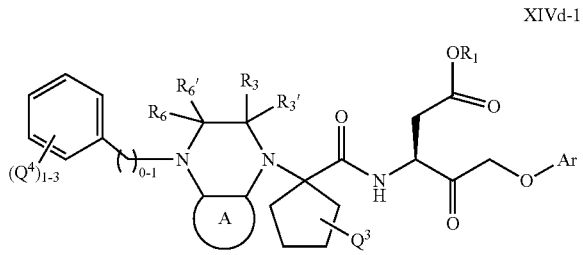

XIVd-1 or pharmaceutically acceptable salts, solvates, tautomers and isomers thereof, wherein $Q^4$ is hydrogen or $Q^1$, $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, Z, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula XIV-3

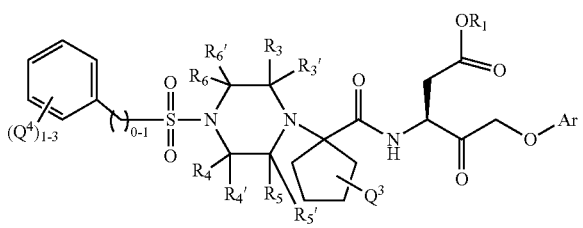

XIV-3 or pharmaceutically acceptable salts, solvates, tautomers and isomers thereof, wherein $Q^4$ is hydrogen or $Q^1$, $Q^3$ is selected from halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula XIVa-3

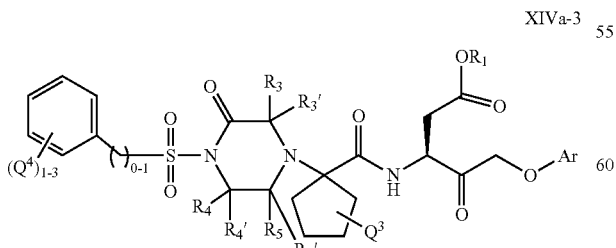

XIVa-3 or pharmaceutically acceptable salts, solvates, tautomers and isomers thereof, wherein $Q^4$ is hydrogen or $Q^1$, $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula XIVb-3

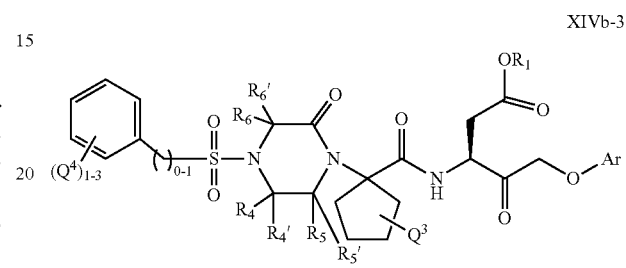

XIVb-3 or pharmaceutically acceptable salts, solvates, tautomers and isomers thereof, wherein $Q^4$ is hydrogen or $Q^1$, $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula XIVc-2

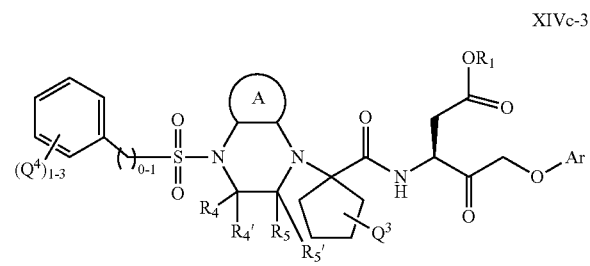

XIVc-3 or pharmaceutically acceptable salts, solvates, tautomers and isomers thereof, wherein $Q^4$ is hydrogen or $Q^1$, $Q^3$ is selected from hydrogen, halogen, —OH, —NH$_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

Ar, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula XIVd-3

XIVd-3

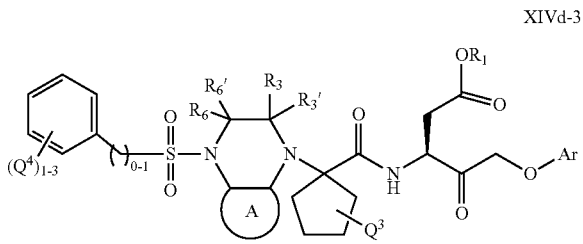

or pharmaceutically acceptable salts, solvates, tautomers and isomers thereof,
wherein $Q^4$ is hydrogen or $Q^1$,
$Q^3$ is selected from hydrogen, halogen, —OH, —$NH_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;
Ar, $R_1$, $R_3$, $R_{3'}$, $R_4$, $R_{4'}$, $R_5$, $R_{5'}$, $R_6$ and $R_{6'}$ are as defined elsewhere herein.

In certain embodiment, provided herein are compounds of Formula XV

XV

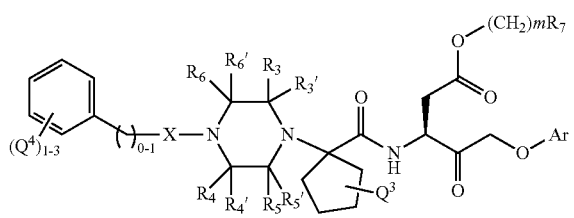

or pharmaceutically acceptable salts, solvates, tautomers and isomers thereof,
wherein
$Q^4$ is hydrogen or $Q^1$,
$R_7$ is hydrogen or optionally substituted phenyl, wherein the substituents when present are selected from 1 to 4 groups $Q^1$;
m is 0-6;
$Q^3$ is hydrogen, halogen, —OH, —$NH_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and
Ar, Z, X, $R_1$, $R_3$, $R_{3'}$, $R_4$, $R_{4'}$, $R_5$, $R_{5'}$, $R_6$, $R_{6'}$ and $Q^1$ are as defined elsewhere herein.

In certain embodiment, provided herein are compounds of Formula XVa

XVa

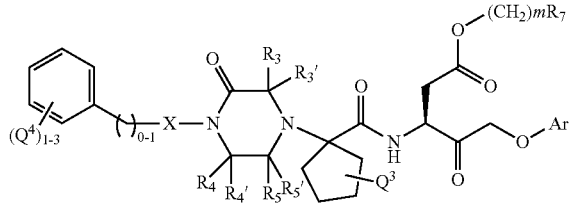

or pharmaceutically acceptable salts, solvates, tautomers and isomers thereof,
wherein
$Q^4$ is hydrogen or $Q^1$,
$R_7$ is hydrogen or optionally substituted phenyl, wherein the substituents when present are selected from 1 to 4 groups $Q^1$;
m is 0-6;
$Q^3$ is hydrogen, halogen, —OH, —$NH_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and
Ar, Z, X, $R_3$, $R_{3'}$, $R_4$, $R_{4'}$, $R_5$, $R_{5'}$, and $Q^1$ are as defined elsewhere herein.

In certain embodiment, provided herein are compounds of Formula XVb

XVb

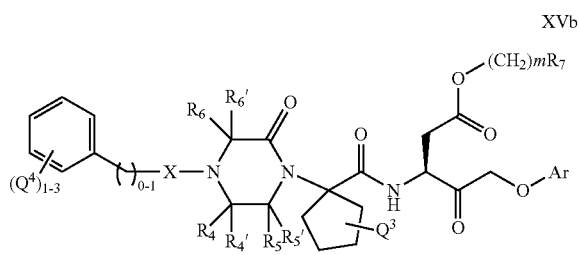

or pharmaceutically acceptable salts, solvates, tautomers and isomers thereof,
wherein
$Q^4$ is hydrogen or $Q^1$,
$R_7$ is hydrogen or optionally substituted phenyl, wherein the substituents when present are selected from 1 to 4 groups $Q^1$;
m is 0-6;
$Q^3$ is hydrogen, halogen, —OH, —$NH_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and
Ar, Z, X, $R_4$, $R_{4'}$, $R_5$, $R_{5'}$, $R_6$, $R_{6'}$ and $Q^1$ are as defined elsewhere herein.

In certain embodiment, provided herein are compounds of Formula XVc

XVc

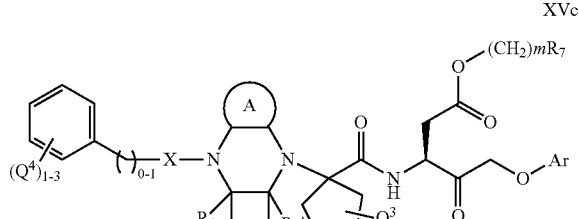

or pharmaceutically acceptable salts, solvates, tautomers and isomers thereof,
wherein
$Q^4$ is hydrogen or $Q^1$,
$R_7$ is hydrogen or optionally substituted phenyl, wherein the substituents when present are selected from 1 to 4 groups $Q^1$;

m is 0-6;

Q³ is hydrogen, halogen, —OH, —NH₂, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, X, R₄, R₄', R₅, R₅', ring A and Q¹ are as defined elsewhere herein.

In certain embodiment, provided herein are compounds of Formula XVd

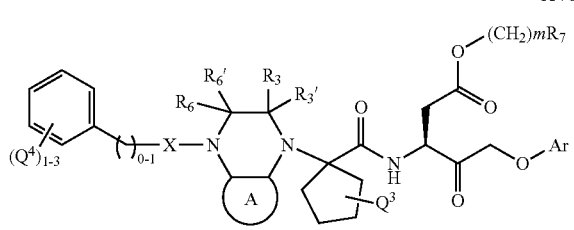

XVd or pharmaceutically acceptable salts, solvates, tautomers and isomers thereof, wherein Q⁴ is hydrogen or Q¹, R₇ is hydrogen or optionally substituted phenyl, wherein the substituents when present are selected from 1 to 4 groups Q¹;

m is 0-6;

Q³ is hydrogen, halogen, —OH, —NH₂, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, X, R₃, R₃', R₆, R₆', ring A and Q¹ are as defined elsewhere herein.

In certain embodiment, provided herein are compounds of Formula XVI

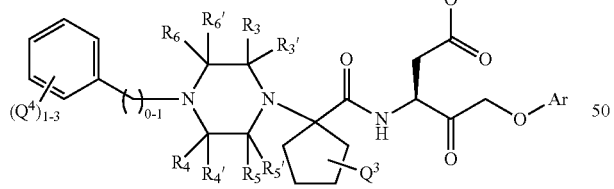

XVI or pharmaceutically acceptable salts, solvates, tautomers and isomers thereof, wherein Q⁴ is hydrogen or Q¹, R₇ is hydrogen or optionally substituted phenyl, wherein the substituents when present are selected from 1 to 4 groups Q¹;

m is 0-6;

Q³ is hydrogen, halogen, —OH, —NH₂, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, R₃, R₃', R₄, R₄', R₅, R₅', R₆, R₆' and Q¹ are as defined elsewhere herein.

In certain embodiment, provided herein are compounds of Formula XVIa

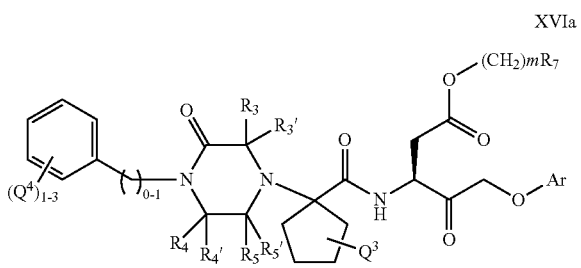

XVIa or pharmaceutically acceptable salts, solvates, tautomers and isomers thereof, wherein Q⁴ is hydrogen or Q¹, R₇ is hydrogen or optionally substituted phenyl, wherein the substituents when present are selected from 1 to 4 groups Q¹;

m is 0-6;

Q³ is hydrogen, halogen, —OH, —NH₂, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, R₃, R₃', R₄, R₄', R₅, R₅', and Q¹ are as defined elsewhere herein.

In certain embodiment, provided herein are compounds of Formula XVIb

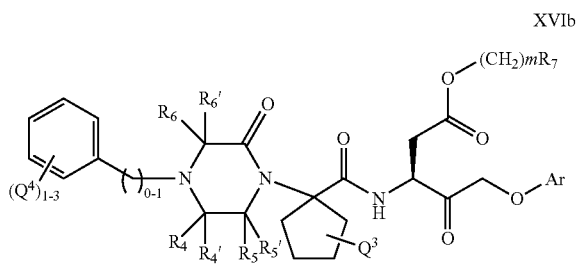

XVIb or pharmaceutically acceptable salts, solvates, tautomers and isomers thereof, wherein Q⁴ is hydrogen or Q¹, R₇ is hydrogen or optionally substituted phenyl, wherein the substituents when present are selected from 1 to 4 groups Q¹;

m is 0-6;

Q³ is hydrogen, halogen, —OH, —NH₂, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and Ar, Z, R₄, R₄', R₅, R₅', R₆, R₆' and Q¹ are as defined elsewhere herein.

In certain embodiment, provided herein are compounds of Formula XVIc

XVIc

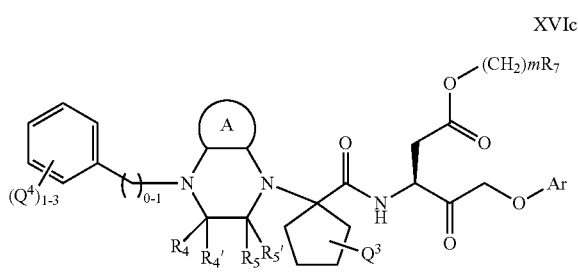

or pharmaceutically acceptable salts, solvates, tautomers and isomers thereof,
wherein
$Q^4$ is hydrogen or $Q^1$,
$R_7$ is hydrogen or optionally substituted phenyl, wherein the substituents when present are selected from 1 to 4 groups $Q^1$;
m is 0-6;
$Q^3$ is hydrogen, halogen, —OH, —$NH_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and
Ar, Z, $R_4$, $R_{4'}$, $R_5$, $R_{5'}$, ring A and $Q^1$ are as defined elsewhere herein.

In certain embodiment, provided herein are compounds of Formula XVId

XVId

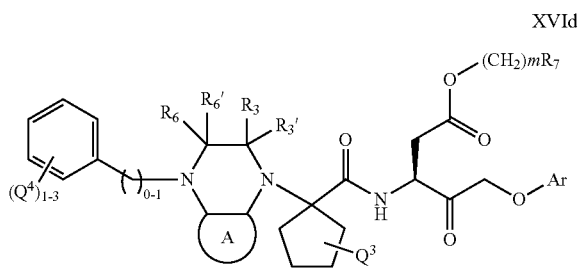

or pharmaceutically acceptable salts, solvates, tautomers and isomers thereof,
wherein
$Q^4$ is hydrogen or $Q^1$,
$R_7$ is hydrogen or optionally substituted phenyl, wherein the substituents when present are selected from 1 to 4 groups $Q^1$;
m is 0-6;
$Q^3$ is hydrogen, halogen, —OH, —$NH_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino; and
Ar, Z, $R_3$, $R_{3'}$, $R_6$, $R_{6'}$, ring A and $Q^1$ are as defined elsewhere herein.

In some embodiments, in the compounds of Formula I, Ia, Ib, Ic, Id, II-1, IIa-1, IIb-1, IIc-1, IId-1, II-2, IIa-2, IIb-2, IIc-2, IId-2, II-3, IIa-3, IIb-3, IIc-3, IId-3, III, IIIa, IIIb, IIIc, IIId, IV, IVa, IVb, IVc, IVd, V, Va, Vb, Vc, Vd, VI-1, VIa-1, VIb-1, VIc-1, VId-1, VI-2, VIa-2, VIb-2, VIc-2, VId-2, VI-3, VIa-3, VIb-3, VIc-3, VId-3, VII, VIIa, VIIb, VIIc, VIId, VIII, VIIIa, VIIIb, VIIIc, VIIId, IX, IXa, IXb, IXc, IXd, X-1, Xa-1, Xb-1, Xc-1, Xd-1, X-3, Xa-3, Xb-3, Xc-3, Xd-3, XI, XIa, XIb, XIc, XId, XII, XIIa, XIIb, XIIc, XIId, XIII, XIIIa, XIIIb, XIIIc, XIIId, XIV-1, XIVa-1, XIVb-1, XIVc-1, XIVd-1, XIV-3, XIVa-3, XIVb-3, XIVc-3, XIVd-3, XV, XVa, XVb, XVc, XVd, XVI, XVIa, XVIb, XVIc and XVId, where substituent Q is present, it is selected from one to four halo, alkyl and haloakyl.

In some embodiments, in the compounds of Formula I, Ia, Ib, Ic, Id, II-1, IIa-1, IIb-1, IIc-1, IId-1, II-2, IIa-2, IIb-2, IIc-2, IId-2, II-3, IIa-3, IIb-3, IIc-3, IId-3, III, IIIa, IIIb, IIIc, IIId, IV, IVa, IVb, IVc, IVd, V, Va, Vb, Vc, Vd, VI-1, VIa-1, VIb-1, VIc-1, VId-1, VI-2, VIa-2, VIb-2, VIc-2, VId-2, VI-3, VIa-3, VIb-3, VIc-3, VId-3, VII, VIIa, VIIb, VIIc, VIId, VIII, VIIIa, VIIIb, VIIIc, VIIId, IX, IXa, IXb, IXc, IXd, X-1, Xa-1, Xb-1, Xc-1, Xd-1, X-3, Xa-3, Xb-3, Xc-3, Xd-3, XI, XIa, XIb, XIc, XId, XII, XIIa, XIIb, XIIc, XIId, XIII, XIIIa, XIIIb, XIIIc, XIIId, XIV-1, XIVa-1, XIVb-1, XIVc-1, XIVd-1, XIV-3, XIVa-3, XIVb-3, XIVc-3, XIVd-3, XV, XVa, XVb, XVc, XVd, XVI, XVIa, XVIb, XVIc and XVId, where substituent $Q^1$ is present, it is selected from one to four halo, alkyl and haloakyl.

In some embodiments, in the compounds of Formula I, Ia, Ib, Ic, Id, II-1, IIa-1, IIb-1, IIc-1, IId-1, II-2, IIa-2, IIb-2, IIc-2, IId-2, II-3, IIa-3, IIb-3, IIc-3, IId-3, III, IIIa, IIIb, IIIc, IIId, IV, IVa, IVb, IVc, IVd, V, Va, Vb, Vc, Vd, VI-1, VIa-1, VIb-1, VIc-1, VId-1, VI-2, VIa-2, VIb-2, VIc-2, VId-2, VI-3, VIa-3, VIb-3, VIc-3, VId-3, VII, VIIa, VIIb, VIIc, VIId, VIII, VIIIa, VIIIb, VIIIc, VIIId, IX, IXa, IXb, IXc, IXd, X-1, Xa-1, Xb-1, Xc-1, Xd-1, X-3, Xa-3, Xb-3, Xc-3, Xd-3, XI, XIa, XIb, XIc, XId, XII, XIIa, XIIb, XIIc, XIId, XIII, XIIIa, XIIIb, XIIIc, XIIId, XIV-1, XIVa-1, XIVb-1, XIVc-1, XIVd-1, XIV-3, XIVa-3, XIVb-3, XIVc-3, XIVd-3, XV, XVa, XVb, XVc, XVd, XVI, XVIa, XVIb, XVIc and XVId, where substituent $Q^3$ is present, it is selected from one to four halo, alkyl and haloakyl.

In some embodiments, in the compounds of Formula I, Ia, Ib, Ic, Id, II-1, IIa-1, IIb-1, IIc-1, IId-1, II-2, IIa-2, IIb-2, IIc-2, IId-2, II-3, IIa-3, IIb-3, IIc-3, IId-3, III, IIIa, IIIb, IIIc, IIId, IV, IVa, IVb, IVc, IVd, V, Va, Vb, Vc, Vd, VI-1, VIa-1, VIb-1, VIc-1, VId-1, VI-2, VIa-2, VIb-2, VIc-2, VId-2, VI-3, VIa-3, VIb-3, VIc-3, VId-3, VII, VIIa, VIIb, VIIc, VIId, VIII, VIIIa, VIIIb, VIIIc, VIIId, IX, IXa, IXb, IXc, IXd, X-1, Xa-1, Xb-1, Xc-1, Xd-1, X-3, Xa-3, Xb-3, Xc-3, Xd-3, XI, XIa, XIb, XIc, XId, XII, XIIa, XIIb, XIIc, XIId, XIII, XIIIa, XIIIb, XIIIc, XIIId, XIV-1, XIVa-1, XIVb-1, XIVc-1, XIVd-1, XIV-3, XIVa-3, XIVb-3, XIVc-3, XIVd-3, XV, XVa, XVb, XVc, XVd, XVI, XVIa, XVIb, XVIc and XVId, where substituent $Q^4$ is present, it is selected from one to four halo, alkyl and haloakyl.

In some embodiments, with respect to the "Ar" group in any of the compounds of Formula I, Ia, Ib, Ic, Id, II-1, IIa-1, IIb-1, IIc-1, IId-1, II-2, IIa-2, IIb-2, IIc-2, IId-2, II-3, IIa-3, IIb-3, IIc-3, IId-3, III, IIIa, IIIb, IIIc, IIId, IV, IVa, IVb, IVc, IVd, V, Va, Vb, Vc, Vd, VI-1, VIa-1, VIb-1, VIc-1, VId-1, VI-2, VIa-2, VIb-2, VIc-2, VId-2, VI-3, VIa-3, VIb-3, VIc-3, VId-3, VII, VIIa, VIIb, VIIc, VIId, VIII, VIIIa, VIIIb, VIIIc, VIIId, IX, IXa, IXb, IXc, IXd, X-1, Xa-1, Xb-1, Xc-1, Xd-1, X-3, Xa-3, Xb-3, Xc-3, Xd-3, XI, XIa, XIb, XIc, XId, XII, XIIa, XIIb, XIIc, XIId, XIII, XIIIa, XIIIb, XIIIc, XIIId, XIV-1, XIVa-1, XIVb-1, XIVc-1, XIVd-1, XIV-3, XIVa-3, XIVb-3, XIVc-3, XIVd-3, XV, XVa, XVb, XVc, XVd, XVI, XVIa, XVIb, XVIc and XVId, including in further embodiments of each of these compounds as described above, Ar is phenyl or substituted phenyl, where the substituents are selected from one to four halo or haloalkyl. In some embodiments, Ar is substituted phenyl and includes a mono-, di-, tri- or tetra(halo)phenyl group such as 2-, 3- or 4-chlorophenyl, 2,6-dichlorophenyl, 2,5-dichlorophenyl, 3,4-dichlorophenyl, 2,3,5-trichlorophenyl, 2,3,5,6-tetrachlorophenyl, 2-, 3- or 4-bromophenyl, 2,6-dibromophenyl, 2,5-dibromophenyl, 3,4-dibromophenyl, 2,3,5-tribromophenyl, 2,3,5,6-tetrabromophenyl, 2-, 3- or 4-fluorophenyl, 2,6-difluorophenyl, 2,5-difluorophenyl, 3,4-difluorophenyl, 2,3,5-trifluorophenyl, 2,3,5,6-tetrafluorophenyl or 3-chloro-4-fluorophenyl. In certain embodiments, the substituted phenyl is 2,3,5,6-tetrafluorophenyl. In other embodiments, the substituted phenyl is 3-trifluoromethylphenyl, 2,6 difluoro-4-trifluoromethylphenyl or 5-trifluoromethylphenyl. In certain embodiments, the substituted phenyl is a bis(trifluoromethyl)phenyl. In one embodiment, the substituted phenyl is 3,5-bis(trifluoromethyl)phenyl.

In additional embodiments, Ar is substituted pyridyl, substituted pyridazyl, substituted pyrimidyl or substituted pyrazinyl. In some embodiments, substitution is with a mono-, di- or tri-haloalkyl group. In certain embodiments, substitution is with a tri-haloalkyl group. In further embodiments, the substituent is trifluoroalkyl, such as trifluoromethyl. In some embodiments, Ar is substituted pyrimidyl and the substituent is trifluoromethyl at the 2, 4 or 5 positions. In one embodiment, Ar is substituted pyrimidyl and the substituent is trifluoromethyl at the 2 position.

In some embodiments, in the compounds of Formula I, Ia, Ib, Ic, Id, III, IIIa, IIIb, IIIc, IIId, V, Va, Vb, Vc, Vd, VII, VIIa, VIIb, VIIc, VIId, IX, IXa, IXb, IXc, IXd, XI, XIa, XIb, XIc, XId, XIII, XIIIa, XIIIb, XIIIc, XIIId, XV, XVa, XVb, XVc, and XVd, variable X is CO, and Z is phenyl, and the remainder of the variables are as described herein.

In some embodiments, with respect to the "Z—X" group in any of the compounds of Formula I, Ia, Ib, Ic, Id, III, IIIa, IIIb, IIIc, IIId, V, Va, Vb, Vc, Vd, VII, VIIa, VIIb, VIIc, and VIId, including in further embodiments of each of these compounds as described above, Z—X is selected from among:
3-chlorobenzyl, 3-(tert-butyl)benzyl, 3,5-difluorobenzyl, 5-fluoro-(1,1'-biphenyl)-3-ylmethyl, 4-(naphthalen-2-yl)methyl, 5-(phenylpyridin-3-yl)methyl, 1H-pyrrolo[2,3-b]pyridin-5-yl)methyl, 3,5-difluorobenzyl, 5-fluoro-[1,1'-biphenyl]-3-yl)methyl, 4-(naphthalen-2-yl)methyl, 5-(phenylpyridin-3-yl)methyl, 6-(methylpyridin-2-yl) methyl, 4-(thiophen-2-yl)methyl, 5-(trifluoromethyl)furan-2-yl)methyl, 6-(bromofuro[3,2-b]pyridin-2-yl)methyl, 6-(chloropyridin-3-yl)methyl, 3-methoxybenzyl, 4-methoxybenzyl, 4-chlorobenzyl, 3-phenoxybenzyl, 4-carboxybenzyl, 3-carboxybenzyl, 2-acetamidobenzyl, 2,4-(bis-trifluromethyl)benzyl, 3-methylbenzyl, 2,4,5-trifluorobenzyl, 3-(trifluoromethyl)benzyl, 6-(chloropyridin-3-yl) methyl, 4-(pyrimidin-2-yl)methyl, 4-benzylsulfonyl, 2,6-(difluorophenyl)sulfonyl, 4-phenylsulfonyl, 4-(chlorophenyl)sulfonyl, 4-(thiophen-2-yl)sulfonyl, 4-cyclohexylsulfonyl, 2,6-(difluorophenyl)sulfonyl, 4-(chlorophenyl)sulfonyl, 4-(phenylsulfonyl), 4-(thiophen-2-yl)sulfonyl, 4-phenylsulfonyl, 4-benzyl.

In some embodiments, with respect to the "Z—X" group in any of the compounds of Formula I, Ia, Ib, Ic, Id, III, IIIa, IIIb, IIIc, IIId, V, Va, Vb, Vc, Vd, VII, VIIa, VIIb, VIIc, and VIId, including in further embodiments of each of these compounds as described above, Z—X is selected from among:
3-chlorobenzyl, 3-(tert-butyl)benzyl, 3,5-difluorobenzyl, 5-fluoro-(1,1'-biphenyl)-3-ylmethyl, 4-(naphthalen-2-yl)methyl, 5-(phenylpyridin-3-yl)methyl, 1H-pyrrolo[2,3-b]pyridin-5-yl)methyl, 3,5-difluorobenzyl, 5-fluoro-[1,1'-biphenyl]-3-yl)methyl, 4-(naphthalen-2-yl)methyl, 5-(phenylpyridin-3-yl)methyl, 6-(methylpyridin-2-yl) methyl, 4-(thiophen-2-yl)methyl, 5-(trifluoromethyl)furan-2-yl)methyl, 6-(bromofuro[3,2-b]pyridin-2-yl)methyl, 6-(chloropyridin-3-yl)methyl, 3-methoxybenzyl, 4-methoxybenzyl, 4-chlorobenzyl, 3-phenoxybenzyl, 4-carboxybenzyl, 3-carboxybenzyl, 2-acetamidobenzyl, 2,4-(bis-trifluromethyl)benzyl, 3-methylbenzyl, 2,4,5-trifluorobenzyl, 3-(trifluoromethyl)benzyl, 6-(chloropyridin-3-yl) methyl, 4-(pyrimidin-2-yl)methyl, 4-benzylsulfonyl, 2,6-(difluorophenyl)sulfonyl, 4-phenylsulfonyl, 4-(chlorophenyl)sulfonyl, 4-(thiophen-2-yl)sulfonyl, 4-cyclohexylsulfonyl, 2,6-(difluorophenyl)sulfonyl, 4-(chlorophenyl)sulfonyl, 4-(phenylsulfonyl), 4-(thiophen-2-yl)sulfonyl, 4-phenylsulfonyl, 4-benzyl or 4-benzoyl.

In certain embodiments, the caspase inhibitor compound provided herein is selected from among:
(S)-3-(2-(4-(3-chlorobenzyl)-3-oxopiperazin-1-yl)acetamido)-4-oxo-5-(2,3,5,6-tetrafluorophenoxy)pentanoic acid
(S)-3-(2-(4-(3-(tert-butyl)benzyl)-3-oxopiperazin-1-yl)acetamido)-4-oxo-5-(2,3,5,6-tetrafluorophenoxy)pentanoic acid
(S)-3-(2-(4-(3,5-difluorobenzyl)-3-oxopiperazin-1-yl)acetamido)-4-oxo-5-(2,3,5,6-tetrafluorophenoxy)pentanoic acid
(S)-3-(2-(4-((5-fluoro-[1,1'-biphenyl]-3-yl)methyl)-3-oxopiperazin-1-yl)acetamido)-4-oxo-5-(2,3,5,6-tetrafluorophenoxy)pentanoic acid
(S)-3-(2-(4-(naphthalen-2-ylmethyl)-3-oxopiperazin-1-yl)acetamido)-4-oxo-5-(2,3,5,6-tetrafluorophenoxy)pentanoic acid
(S)-4-oxo-3-(2-(3-oxo-4-((5-phenylpyridin-3-yl)methyl)piperazin-1-yl)acetamido)-5-(2,3,5,6-tetrafluorophenoxy)pentanoic acid
(S)-3-((S)-2-(4-benzyl-3-oxopiperazin-1-yl)propanamido)-4-oxo-5-(2,3,5,6-tetrafluorophenoxy)pentanoic acid
(S)-3-(2-(4-benzyl-3-oxopiperazin-1-yl)-2-methylpropanamido)-4-oxo-5-(2,3,5,6-tetrafluorophenoxy)pentanoic acid
(S)-3-(1-(4-(3-chlorobenzyl)-3-oxopiperazin-1-yl)cyclopentane-1-carboxamido)-4-oxo-5-(2,3,5,6-tetrafluorophenoxy)pentanoic acid
(3S)-4-oxo-3-(2-(3-oxo-4-((5-phenylpyridin-3-yl)methyl)piperazin-1-yl)propanamido)-5-(2,3,5,6-tetrafluorophenoxy)pentanoic acid
(S)-3-(2-(4-((1H-pyrrolo[2,3-b]pyridin-5-yl)methyl)-3-oxopiperazin-1-yl)acetamido)-4-oxo-5-(2,3,5,6-tetrafluorophenoxy)pentanoic acid
(S)-3-(2-(4-((3,3-dimethyl-2-oxo-2,3-dihydro-1H-pyrrolo[2,3-b]pyridin-5-yl)methyl)-3-oxopiperazin-1-yl)acetamido)-4-oxo-5-(2,3,5,6-tetrafluorophenoxy)pentanoic acid
(S)-3-(2-(4-(3-chlorobenzyl)-2-oxopiperazin-1-yl)acetamido)-4-oxo-5-(2,3,5,6-tetrafluorophenoxy)pentanoic acid
(S)-3-(2-(4-(3-(tert-butyl)benzyl)-2-oxopiperazin-1-yl)acetamido)-4-oxo-5-(2,3,5,6-tetrafluorophenoxy)pentanoic acid
(3S)-3-(2-(4-(3,5-difluorobenzyl)-2-methyl-3-oxopiperazin-1-yl)acetamido)-4-oxo-5-(2,3,5,6-tetrafluorophenoxy)pentanoic acid
(3S)-3-(2-(4-((5-fluoro-[1,1'-biphenyl]-3-yl)methyl)-3-methyl-2-oxopiperazin-1-yl)acetamido)-4-oxo-5-(2,3,5,6-tetrafluorophenoxy)pentanoic acid
(S)-3-(2-(4-(naphthalen-2-ylmethyl)-2-oxopiperazin-1-yl)acetamido)-4-oxo-5-(2,3,5,6-tetrafluorophenoxy)pentanoic acid
(S)-4-oxo-3-(2-(2-oxo-4-((5-phenylpyridin-3-yl)methyl)piperazin-1-yl)acetamido)-5-(2,3,5,6-tetrafluorophenoxy)pentanoic acid (S)-3-(2-(4-((6-methylpyridin-2-yl)methyl)-2-oxopiperazin-1-yl)acetamido)-4-oxo-5-(2,3,5,6-tetrafluorophenoxy)pentanoic acid (S)-4-oxo-3-(2-(3-oxo-4-(thiophen-2-ylmethyl)piperazin-1-yl)acetamido)-5-(2,3,5,6-tetrafluorophenoxy)pentanoic acid (S)-4-oxo-3-(2-(3-oxo-4-((5-(trifluoromethyl)furan-2-yl)methyl)piperazin-1-yl)acetamido)-5-(2,3,5,6-tetrafluorophenoxy)pentanoic acid (S)-3-(2-(4-((6-bromofuro[3,2-b]pyridin-2-yl)methyl)-3-oxopiperazin-1-yl)acetamido)-4-oxo-5-(2,3,5,6-tetrafluorophenoxy)pentanoic acid (S)-3-(2-(4-((6-chloropyridin-3-yl)methyl)-2-oxopiperazin-1-yl)acetamido)-4-oxo-5-(2,3,5,6-tetrafluorophenoxy)pentanoic acid (S)-4-oxo-3-(2-(3-oxo-4-(pyrimidin-2-ylmethyl)piperazin-1-yl)acetamido)-5-(2,3,5,6-tetrafluorophenoxy)pentanoic acid (S)-3-(2-(4-(3-methoxybenzyl)-3-oxopiperazin-1-yl)acetamido)-4-oxo-5-(2,3,5,6-tetrafluorophenoxy)pentanoic acid (S)-3-(2-(4-(3-methylbenzyl)-2-oxopiperazin-1-yl)acetamido)-4-oxo-5-(2,3,5,6-tetrafluorophenoxy)pentanoic acid (S)-4-oxo-3-(2-(3-oxo-4-(2,4,5-trifluorobenzyl)piperazin-1-yl)acetamido)-5-(2,3,5,6-tetrafluorophenoxy)pentanoic acid (S)-4-oxo-3-(2-(2-oxo-4-(3-(trifluoromethyl)benzyl)piperazin-1-yl)acetamido)-5-(2,3,5,6-tetrafluorophenoxy)pentanoic acid (S)-3-(2-(4-((6-chloropyridin-3-yl)methyl)-3-oxopiperazin-1-yl)acetamido)-4-oxo-5-(2,3,5,6-tetrafluorophenoxy)pentanoic acid (S)-4-oxo-3-(2-(3-oxo-4-(pyrimidin-2-ylmethyl)piperazin-1-yl)acetamido)-5-(2,3,5,6-tetrafluorophenoxy)pentanoic acid (S)-3-(2-(4-(benzyl sulfonyl)-2-oxopiperazin-1-yl)acetamido)-4-oxo-5-(2,3,5,6-tetrafluorophenoxy)pentanoic acid (S)-3-(2-(4-((2,6-difluorophenyl)sulfonyl)-2-oxopiperazin-1-yl)acetamido)-4-oxo-5-(2,3,5,6-tetrafluorophenoxy)pentanoic acid (S)-4-oxo-3-(2-(4-(phenylsulfonyl)piperazin-1-yl)acetamido)-5-(2,3,5,6-tetrafluorophenoxy)pentanoic acid (S)-4-oxo-3-((S)-2-(4-(phenyl sulfonyl)piperazin-1-yl)propanamido)-5-(2,3,5,6-tetrafluorophenoxy)pentanoic acid (S)-3-(2-(4-((4-chlorophenyl)sulfonyl)-2-oxopiperazin-1-yl)acetamido)-4-oxo-5-(2,3,5,6-tetrafluorophenoxy)pentanoic acid (S)-4-oxo-3-(2-(2-oxo-4-(thiophen-2-yl sulfonyl)piperazin-1-yl)acetamido)-5-(2,3,5,6-tetrafluorophenoxy)pentanoic acid (S)-3-(2-(4-(cyclohexylsulfonyl)-2-oxopiperazin-1-yl)acetamido)-4-oxo-5-(2,3,5,6-tetrafluorophenoxy)pentanoic acid (S)-3-(2-(4-((2,6-difluorophenyl)sulfonyl)piperazin-1-yl)acetamido)-4-oxo-5-(2,3,5,6-tetrafluorophenoxy)pentanoic acid (S)-3-(2-(4-((4-chlorophenyl)sulfonyl)piperazin-1-yl)acetamido)-4-oxo-5-(2,3,5,6-tetrafluorophenoxy)pentanoic acid (S)-4-oxo-3-(2-(4-(phenylsulfonyl)piperazin-1-yl)acetamido)-5-(2,3,5,6-tetrafluorophenoxy)pentanoic acid (S)-4-oxo-5-(2,3,5,6-tetrafluorophenoxy)-3-(2-(4-(thiophen-2-ylsulfonyl)piperazin-1-yl)acetamido)pentanoic acid (S)-3-(2-(4-(cyclohexylsulfonyl)piperazin-1-yl)acetamido)-4-oxo-5-(2,3,5,6-tetrafluorophenoxy)pentanoic acid (S)-4-oxo-3-(2-(4-(phenylsulfonyl)piperazin-1-yl)acetamido)-5-((2-(trifluoromethyl)pyrimidin-4-yl)oxy)pentanoic acid (S)-4-oxo-3-(2-(4-(phenylsulfonyl)piperazin-1-yl)acetamido)-5-((2-(trifluoromethyl)pyrimidin-4-yl)oxy)pentanoic acid (S)-3-(2-(4-benzyl-3-oxopiperazin-1-yl)acetamido)-4-oxo-5-((2-(trifluoromethyl)pyrimidin-4-yl)oxy)pentanoic acid (S)-3-(2-(4-benzyl-3-oxopiperazin-1-yl)acetamido)-5-(3,5-bis(trifluoromethyl)phenoxy)-4-oxopentanoic acid (S)-5-(3,5-bis(trifluoromethyl)phenoxy)-4-oxo-3-(2-(4-(phenylsulfonyl)piperazin-1-yl)acetamido)pentanoic acid (S)-3-(2-(4-benzyl-2-oxopiperazin-1-yl)acetamido)-5-(3,5-bis(trifluoromethyl)phenoxy)-4-oxopentanoic acid (S)-3-(2-(4-benzyl-2,3-dioxopiperazin-1-yl)acetamido)-5-(3,5-bis(trifluoromethyl)phenoxy)-4-oxopentanoic acid (S)-3-(2-(4-benzyl-2,5-dioxopiperazin-1-yl)acetamido)-5-(3,5-bis(trifluoromethyl)phenoxy)-4-oxopentanoic acid (S)-5-(3,5-bis(trifluoromethyl)phenoxy)-4-oxo-3-(2-(2-oxo-4-(phenylsulfonyl)piperazin-1-yl)acetamido)pentanoic acid (S)-3-(2-(4-benzyl-2-oxo-3,4-dihydroquinoxalin-1(2H)-yl)acetamido)-5-(3,5-bis(trifluoromethyl)phenoxy)-4-oxopentanoic acid (S)-3-(2-(4-benzyl-2-oxo-3,4-dihydroquinoxalin-1(2H)-yl)acetamido)-4-oxo-5-(2,3,5,6-tetrafluorophenoxy)pentanoic acid (S)-3-(2-(4-benzyl-2,3-dioxo-3,4-dihydroquinoxalin-1(2H)-yl)acetamido)-4-oxo-5-(2,3,5,6-tetrafluorophenoxy)pentanoic acid, (S)-3-(2-(4-benzyl-2,3-dioxopiperazin-1-yl)acetamido)-4-oxo-5-(2,3,5,6-tetrafluorophenoxy)pentanoic acid, (S)-3-(2-(4-benzoyl-2-oxopiperazin-1-yl)acetamido)-4-oxo-5-(2,3,5,6-tetrafluorophenoxy)pentanoic acid, (S)-3-(2-(4-benzyl-2-oxopiperazin-1-yl)acetamido)-5-(3,5-bis(trifluoromethyl)phenoxy)-4-oxopentanoic acid, (S)-3-(2-(4-benzyl-2,5-dioxopiperazin-1-yl)acetamido)-4-oxo-5-(2,3,5,6-tetrafluorophenoxy)pentanoic acid, (S)-3-(2-(4-benzyl-2-oxo-3,4-dihydroquinoxalin-1(2H)-yl)acetamido)-4-oxo-5-(2,3,5,6-tetrafluorophenoxy)pentanoic acid, (S)-3-(2-((R)-4-benzyl-3-methyl-2-oxopiperazin-1-yl)acetamido)-4-oxo-5-(2,3,5,6-tetrafluorophenoxy)pentanoic acid, and (S)-3-(2-(4-benzoyl-3-oxopiperazin-1-yl)acetamido)-4-oxo-5-(2,3,5,6-tetrafluorophenoxy)pentanoic acid.

4.4. Schematics for the Preparation of Caspase Inhibitor Compounds

Compounds of the present invention can be prepared by the general process outlined in Scheme I.

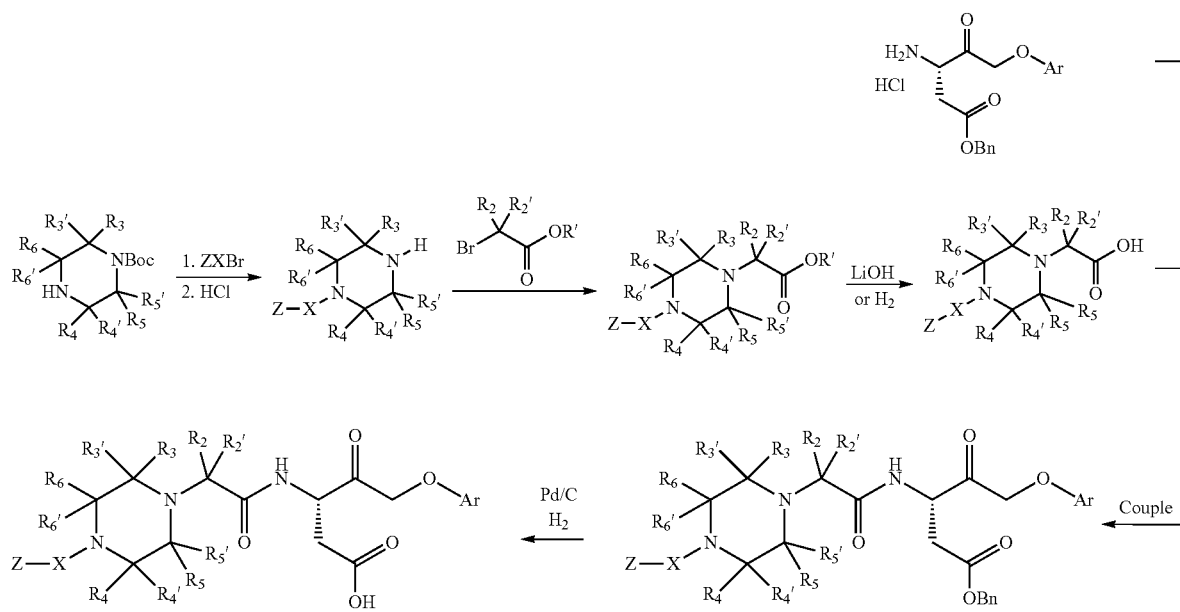

Scheme I

4.5. Methods of Treatment

The caspase inhibitor compounds provided herein can be used in methods for the treatment of conditions that are associated with or modulated by caspases, such as those described in Section 4.2.

The disease states which can be treated or prevented by the compounds and/or their pharmaceutical compositions provided herein include, but are not limited to, liver diseases, gastrointestinal diseases, kidney diseases, lung diseases, dermatological diseases, rheumatological diseases, cardiovascular diseases, inflammatory diseases, autoimmune diseases and CNS diseases, and for inhibiting pathological apoptosis and excessive inflammation.

Provided herein are methods of treatment by administering an effective amount of the compounds and/or pharmaceutical compositions provided herein to mammals, also referred to herein as subjects or patients, in need of such treatment (that is, those suffering from, e.g., liver diseases, gastrointestinal diseases, kidney diseases, lung diseases, dermatological diseases, rheumatological diseases, cardiovascular diseases inflammatory diseases autoimmune diseases and CNS diseases). Also provided herein are compounds for use in the treatment of such diseases.

Inflammatory diseases that can be treated or prevented include chronic and acute diseases such as, for example, autoinflammatory diseases such as Cryopyrin-Associated Periodic Syndromes (CAPS) and neuroinflammatory diseases such as multiple sclerosis (MS), Parkinson's disease and Alzheimer's disease. Treatment of acute inflammatory diseases such as, for example, septic shock, septicemia and adult respiratory distress syndrome also are contemplated by the methods provided herein.

Other target diseases for treatment using the compounds and pharmaceutical compositions provided herein include those associated with ischemic injury, including, for example, myocardial infarction, stroke, and ischemic kidney disease. The compounds and pharmaceutical compositions provided herein also can be used to treat infectious diseases, especially those involved with viral infections.

In certain embodiments, the compounds provided herein can be used in methods for the treatment of chronic liver disease including, NASH, NAFLD, PSC, PBC, alcoholic liver disease and viral liver diseases. In one embodiment, the methods provided herein are for treatment of clinical consequences of chronic liver disease. In one embodiment, the methods are for reducing fibrosis associated with chronic liver disease. In one embodiment, the methods are for reducing fibrosis in patients with liver transplants. In one embodiment, the methods are for reducing portal hypertension associated with chronic liver disease. In another embodiment, the methods are for the reduction of cirrhosis. In certain embodiments, the methods are for treating cirrhosis and/or for further reducing the symptoms associated with cirrhosis. Symptoms of cirrhosis can include, but are not limited to, portal hypertension, abnormal nerve function, ascites (build-up of fluid in the abdominal cavity), breast enlargement in men, coughing up or vomiting blood, curling of fingers (Dupuytren contracture of the palms), gallstones, hair loss, itching, jaundice, kidney failure, liver encephalopathy, muscle loss, poor appetite, redness of palms, salivary gland enlargement in cheeks, shrinking of testes, small spider-like veins in skin, weakness, weight loss, spider angiomas (a central arteriole from which numerous small branching vessels radiate), encephalopathy, and asterixis (flapping tremor).

In one embodiment of a method for treating chronic liver disease, the methods provided herein can lower the elevated level of liver enzyme, such as ALT and AST levels. Methods for measuring the level of elevated liver enzymes are well known in the art (see, e.g., Jeong S. Y. et al. Sandwich ELISA for measurement of cytosolic aspartate aminotransferase in sera from patients with liver diseases, *Clin Chem.*, 2003; 49(5):826 9 and Burin des Roziers N. et al. A microtiter plate assay for measurement of serum alanine aminotransferase in blood donors, *Transfusion.*, 1995; 35(4): 331 4, each of which is incorporated by reference herein in its entirety). In one embodiment, the elevated level of one or more liver enzyme, such as ALT or AST, or the total amount of elevated liver enzyme is reduced by more than about 90% or more than 95%. In one embodiment, the elevated level of one or more liver enzyme, such as elevated levels of ALT or AST, or the total amount of elevated liver enzyme is reduced by at least 95%, at least 90%, at least 80%, at least 70%, at least 60%, at least 50%, at least 40%, at least 30%, at least 20%, at least 10%, at least 5%, at least 2% or at least 1%.

In certain embodiments, provided are methods for treatment of NASH with a combination of current commercially available or experimental treatments for NASH and a caspase inhibitor provided herein. Exemplary compounds and current experimental therapies for treatment of NASH include selonsertib (GS-4997), cenicriviroc, ocaliva (obeticholic acid), elafibranor (GFT505), GS-0976, aramchol, IVA-337 (lanifibranor), saroglitazar, namodenoson (CF102), MN-001 (tipelukast), BI-1467335 (PXS-4782A), volixibat (SHP626), NGM282, GS-9674 (Px-104), LMB-763, LJN-452, semaglutide (NN-9931), IMM-124E, apararenone (MT-3995), MSDC-0602, MGL-3196.

In certain embodiments, provided are methods for treatment of cirrhosis with a combination of current commercially available or experimental treatments for portal hypertension and/or for cirrhosis, and a caspase inhibitor provided herein. Exemplary methods of treatment of portal hypertension are described by Bari, K et al. Treatment of portal hypertension. *World J. Gastroenterology* 2012; 18:1166-1175. and Giannelli, et al. Beta-blockers in liver cirrhosis. *Annal. Gastroenterology* 2014; 27:20-26. incorporated by reference herein in their entirety. Exemplary compounds and current experimental therapies for treatment of portal hypertension include Propranolol ((RS)-1-(1-methylethylamino)-3-(1-naphthyloxy)propan-2-ol), Nadolol ((2R*,3S*)-5-{[(2R*)-3-(tert-butylamino)-2-hydroxypropyl]oxy}-1,2,3,4-tetrahydronaphthalene-2,3-diol), Carvedilol ((±)-[3-(9H-carbazol-4-yloxy)-2-hydroxypropyl][2-(2-methoxyphenoxy)ethyl]amine), Simvastatin and analogs or derivatives thereof as understood by those of skill in the art.

4.6. Formulation of Pharmaceutical Compositions

The pharmaceutical compositions provided herein contain therapeutically effective amounts of one or more of the compounds provided herein that are useful in the prevention, treatment, or amelioration of one or more conditions associated with or modulated by caspases, or one or more symptoms of a condition associated with or modulated by caspases, such as those described in Sections 4.2 and 4.5, and a pharmaceutically acceptable carrier.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds provided herein are formulated into pharmaceutical compositions using techniques and procedures well known in the art (see, e.g., Remington's Pharmaceutical Sciences, 20$^{th}$ eds., Mack Publishing, Easton Pa. (2000)).

In the compositions, effective concentrations of one or more compounds or pharmaceutically acceptable derivatives is (are) mixed with a suitable pharmaceutical carrier or vehicle. The compounds can be derivatized as the corresponding salts, esters, acids, bases, solvates, hydrates or prodrugs prior to formulation, as described above. The concentrations of the compounds in the compositions are effective for delivery of an amount, upon administration, that treats, prevents, or ameliorates a condition or one or more of the symptoms of a condition modulated by one or more caspases as described in Sections 4.2 and 4.5.

In one embodiment, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds can be formulated as the sole pharmaceutically active ingredient in the composition or can be combined with other active ingredients. Liposomal suspensions, including tissue-targeted liposomes, such as tumor-targeted liposomes, can also be suitable as pharmaceutically acceptable carriers. These can be prepared according to methods known to those skilled in the art. For example, liposome formulations can be prepared as known in the art. Briefly, liposomes such as multilamellar vesicles (MLV's) can be formed by drying down egg phosphatidyl choline and brain phosphatidyl serine (7:3 molar ratio) on the inside of a flask. A solution of a compound provided herein in phosphate buffered saline (PBS) lacking divalent cations is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration can be determined empirically by testing the compounds in in vitro and in vivo systems known in the art and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art.

In one embodiment, a therapeutically effective dosage should produce a serum concentration of an active ingredient of from about 0.1 ng/ml to about 50-100 µg/ml, from about 0.5 ng/ml to about 80 µg/ml, from about 1 ng/ml to about 60 µg/ml, from about 5 ng/ml to about 50 µg/ml, from about 5 ng/ml to about 40 µg/ml, from about 10 ng/ml to about 35 µg/ml, from about 10 ng/ml to about 25 µg/ml, from about 10 ng/ml to about 10 µg/ml, from about 25 ng/ml to about 10 µg/ml, from about 50 ng/ml to about 10 µg/ml, from about 50 ng/ml to about 5 µg/ml, from about 100 ng/ml to about 5 µg/ml, from about 200 ng/ml to about 5 µg/ml, from about 250 ng/ml to about 5 µg/ml, from about 500 ng/ml to about 5 µg/ml, from about 1 µg/ml to about 50 µg/ml, from about 0.1 ng/ml to about 5 ng/ml, from about 1 ng/ml to about 10 ng/ml or from about 1 µg/ml to about 10 µg/ml. The pharmaceutical compositions, in certain embodiments, should provide a dosage of from about 0.001 mg to about 2000 mg of compound per kilogram of body weight per day, from about 0.002 mg to about 1000 mg of compound per kilogram of body weight per day, from about 0.005 mg to about 500 mg of compound per kilogram of body weight per day, from about 0.005 mg to about 250 mg of compound per kilogram of body weight per day, from about 0.005 mg to about 200 mg of compound per kilogram of body weight per day, from about 0.005 mg to about 100 mg of compound per kilogram of body weight per day, from about 0.001 mg to about 0.005 mg of compound per kilogram of body weight per day, from about 0.01 mg to about 100 mg of compound per kilogram of body weight per day, from about 0.02 mg to about 100 mg of compound per kilogram of body weight per day, from about 0.05 mg to about 100 mg of compound per kilogram of body weight per day, from about 0.1 mg to about 100 mg of compound per kilogram of body weight per day, from about 0.5 mg to about 100 mg of compound per kilogram of body weight per day, from about 0.75 mg to about 100 mg of compound per kilogram of body weight per day, from about 1 mg to about 100 mg of compound per kilogram of body weight per day, from about 1 mg to about 10 mg of compound per kilogram of body weight per day, from about 0.001 mg to about 5 mg of compound per kilogram of body weight per day, from about 200 mg to about 2000 mg of compound per kilogram of body weight per day, or from about 10 mg to about 100 mg of compound per kilogram of body weight per day. Pharmaceutical dosage unit forms are prepared to provide from about 1 mg to about 1000 mg, from about 1 mg to about 800 mg, from about 5 mg to about 800 mg, from about 1 mg to about 100 mg, from about 1 mg to about 50 mg, from about 5 mg to about 100 mg, from about 10 mg to about 50 mg, from about 10 mg to about 100 mg, from about 25 mg to about 50 mg, and from about 10 mg to about 500 mg of the essential active ingredient or a combination of essential ingredients per dosage unit form.

The active ingredient can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing recurrence of a condition associated with or modulated by one or more caspases, such as those described in Section 5.2. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically, locally, by inhalation spray, nasally, buccally, vaginally, by an implanted reservoir or via nasogastric or orogastric tube. In some embodiments, administration is by an oral route. In other embodiments, administration is by a parenteral route. For oral administration, capsules and tablets can be used. The compositions are in liquid, semi-liquid or solid form and are formulated in a manner suitable for each route of administration. In one embodiment, modes of administration include parenteral and oral modes of administration. In certain embodiments, oral administration is contemplated.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds can be used. Such methods are known to those of skill in this art, and include, but are not limited to, using co-solvents, such as dimethyl sulfoxide (DMSO), using surfactants, such as TWEEN®, or dissolution in aqueous sodium bicarbonate.

Upon mixing or addition of the compound(s), the resulting mixture can be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and can be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil/water emulsions containing suitable quantities of the compounds or pharmaceutically acceptable derivatives thereof. The pharmaceutically therapeutically active compounds and derivatives thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms can be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compounds remain in the body for a long time, they can denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions Dosage forms or compositions containing active ingredient in the range of 0.001% to 100% active ingredient, 0.002% to 100% active ingredient, 0.005% to 90% active ingredient, 0.01% to 100% active ingredient, 0.05% to 100% active ingredient, 0.05% to 90% active ingredient, 0.1% to 100% active ingredient, 0.1% to 1% active ingredient, 0.1% to 0.5% active ingredient, 1% to 100% active ingredient, 1% to 99% active ingredient, 1% to 98% active ingredient, 1% to 97% active ingredient, 1% to 96% active ingredient, 1% to 95% active ingredient, 5% to 95% active ingredient, 10% to 100% active ingredient, 10% to 95% active ingredient, 15% to 95% active ingredient, 20% to 95% active ingredient, 25% to 100% active ingredient, 50% to 100% active ingredient, 50% to 95% active ingredient, 60% to 95% active ingredient or 75% to 100% active ingredient, with the balance made up from nontoxic carrier can be prepared. For oral administration, a pharmaceutically acceptable nontoxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions can contain 0.001% to 100% active ingredient, in one embodiment or 75-95% active ingredient.

The active compounds or pharmaceutically acceptable derivatives can be prepared with carriers that protect the compound against rapid elimination from the body, such as time release formulations or coatings.

The compositions can include other active compounds to obtain desired combinations of properties. The compounds provided herein, or pharmaceutically acceptable derivatives thereof as described herein, can also be advantageously administered for therapeutic or prophylactic purposes, to a subject having a condition modulated by one or more caspases, together with another pharmacological agent known in the general art to be of value in treating the same condition. It is to be understood that such combination therapy constitutes a further aspect of the compositions and methods of treatment provided herein.

Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which can be enteric coated, sugarcoated or film coated. Capsules can be hard or soft gelatin capsules, while granules and powders can be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water-soluble FD and C dyes, mixtures thereof; and water-insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emeticcoatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup can contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient can be included.

Pharmaceutically acceptable carriers included in tablets are binders, lubricants, diluents, disintegrating agents, coloring agents, flavoring agents, and wetting agents. Enteric-coated tablets, because of the entericcoating, resist the action of stomach acid and dissolve or disintegrate in the neutral or alkaline intestines. Sugarcoated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents can also be used in the above dosage forms. Flavoring and sweetening agents are used in compressed tablets, sugarcoated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil in-water or water in oil.

Elixirs are clear, sweetened, hydroalcoholic preparations. Pharmaceutically acceptable carriers used in elixirs include solvents. Syrups are concentrated aqueous solutions of a sugar, for example, sucrose, and can contain a preservative. An emulsion is a two phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, can be encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, can be diluted with a sufficient quantity of a pharmaceutically acceptable liquid carrier, e.g., water, to be easily measured for administration.

Alternatively, liquid or semisolid oral formulations can be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations can be coated as known by those of skill in the art in order to modify or sustain dissolution of the active ingredient. Thus, for example, they can be coated with a conventional enterically digestible coating, such as phenylsalicylate, waxes and cellulose acetate phthalate.

Injectables, Solutions and Emulsions

Parenteral administration, generally characterized by injection, either subcutaneously, intramuscularly or intravenously, is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered can also contain minor amounts of nontoxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can either be aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl phydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit dose parenteral preparations are packaged in an ampule, a vial or a syringe with a needle. All preparations for parenteral administration must be sterile, as is known and practiced in the art.

Illustratively, intravenous or intra-arterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In certain embodiments, a therapeutically effective dosage is formulated to contain a concentration of at least about 0.1% w/w up to about 90% w/w or more, or more than 1% w/w of the active compound to the treated tissue(s). The active ingredient can be administered at once, or can be divided into a number of smaller doses to be administered at intervals of time. It is understood that the precise dosage and duration of treatment is a function of the tissue being treated and can be determined empirically using known testing protocols or by extrapolation from in vivo or in vitro test data. It is to be noted that concentrations and dosage values also can vary with the age of the individual treated. It is to be further understood that for any particular subject, specific dosage regimens can be adjusted over time according to the individual need and the professional judgment of the person administering or supervising the administration of the formulations, and that the concentration ranges set forth herein are exemplary only and are not intended to limit the scope or practice of the claimed formulations.

The compound can be suspended in micronized or other suitable form or can be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and can be empirically determined.

Lyophilized Powders

Of interest herein are also lyophilized powders, which can be reconstituted for administration as solutions, emulsions and other mixtures. They also can be reconstituted and formulated as solids or gels.

The sterile, lyophilized powder is prepared by dissolving a compound provided herein, or a pharmaceutically acceptable derivative thereof, in a suitable solvent. The solvent can contain an excipient which improves the stability or other pharmacological component of the powder or reconstituted solution, prepared from the powder. Excipients that can be used include, but are not limited to, dextrose, sorbital, fructose, corn syrup, xylitol, glycerin, glucose, sucrose or other suitable agent. The solvent can also contain a buffer, such as citrate, sodium or potassium phosphate or other such buffer known to those of skill in the art at about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg or 100-500 mg) or multiple dosages of the compound. The lyophilized powder can be stored under appropriate conditions, such as at about 4 degrees Celsius to room temperature.

Reconstitution of this lyophilized powder with water for injection provides a formulation for use in parenteral administration. For reconstitution, about 1-50 mg, 5-35 mg or about 9-30 mg of lyophilized powder, is added per mL of sterile water or other suitable carrier. The precise amount depends upon the selected compound. Such amount can be empirically determined.

Topical Administration

Topical mixtures are prepared as described for the local and systemic administration. The resulting mixture can be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, can be formulated as 0.01%-10% isotonic solutions, pH about 5-7, with appropriate salts.

Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases can be used. Agents to raise the melting point of suppositories include spermaceti and wax. Rectal suppositories can be prepared either by the compressed method or by molding. In certain embodiments, the weight of a rectal suppository is about 2 to 3 gm.

Tablets and capsules for rectal administration are manufactured using the same pharmaceutically acceptable substance and by the same methods as for formulations for oral administration.

Sustained Release Compositions

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358 and 6,699,500 each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus, the compositions provided encompass single unit dosage forms suitable for oral administration such as, but not limited to, tablets, capsules, gel caps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug can be administered using intravenous infusion, an implantable osmotic pump, a transdermal patch, liposomes, or other modes of administration. In one embodiment, a pump can be used (see, Sefton, *CRC Crit. Ref. Biomed. Eng.* 1987; 14:201, Buchwald et al. *Surgery* 1980; 88:507, Saudek et al., *N. Engl. J. Med* 1989; 321: 574. In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, 1984, pp. 115-138. Other controlled release systems are discussed in the review by Langer (*Science* 1990; 249:1527-1533. The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Targeted Formulations

The compounds provided herein, or pharmaceutically acceptable derivatives thereof, can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, can also be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) can be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Dosage and Unit Dosage Forms

In human therapeutics, the doctor will determine the posology which he considers most appropriate according to a preventive or curative treatment and according to the age, weight, stage of the disease and other factors specific to the subject to be treated. Generally, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. Dose rates of from about 50 to about 500 mg per day are also contemplated.

In certain embodiments, the amount of the compound or composition which will be effective in the treatment of colon cancer or prevention one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses can be extrapolated from dose-response curves derived from in vitro or animal model test systems.

Exemplary doses of a composition include milligram or microgram amounts of the chemotherapeutic agent and caspase inhibitor per kilogram of subject or sample weight (e.g., about 0.001-1000 mg/Kg, about 0.01-100 mg/Kg, about 0.01-50 mg/Kg, about 0.1-25 mg/Kg, or about 0.1-10 mg/Kg. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of the caspase inhibitors described herein and, optionally, where applicable, a co-administered chemotherapeutic agent, for the conditions described herein, lies within the range of from about 0.1 mg to about 1000 mg of each of the chemotherapeutic agent and caspase inhibitor per day, given as a single once-a-day dose or as divided doses throughout a day. In one embodiment, the daily dose is administered twice daily in equally divided doses. Specifically, a daily dose range should be from about 10 mg to about 200 mg per day, more specifically, between about 10 mg and about 150 mg per day, or even more specifically between about 25 and about 100 mg per day. It sometimes is necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts can be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the compound described herein are also encompassed by the above described dosage amounts and dose frequency schedules. Further, when a subject is administered multiple dosages of a compound described herein, not all of the dosages need be the same. For example, the dosage administered to the subject can be increased to improve the prophylactic or therapeutic effect of the compound or it can be decreased to reduce one or more side effects that a particular subject is experiencing.

In one embodiment, the dosage of compounds described herein administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the compounds provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of the caspase inhibitor and, optionally, where applicable, a co-administered chemotherapeutic agent, followed by one or more maintenance doses. In such embodiments, the loading dose can be, for instance, about 60 to about 400 mg per day, or about 100 to about 200 mg per day for one day to five weeks. The loading dose can be followed by one or more maintenance doses. Each maintenance does can be, independently, about from about 10 mg to about 200 mg per day, more specifically, between about 25 mg and about 150 mg per day, or even more specifically between about 25 mg and about 80 mg per day or between about 25 mg and about 50 mg per day. Maintenance doses can be administered daily and can be administered as single doses, or as divided doses.

In certain embodiments, a dose of the caspase inhibitor and, optionally, where applicable, a co-administered chemotherapeutic agent, can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound provided herein is administered to achieve a steady-state concentration in blood or serum of the subject of from about 300 to about 4000 ng/mL, from about 400 to about 1600 ng/mL, or from about 600 to about 1200 ng/mL. Loading doses can be administered to achieve steady-state blood or serum concentrations of about 1200 to about 8000 ng/mL, or about 2000 to about 4000 ng/mL for one to five days. Maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same compound can be repeated and the administrations can be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent can be repeated and the administration can be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable derivative thereof, in a form suitable for administration. Such forms are described in detail above. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

4.7. Articles of Manufacture

The compounds or pharmaceutically acceptable derivatives can be packaged as articles of manufacture containing packaging material, a compound or pharmaceutically acceptable derivative thereof provided herein, which is used for treatment, prevention or amelioration of a condition modulation by caspases or one or more symptoms associated with the condition, and a label that indicates that the compound or pharmaceutically acceptable derivative thereof is used for treatment, prevention or amelioration of the condition or one or more symptoms of the condition.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated.

4.8. Kits

Further provided are kits for use of the compounds provided herein in methods of treatment. The kits can include a caspase inhibitor or composition thereof, and instructions providing information to a health care provider regarding usage for treating or preventing a condition modulated by one or more caspases. Instructions can be provided in printed form or in the form of an electronic medium such as a CD, or DVD, or in the form of a website address where such instructions can be obtained. A unit dose of a caspase inhibitor or composition thereof, can include a dosage such that when administered to a subject, a therapeutically or prophylactically effective plasma level of the compound or composition can be maintained in the subject for at least 1 day. In some embodiments, the compounds or composition can be included as sterile aqueous pharmaceutical compositions or dry powder (e.g., lyophilized) compositions.

4.9. Examples

Assay for the Inhibition of Caspase Activity and Determination of $IC_{50}$ Values Human caspases were purchased from Enzo Biosciences and used according to the manufacturer's instructions. An exemplary caspase assay, for Caspase-1, is provided below:
Caspase-1 Assay Caspase-1 was diluted to 10 U/µl in assay buffer consisting of 50 mM HEPES, pH 7.4, 100 mM NaCl, 0.1% CHAPS, 1 mM EDTA, 10% glycerol and 10 mM DTT.
Reaction Conditions:

45 µl of assay buffer was added into ½ volume microtiter plate. The plate was allowed to equilibrate to assay temperature. 5 µl of Caspase-1 (10 U/µl) was added to each appropriate well. Two 2 blank wells containing just assay buffer without Caspase-1 were included on the plate.

The reaction was started by the addition of 50 µl Ac-YVAD-pNA substrate, for a final substrate concentration of 200 µM. The reaction was continuously monitored at 405 nm.

The data was graphed as $OD_{405\ nm}$ vs time, and the slope was determined over the linear portion of the curve. The rates in OD/min were converted to substrate/min using an extinction coefficient for p-nitroaniline of 10,500 M-1 cm-1, and were adjusted for pathlength of sample. Similarly assays were conducted for Caspase-3, Caspase-8 and Caspase-9. The Table below provides a summary of the binding data for the compounds prepared according to Examples 1-4:

| Compound (Example No.) | Caspase 1 IC$_{50}$ (nM) | Caspase 3 IC$_{50}$ (nM) | Caspase 8 IC$_{50}$ (nM) | Caspase 9 IC$_{50}$ (nM) |
| --- | --- | --- | --- | --- |
| 1 | 9 | 132 | 132 | 122 |
| 2 | 4 | 32 | 28 | 38 |
| 3 | 65 | 1000 | 396 | 1000 |
| 4 | 2 | 200 | 1 | 107 |

The results demonstrate that the compounds provided herein possess potent caspase inhibitory activity.

The following examples are set forth to provide those of ordinary skill in the art with disclosure and description of how the compounds, compositions, and methods described and claimed herein can be made and evaluated; these are intended to be purely exemplary and are not intended to limit the scope of the claimed subject matter.

Representative examples of the preparation of compounds provided herein are described below:

Example 1: (A)-3-(2-(4-Benzyl-3-oxopiperazin-1-yl)acetamido)-4-oxo-5-(2,3,5,6-tetrafluorophenoxy)pentanoic Acid

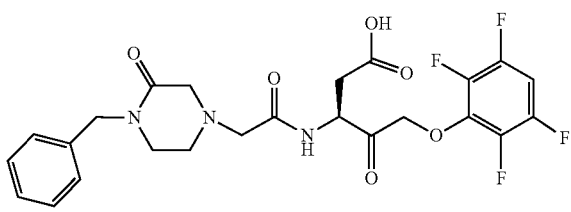 [SMILES: O=C(O)C[C@H](NC(=O)CN1CCN(Cc2ccccc2)C(=O)C1)C(=O)COc1c(F)c(F)cc(F)c1F]

tert-Butyl 4-benzyl-3-oxopiperazine-1-carboxylate A 60% dispersion of sodium hydride in mineral oil (3.6 g, 150 mmol, 1.5 equiv) was added in portions to a solution of tert-butyl 3-oxopiperazine-1-carboxylate (20.02 g, 100 mmol, 1 equiv) in anhydrous THF (400 mL) at 5° C. and the mixture was stirred at room temperature for 1.5 hours. Benzyl bromide (14.27 mL, 120 mmol, 1.2 equiv) was added and the mixture was stirred at room temperature for 15 hours. Water (100 mL) was carefully added to quench the reaction and the mixture was extracted with ethyl acetate (3×200 mL). The combined organic layers were washed with saturated brine (200 mL), dried over sodium sulfate, filtered and concentrated under reduced pressure. The residue was triturated with heptanes (200 mL) to give tert-butyl 4-benzyl-3-oxopiperazine-1-carboxylate (23.5 g, 81% yield) as a white solid.

1-Benzylpiperazin-2-one hydrochloride 4 M HCl in 1,4-dioxane (150 mL, 600 mmol, 12 equiv) was added at room temperature to compound (14.5 g, 50 mmol, 1 equiv) and the mixture was stirred at room temperature for 2 hours, at which time LCMS indicated that the reaction was complete. The mixture was concentrated under reduced pressure and azeotroped with toluene (3×200 mL) to give 1-benzylpiperazin-2-one hydrochloride (15.1 g, quantitative yield) as a viscous pale-yellow oil Methyl 2-(4-benzyl-3-oxopiperazin-1-yl)acetate Triethylamine (20.9 mL, 150 mmol, 3 equiv) was added at room temperature to a suspension of 1-benzylpiperazin-2-one hydrochloride (15.1 g, 50 mmol, 1 equiv) in THF (300 mL). After stirring at room temperature for 10 minutes, methyl bromoacetate (5.68 mL, 60.0 mmol, 1.2 equiv) was added, and the mixture was stirred at room temperature for 15 hours. The reaction was diluted with water (300 mL) and the mixture was extracted with ethyl acetate (3×200 mL). The combined organic layers were washed with saturated brine (200 mL), dried over sodium sulfate, filtered and concentrated under reduced pressure. The residue was purified on an Interchim automated system (330 g silica gel column), eluting with a gradient of 0 to 100% ethyl acetate in heptanes, to give methyl 2-(4-benzyl-3-oxopiperazin-1-yl)acetate (8.5 g, 65% yield) as a pale-yellow oil.

Benzyl 2-(4-benzyl-3-oxopiperazin-1-yl)acetate Triethylamine (20.0 mL, 142.3 mmol, 2.5 equiv) was added at room temperature to a suspension of 1-benzylpiperazin-2-one hydrochloride (13 g, 56.9 mmol, 1 equiv) in THF (300 mL). After stirring at room temperature for 30 minutes, benzyl bromoacetate (10.8 mL, 68.3 mmol, 1.2 equiv) was added to the reaction, which was then stirred an additional 4 hours at room temperature. The mixture was partitioned between water (0.5 L) and ethyl acetate (0.2 L). The aqueous layer was extracted with ethyl acetate (2×0.2 L). The combined organic layers were washed with saturated brine (0.5 L), dried over sodium sulfate, filtered and concentrated under reduced pressure. The residue was purified on an Interchim system (RediSep 220 g column), eluting with a gradient of 0 to 100% ethyl acetate in heptanes, to give Benzyl 2-(4-benzyl-3-oxopiperazin-1-yl)acetate as a beige oil (17.8 g, 93% yield).

2-(4-Benzyl-3-oxopiperazin-1-yl)acetic acid Lithium hydroxide (1.56 g, 64.8 mmol, 2 equiv) was added to a solution of methyl 2-(4-benzyl-3-oxopiperazin-1-yl)acetate (8.5 g, 32.4 mmol, 1 equiv) in tetrahydrofuran (100 mL) and water (50 mL) and the mixture was stirred at room temperature for 5 hours. The mixture was concentrated under reduced pressure to remove THF. The residue was diluted with water (50 mL) and to pH 6 with 1M HCl. The mixture was extracted with ethyl acetate (3×100 mL) and LCMS indicated that the organic layer contained a trace amount of product, and the majority of product stayed in the aqueous layer. The aqueous layer was concentrated under reduced pressure, azeotroped with toluene (3×200 mL) and dried under vacuum at 45° C. overnight to give crude 2-(4-Benzyl-3-oxopiperazin-1-yl)acetic acid (9.84 g) as a yellow foamy solid, which contained some inorganic salts. This material was stirred in dichloromethane (400 mL) for 30 minutes, filtered and the filtrate was concentrated under reduced pressure to give 2-(4-Benzyl-3-oxopiperazin-1-yl)acetic acid (4.2 g) as an off-white solid.

2-(4-Benzyl-3-oxopiperazin-1-yl)acetic acid A suspension of benzyl 2-(4-benzyl-3-oxopiperazin-1-yl)acetate (17.8 g, 52.7 mmol, 1 equiv) and 10% palladium on carbon (1.8 g, 50% wet) in tetrahydrofuran (350 mL) was hydrogenated @ 20 psi for 2 hours. The reaction mixture was filtered through a pad of Celite. The filtrate was concentrated under reduced pressure to give 2-(4-benzyl-3-oxopiperazin-1-yl)acetic acid (12.2 g, 93% yield) as a beige wax.

Benzyl (S)-3-(2-(4-benzyl-3-oxopiperazin-1-yl)acetamido)-4-oxo-5-(2,3,5,6-tetrafluorophenoxy)pentanoate 1-Hydroxy-7-azabenzotriazole (2.01 g, 14.77 mmol, 1.4 equiv) and 1-(3-dimethylaminopropyl)-3-ethylcarbodiimide hydrochloride (2.83 g, 14.77 mmol, 1.4 equiv) were added sequentially at room temperature to a suspension of 2-(4-Benzyl-3-oxopiperazin-1-yl)acetic acid (2.62 g, 10.55 mmol, 1.0 equiv) in acetonitrile (100 mL) and DMF (25 mL). After stirring at room temperature for 1 hour, benzyl (S)-3-amino-4-oxo-5-(2,3,5,6-tetrafluorophenoxy)pentanoate hydrochloride (4.45 g, 10.55 mmol, 1.0 equiv) and triethylamine (4.41 mL, 31.65 mmol, 3 equiv) were sequentially added. After stirring at room temperature for 2 days, the reaction was concentrated under reduced pressure and diluted with ethyl acetate (200 mL). The organic layer was washed with water (2×100 mL), dried over sodium sulfate, filtered and concentrated under reduced pressure. The residue was initially purified on an Interchim automated system (RediSep 120 g silica gel column), eluting with a gradient of 0 to 100% ethyl acetate in heptanes. Final purification on an Interchim automated system (RediSep 40 g silica gel column), eluting with a gradient of 0 to 50% ethyl acetate in dichloromethane gave benzyl (S)-3-(2-(4-benzyl-3-oxopiperazin-1-yl)acetamido)-4-oxo-5-(2,3,5,6-tetrafluorophenoxy)pentanoate (1.42 g, 26% yield) as a colorless oil.

(S)-3-(2-(4-Benzyl-3-oxopiperazin-1-yl)acetamido)-4-oxo-5-(2,3,5,6-tetrafluorophenoxy)pentanoic acid A suspension of benzyl (S)-3-(2-(4-benzyl-3-oxopiperazin-1-yl)acetamido)-4-oxo-5-(2,3,5,6-tetrafluorophenoxy)pentanoate (1.1 g, 1.787 mmol, 1 equiv) and 10% palladium on carbon (0.22 g, 50% wet) in a 1 to 1 mixture of THF and methanol (200 mL) was hydrogenated @ 20 psi for 3 hours. The reaction mixture was filtered through celite and concentrated under reduced pressure. The residue was purified on an Interchim automated system (RediSep 40 g silica gel column), eluting with a gradient of 0 to 100% ethyl acetate in heptanes to give (S)-3-(2-(4-Benzyl-3-oxopiperazin-1-yl)acetamido)-4-oxo-5-(2,3,5,6-tetrafluorophenoxy)pentanoic acid (0.66 g, 70% yield).

Example 2: (A)-3-(2-(4-Benzyl-2-oxopiperazin-1-yl)acetamido)-4-oxo-5-(2,3,5,6-tetrafluorophenoxy) pentanoic Acid

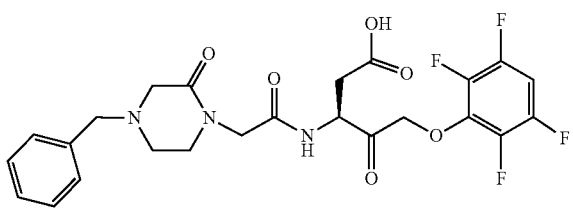 [SMILES: O=C(O)C[C@H](NC(=O)CN1CCN(Cc2ccccc2)CC1=O)C(=O)COc1c(F)c(F)cc(F)c1F]

Benzyl 2-(4-benzyl-2-oxopiperazin-1-yl)acetate A 60% dispersion of sodium hydride in mineral oil (0.32 g, 7.89 mmol, 1.50 equiv) was added to a solution of 1-benzyl-3-oxopiperazine (1.0 g, 5.26 mmol, 1.0 equiv) in 1,4-dioxane (20 mL) at 0° C. and allowed to stir for 30 min. Benzyl bromoacetate (1.57 g, 6.83 mmol, 1.30 equiv) was added and the reaction was allowed to warm to room temperature overnight. Water (25 mL) was carefully added to quench the reaction and the mixture was extracted with ethyl acetate (3×100 mL). The combined organic layers were washed with saturated brine (3×100 mL), dried over sodium sulfate, filtered and reduced under concentrated pressure. The crude material was absorbed onto silica gel (4.5 g) and purified on an Interchim automated chromatography system (Sorbtech silica gel column, 40 g), eluting with a gradient of 0 to 60% ethyl acetate in dichloromethane to give benzyl 2-(4-benzyl-2-oxopiperazin-1-yl)acetate (1.1 g, 64% yield) as a light-yellow oil.

2-(4-Benzyl-2-oxopiperazin-1-yl)acetic acid 1M Lithium hydroxide (0.87 mL, 0.87 mmol, 1.2 equiv) was added to a solution of 2-(4-benzyl-2-oxopiperazin-1-yl)acetic acid (0.25 g, 0.74 mmol, 1.0 equiv) in THF (10 mL) and stirred at room temperature for 18 hours. The reaction was cooled to 0° C. and acidified to pH 3 with 1M HCl. The mixture was concentrated under reduced pressure and the residue was purified on an Interchim automated chromatography system (RediSep C18 column, 100 g), eluting with a gradient of 0 to 15% acetonitrile in water to give 2-(4-benzyl-2-oxopiperazin-1-yl)acetic acid (0.15 g, 82% yield) as a beige oil.

Benzyl (S)-3-(2-(4-benzyl-2-oxopiperazin-1-yl)acetamido)-4-oxo-5-(2,3,5,6-tetrafluorophenoxy)pentanoate 1-Hydroxy-7-azabenzotriazole (3.2 g, 23.68 mmol, 1.2 equiv) and 1-(3-dimethylaminopropyl)-3-ethylcarbodiimide hydrochloride (4.5 g, 23.68 mmol, 1.2 equiv) were added sequentially at room temperature to a suspension of 2-(3-oxo-4-phenylpiperazin-1-yl)acetic acid (4.9 g, 19.74 mmol, 1.0 equiv) in a 2 to 1 mixture of acetonitrile (100 mL) and DMF (50 mL). After stirring at room temperature for 1 hour, Benzyl (S)-3-amino-4-oxo-5-(2,3,5,6-tetrafluorophenoxy) pentanoate hydrochloride (8.3 g, 19.74 mmol, 1.0 equiv) and triethylamine (5.5 mL, 39.47 mmol, 2 equiv) were sequentially added. After stirring at room temperature for 2 days, the reaction was concentrated under reduced pressure. The residue was diluted with ethyl acetate (250 mL). The organic layer was washed with water (2×200 mL), dried over sodium sulfate, filtered and concentrated under reduced pressure. The crude material was absorbed onto silica gel (25 g) and purified on an Interchim automated chromatography system (Sorbtech silica gel column, 330 g), eluting with a gradient of 0 to 100% ethyl acetate in heptanes to give benzyl (S)-3-(2-(4-benzyl-2-oxopiperazin-1-yl)acetamido)-4-oxo-5-(2,3,5,6-tetrafluorophenoxy)pentanoate (10.2 g, 84% yield) as a light-tan solid.

(S)-3-(2-(4-Benzyl-2-oxopiperazin-1-yl)acetamido)-4-oxo-5-(2,3,5,6-tetrafluorophenoxy)pentanoic acid 1M Lithium hydroxide (7.3 mL, 7.3 mmol, 0.9 equiv) was added to a solution of give benzyl (S)-3-(2-(4-benzyl-2-oxopiperazin-1-yl)acetamido)-4-oxo-5-(2,3,5,6-tetrafluorophenoxy) pentanoate (5.0 g, 8.12 mmol, 1.0 equiv) in THF (200 mL) at 0° C. and stirred for 4 hours, keeping the temperature below 10° C. The reaction was cooled to 0° C. and acidified to pH 3 with 1M HCl. The mixture was concentrated under reduced pressure and the residue was purified on an Interchim automated chromatography system (Sorbtech silica gel column, 220 g), eluting with a gradient of 0 to 8% methanol in dichloromethane to give (S)-3-(2-(4-benzyl-2-oxopiperazin-1-yl)acetamido)-4-oxo-5-(2,3,5,6-tetrafluorophenoxy) pentanoic acid (0.99 g, 23% yield).

Example 3: (A)-3-(2-(4-Benzyl-3-oxopiperazin-1-yl)acetamido)-4-oxo-5-((2-(trifluoromethyl)pyrimidin-4-yl)oxy)pentanoic Acid

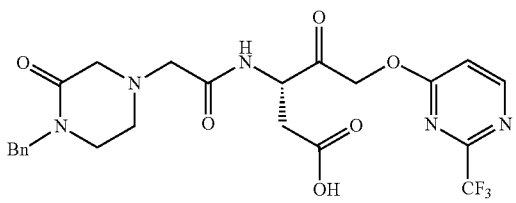 [SMILES: O=C(O)C[C@H](NC(=O)CN1CCN(Cc2ccccc2)C(=O)C1)C(=O)COc1ccnc(C(F)(F)F)n1]

tert-Butyl 4-benzyl-3-oxopiperazine-1-carboxylate: A 60% dispersion of Sodium hydride in mineral oil (3.6 g, 150 mmol, 1.5 equiv) was added in portions to a solution of tert-butyl 3-oxopiperazine-1-carboxylate (20.02 g, 100 mmol, 1 equiv) in anhydrous THF (400 mL) at 5° C. After stirring at room temperature for 1.5 hours, benzyl bromide (14.27 mL, 120 mmol, 1.2 equiv) was added and the mixture was stirred at room temperature for 15 hours. Water (100 mL) was carefully added to quench the reaction and the mixture was extracted with ethyl acetate (3×200 mL). The combined organic layers were washed with saturated brine (200 mL), dried over sodium sulfate, filtered and concentrated under reduced pressure. The residue was triturated with heptanes (200 mL) to give tert-butyl 4-benzyl-3-oxopiperazine-1-carboxylate (25.5 g, 87% yield) as a white solid.

1-Benzylpiperazin-2-one hydrochloride: A mixture of tert-butyl 4-benzyl-3-oxopiperazine-1-carboxylate (8.71 g, 30 mmol, 1 equiv) and 4M HCl in 1,4-dioxane (75 mL, 300 mmol, 10 equiv) was stirred at room temperature for 2 hours, at which time LCMS indicated that the reaction was complete. The mixture was concentrated under reduced pressure and azeotroped with toluene (3×200 mL) to give 1-benzylpiperazin-2-one hydrochloride (9.2 g, quantitative yield) as a viscous pale-yellow oil, which was used subsequently.

Benzyl 2-(4-benzyl-3-oxopiperazin-1-yl)acetate: Triethylamine (12.54 mL, 90 mmol, 3 equiv) was added at room temperature to a suspension of 1-benzylpiperazin-2-one hydrochloride (9.2 g, 30 mmol, 1 equiv) in THF (200 mL). After stirring at room temperature for 10 minutes, benzyl bromoacetate (5.7 mL, 36 mmol, 1.2 equiv) was added and the mixture was stirred at room temperature for 15 hours. The reaction was diluted with water (300 mL) and the mixture was extracted with ethyl acetate (3×200 mL). The combined organic layers were washed with saturated brine (200 mL), dried over sodium sulfate, filtered and concentrated under reduced pressure. The residue was purified on an Interchim automated system (220 g silica gel column), eluting with a gradient of 0 to 100% ethyl acetate in heptanes to give benzyl 2-(4-benzyl-3-oxopiperazin-1-yl)acetate (7.2 g, 71% yield) as a pale-yellow oil.

2-(4-Benzyl-3-oxopiperazin-1-yl)acetic acid: A suspension of benzyl 2-(4-benzyl-3-oxopiperazin-1-yl)acetate (7.2 g, 21.28 mmol, 1 equiv) and 10% palladium on carbon (1.2 g, 50% wet) in THF (400 mL) was hydrogenated @ 20 psi for 4 hours. The reaction mixture was filtered through celite and concentrated under reduced pressure to give 2-(4-benzyl-3-oxopiperazin-1-yl)acetic acid (5.4 g, quantitative yield) as a sticky white solid, which was used subsequently.

Benzyl (S)-3-(2-(4-benzyl-3-oxopiperazin-1-yl)acetamido)-4-oxo-5-((2-(trifluoromethyl)pyrimidin-4-yl)oxy)pentanoate: 1-Hydroxy-7-azabenzotriazole (1.22 g, 8.932 mmol, 1.4 equiv) and 1-(3-dimethylaminopropyl)-3-ethylcarbodiimide hydrochloride (1.71 g, 8.932 mmol, 1.4 equiv) were added sequentially at room temperature to a suspension of 2-(4-benzyl-3-oxopiperazin-1-yl)acetic acid (1.58 g, 6.38 mmol, 1.0 equiv) in 4 to 1 mixture of acetonitrile and DMF (75 mL). After stirring at room temperature for 1 hour, benzyl (S)-3-amino-4-oxo-5-((2-(trifluoromethyl)pyrimidin-4-yl)oxy)pentanoate hydrochloride (2.68 g, 6.38 mmol, 1.0 equiv) and triethylamine (2.67 mL, 19.14 mmol, 3 equiv) were sequentially added. After stirring at room temperature for 18 hours, the reaction was concentrated under reduced pressure and diluted with ethyl acetate (200 mL). The organic layer was washed with water (2×100 mL), dried over sodium sulfate, filtered and concentrated under reduced pressure. The residue was purified on an Interchim automated system (RediSep 220 g silica gel column), eluting with a gradient of 0 to 100% ethyl acetate in heptanes to give benzyl (S)-3-(2-(4-benzyl-3-oxopiperazin-1-yl)acetamido)-4-oxo-5-((2-(trifluoromethyl)pyrimidin-4-yl)oxy)pentanoate (1.63 g, 42% yield) as a pale-yellow oil (S)-3-(2-(4-Benzyl-3-oxopiperazin-1-yl)acetamido)-4-oxo-5-((2-(trifluoromethyl)pyrimidin-4-yl)oxy)pentanoic acid: A suspension of benzyl (S)-3-(2-(4-benzyl-3-oxopiperazin-1-yl)acetamido)-4-oxo-5-((2-(trifluoromethyl)pyrimidin-4-yl)oxy)pentanoate (1.63 g, 2.656 mmol, 1 equiv) and 10% palladium on carbon (0.16 g, 50% wet) in a 1 to 1 mixture of THF and ethyl acetate (160 mL) was hydrogenated @ 20 psi for 3 hours. The reaction mixture was filtered through celite and concentrated under reduced pressure. The residue was purified on an Interchim automated system (RediSepRf 275 g reversed phase column), eluting with a gradient of 0 to 70% acetonitrile in water to give (S)-3-(2-(4-benzyl-3-oxopiperazin-1-yl)acetamido)-4-oxo-5-((2-(trifluoromethyl)pyrimidin-4-yl)oxy)pentanoic acid (0.83 g, 60% yield).

Example 4: (A)-4-Oxo-3-(2-(4-(phenylsulfonyl)piperazin-1-yl)acetamido)-5-(2,3,5,6-tetrafluorophenoxy)pentanoic Acid

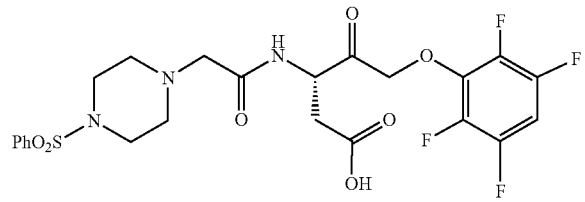

Benzyl 2-(4-(phenylsulfonyl)piperazin-1-yl)acetate: Benzyl bromoacetate (2.4 g, 10.5 mmol, 1.05 equiv) was added to a suspension of sodium carbonate (2.12 g, 20 mmol, 2 equiv) and 1-(phenylsulfonyl)piperazine (2.26 equiv, 10 mmol, 1 equiv) in THF (50 mL). After stirring at room temperature for 18 hours, the resulting solid was removed by filtration. The filtrate was concentrated under reduced pressure. The residue was dissolved in ethyl acetate (100 mL), washed with water (2×50 mL), saturated brine (30 mL), dried over sodium sulfate, filtered, and concentrated to give benzyl 2-(4-(phenylsulfonyl)piperazin-1-yl)acetate (3.8 g, > theory), which was used subsequently.

2-(4-(Phenylsulfonyl)piperazin-1-yl)acetic acid: A suspension of benzyl 2-(4-(phenylsulfonyl)piperazin-1-yl)acetate (3.8 g, 10 mmol, 1 equiv, theoretic) and 10% palladium on carbon (0.38 g, 50% wet) in tetrahydrofuran (20 mL) and ethyl acetate (20 mL) was hydrogenated @ 25 psi for 18 hours. The reaction mixture was filtered through celite and concentrated under reduced pressure. The residue was purified on an Interchim automated system (275 g RediSep C-18 gold column), eluting with a gradient of 0 to 95% acetonitrile (containing 0.1% formic acid) in water (containing 0.1% formic acid) to give 2-(4-(phenylsulfonyl)piperazin-1-yl)acetic acid (2.3 g, 80% yield).

Benzyl (S)-4-oxo-3-(2-(4-(phenylsulfonyl)piperazin-1-yl)acetamido)-5-(2,3,5,6-tetrafluorophenoxy)pentanoate: 1-Hydroxy-7-azabenzotriazole (1.3 g, 9.7 mmol, 1.2 equiv) was added at room temperature to a solution of 2-(4-(phenylsulfonyl)piperazin-1-yl)acetic acid (2.3 g, 8.1 mmol, 1 equiv) in acetonitrile (50 mL). After stirring for 15 minutes, A-(3-dimethylaminopropyl)-N'-ethylcarbodiimide hydrochloride (1.5 g, 8.9 mmol, 1.1 equiv) was added and the reaction stirred for an additional 1 hour. Benzyl (S)-3-amino-4-oxo-5-(2,3,5,6-tetrafluorophenoxy)pentanoate hydrochloride (3.4 g, 8.1 mmol, 1 equiv) and triethylamine (2.3 mL, 16.2 mmol, 2 equiv) were sequentially added and the reaction was stirred at room temperature for 18 hours. The reaction was diluted with water (100 mL) and extract with ethyl acetate (3×100 mL). The combined organic layers were washed with 1N HCl (2×50 mL), saturated brine (50 mL), dried over sodium sulfate, filtered and concentrated under reduced pressure. The residue was purified on an InterChim automated system (80 g SorbTech silica gel column), eluting with a gradient of 0 to 15% methanol in dichloromethane to give benzyl (S)-4-oxo-3-(2-(4-(phenylsulfonyl)piperazin-1-yl)acetamido)-5-(2,3,5,6-tetrafluorophenoxy)pentanoate (2.2 g, 41% yield).

(S)-4-Oxo-3-(2-(4-(phenyl sulfonyl)piperazin-1-yl)acetamido)-5-(2,3,5,6-tetrafluorophenoxy)pentanoic acid: A suspension of benzyl (S)-4-oxo-3-(2-(4-(phenylsulfonyl)piperazin-1-yl)acetamido)-5-(2,3,5,6-tetrafluorophenoxy) pentanoate (2.2 g, 3.4 mmol, 1 equiv) and 10% palladium on carbon (0.22 g, 50% wet) in tetrahydrofuran (30 mL) and ethyl acetate (10 mL) was hydrogenated @ 25 psi for 18 hours. The reaction mixture was filtered through celite and concentrated under reduced pressure. The residue was purified on an Interchim automated system (50 g RediSep C-18 gold column), eluting with a gradient of 0 to 95% acetonitrile (containing 0.1% formic acid) in water (containing 0.1% formic acid) to give (S)-4-oxo-3-(2-(4-(phenyl sulfonyl)piperazin-1-yl)acetamido)-5-(2,3,5,6-tetrafluorophenoxy)pentanoic acid (0.95 g, 50% yield, >98% HPLC purity).

The following compounds were prepared using procedures similar to those described herein and/or routine modifications of the procedures described herein.

| Example | Compound Structure | Mass Spectrum m/z |
|---------|-------------------|-------------------|
| 1 | 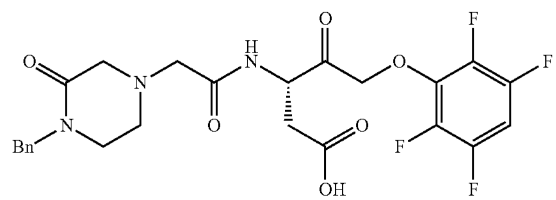 [SMILES: O=C(O)C[C@H](NC(=O)CN1CCN(Cc2ccccc2)C(=O)C1)C(=O)COc1c(F)c(F)cc(F)c1F] | 526.2 (M + H) |
| 2 | 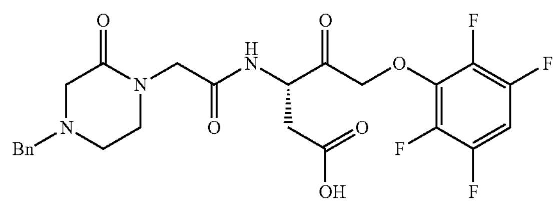 [SMILES: O=C(O)C[C@H](NC(=O)CN1CCN(Cc2ccccc2)CC1=O)C(=O)COc1c(F)c(F)cc(F)c1F] | 526.1 (M + H) |
| 3 | 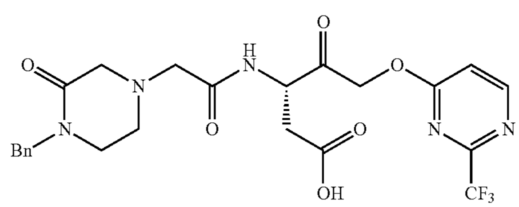 [SMILES: O=C(O)C[C@H](NC(=O)CN1CCN(Cc2ccccc2)C(=O)C1)C(=O)COc1ccnc(C(F)(F)F)n1] | 524.1 (M + H) |
| 4 | 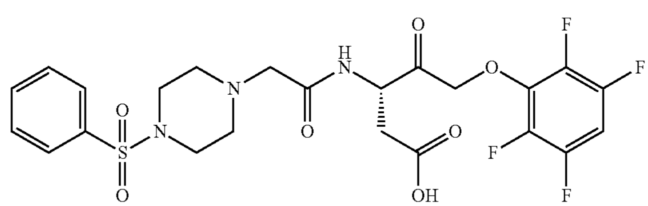 [SMILES: O=C(O)C[C@H](NC(=O)CN1CCN(S(=O)(=O)c2ccccc2)CC1)C(=O)COc1c(F)c(F)cc(F)c1F] | 562.1 (M + H) |
| 5 | 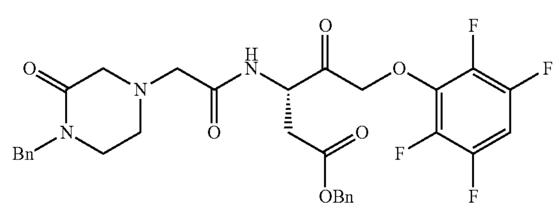 [SMILES: O=C(CN1CCN(Cc2ccccc2)C(=O)C1)N[C@@H](CC(=O)OCc1ccccc1)C(=O)COc1c(F)c(F)cc(F)c1F] | 616.2 (M + H) |
| 6 | 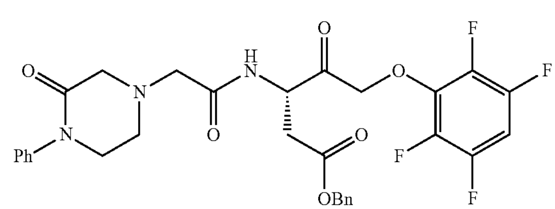 [SMILES: O=C(CN1CCN(c2ccccc2)C(=O)C1)N[C@@H](CC(=O)OCc1ccccc1)C(=O)COc1c(F)c(F)cc(F)c1F] | 602.2 (M + H) |

-continued

| Example | Compound Structure | Mass Spectrum m/z |
|---|---|---|
| 7 | 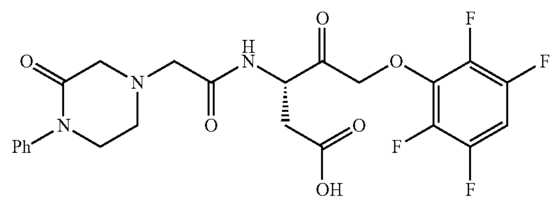 [SMILES: O=C(O)C[C@H](NC(=O)CN1CCN(c2ccccc2)C(=O)C1)C(=O)COc1c(F)c(F)cc(F)c1F] | 512.1(M + H) |
| 8 | 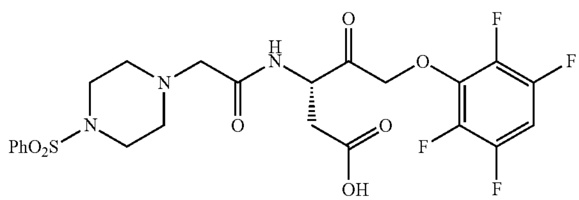 | 562.1 (M + H) |
| 9 | 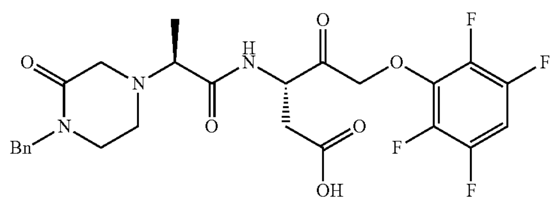 [SMILES: C[C@@H](C(=O)N[C@@H](CC(=O)O)C(=O)COc1c(F)c(F)cc(F)c1F)N1CCN(Cc2ccccc2)C(=O)C1] | 540.2(M + H) |
| 10 | 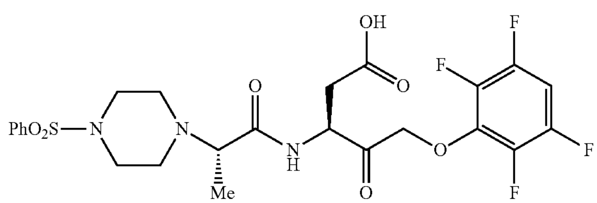 | 576.1(M + H) |
| 11 | 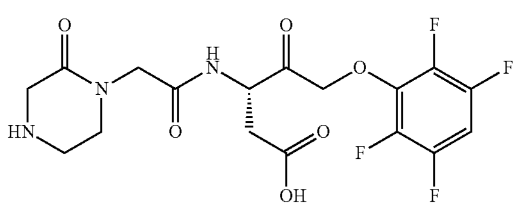 [SMILES: O=C(O)C[C@H](NC(=O)CN1CCNCC1=O)C(=O)COc1c(F)c(F)cc(F)c1F] | 436.1(M + H) |
| 12 | 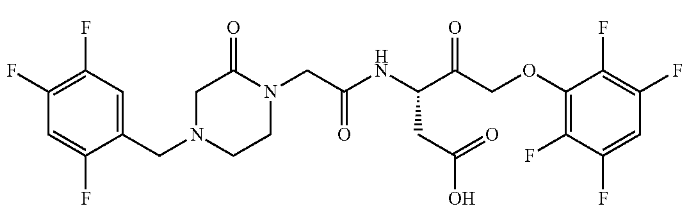 [SMILES: O=C(O)C[C@H](NC(=O)CN1CCN(Cc2cc(F)c(F)cc2F)CC1=O)C(=O)COc1c(F)c(F)cc(F)c1F] | 580.1(M + H) |
| 13 | 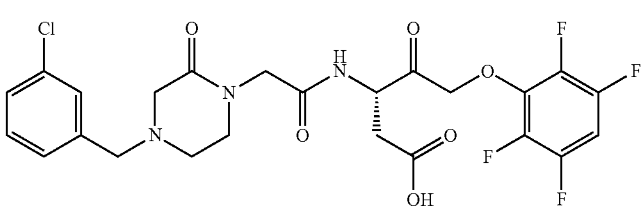 [SMILES: O=C(O)C[C@H](NC(=O)CN1CCN(Cc2cccc(Cl)c2)CC1=O)C(=O)COc1c(F)c(F)cc(F)c1F] | 561.1(M + H) |

-continued

| Example | Compound Structure | Mass Spectrum m/z |
|---|---|---|
| 14 | 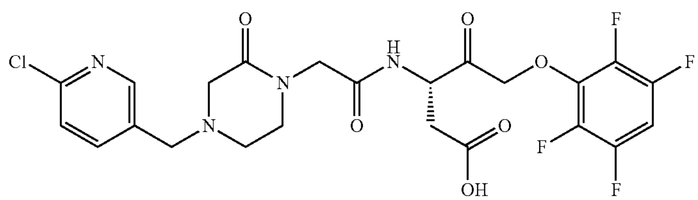 [SMILES: O=C(O)C[C@H](NC(=O)CN1CCN(Cc2ccc(Cl)nc2)CC1=O)C(=O)COc1c(F)c(F)cc(F)c1F] | 562.1(M + H) |
| 15 | 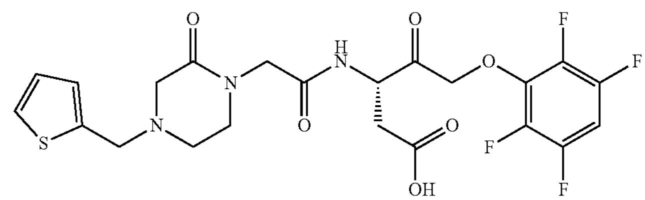 [SMILES: O=C(O)C[C@H](NC(=O)CN1CCN(Cc2cccs2)CC1=O)C(=O)COc1c(F)c(F)cc(F)c1F] | 532.1(M + H) |
| 16 | 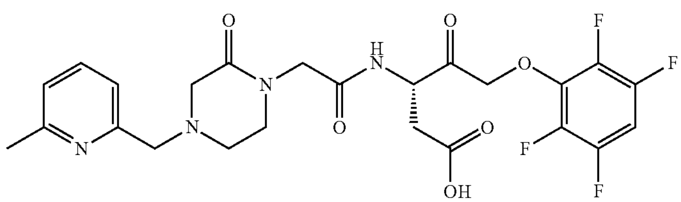 [SMILES: Cc1cccc(CN2CCN(CC(=O)N[C@@H](CC(=O)O)C(=O)COc3c(F)c(F)cc(F)c3F)C(=O)C2)n1] | 541.2(M + H) |
| 17 | 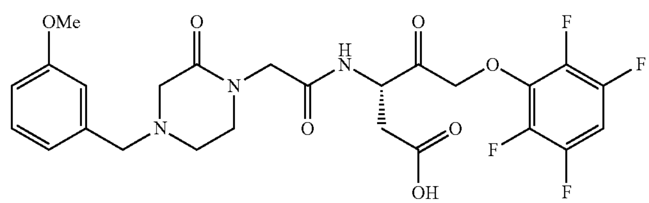 [SMILES: COc1cccc(CN2CCN(CC(=O)N[C@@H](CC(=O)O)C(=O)COc3c(F)c(F)cc(F)c3F)C(=O)C2)c1] | 556.2(M + H) |
| 18 | 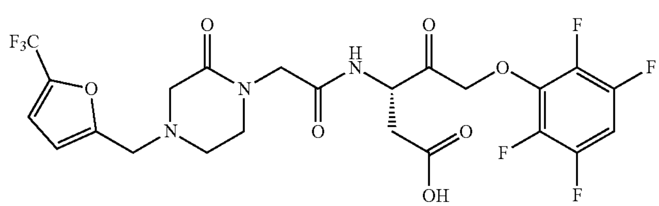 [SMILES: O=C(O)C[C@H](NC(=O)CN1CCN(Cc2ccc(C(F)(F)F)o2)CC1=O)C(=O)COc1c(F)c(F)cc(F)c1F] | 584.1(M + H) |
| 19 | 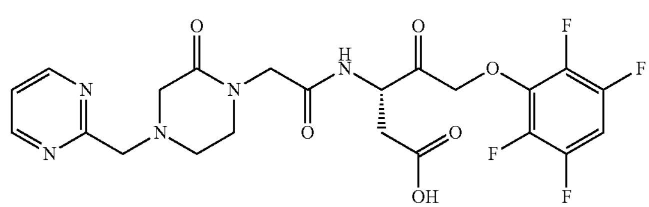 [SMILES: O=C(O)C[C@H](NC(=O)CN1CCN(Cc2ncccn2)CC1=O)C(=O)COc1c(F)c(F)cc(F)c1F] | 528.1(M + H) |
| 20 | 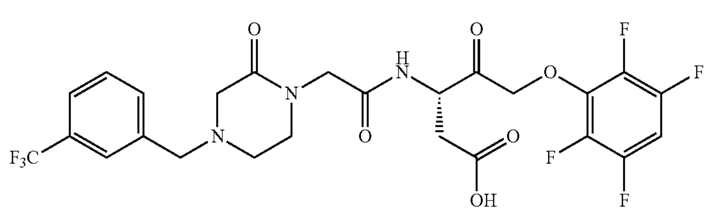 [SMILES: O=C(O)C[C@H](NC(=O)CN1CCN(Cc2cccc(C(F)(F)F)c2)CC1=O)C(=O)COc1c(F)c(F)cc(F)c1F] | 594.1(M + H) |

-continued
| Example | Compound Structure | Mass Spectrum m/z |
|---|---|---|
| 21 | 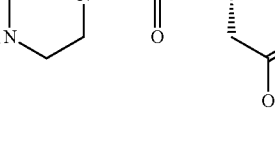 | 540.2(M + H) |
| 22 | 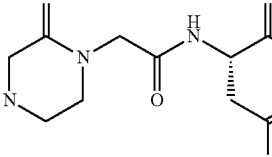 | 590.1(M + H) |
| 23 | 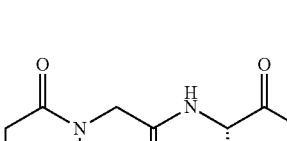 | 612.1(M + H) |
| 24 | 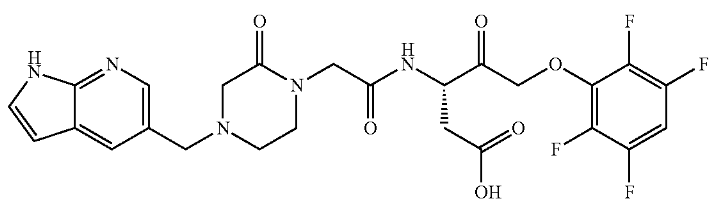 [SMILES: O=C(O)C[C@H](NC(=O)CN1CCN(Cc2cnc3[nH]ccc3c2)CC1=O)C(=O)COc1c(F)c(F)cc(F)c1F] | 566.2(M + H) |
| 25 | 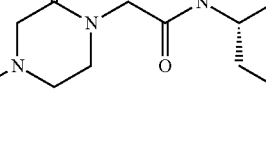 | 611.1(M + H) |
| 26 | 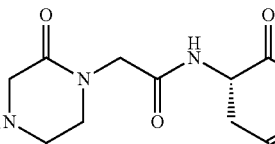 | 582.1(M + H) |
| 27 | 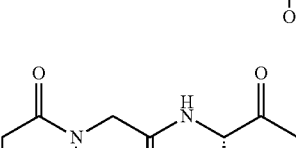 | 582.2(M + H) |

-continued

| Example | Compound Structure | Mass Spectrum m/z |
|---|---|---|
| 28 | 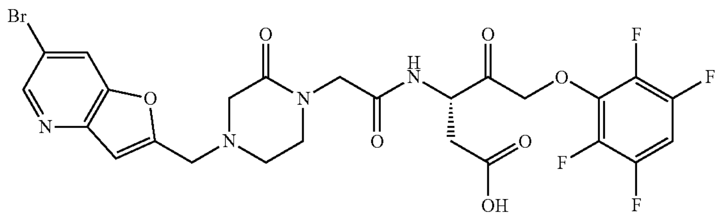 [SMILES: O=C(O)C[C@H](NC(=O)CN1CCN(Cc2cc3ncc(Br)cc3o2)CC1=O)C(=O)COc1c(F)c(F)cc(F)c1F] | 646.1(M + H) |
| 29 | 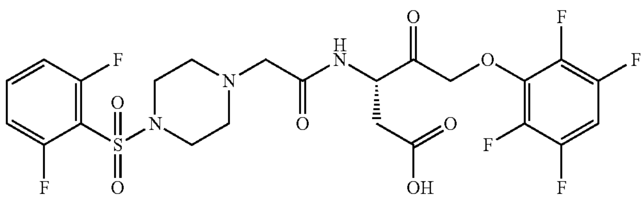 [SMILES: O=C(O)C[C@H](NC(=O)CN1CCN(S(=O)(=O)c2c(F)cccc2F)CC1)C(=O)COc1c(F)c(F)cc(F)c1F] | 598.1(M + H) |
| 30 | 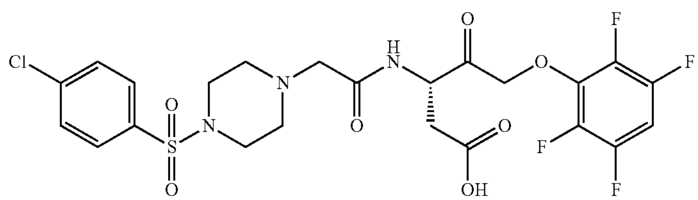 [SMILES: O=C(O)C[C@H](NC(=O)CN1CCN(S(=O)(=O)c2ccc(Cl)cc2)CC1)C(=O)COc1c(F)c(F)cc(F)c1F] | 597.1(M + H) |
| 31 | 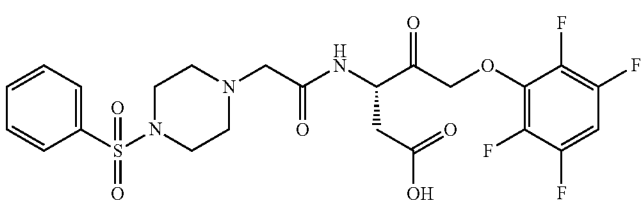 [SMILES: O=C(O)C[C@H](NC(=O)CN1CCN(S(=O)(=O)c2ccccc2)CC1)C(=O)COc1c(F)c(F)cc(F)c1F] | 562.1(M + H) |
| 32 | 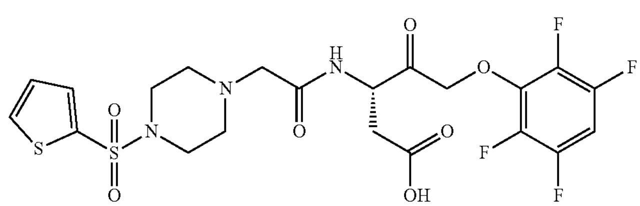 [SMILES: O=C(O)C[C@H](NC(=O)CN1CCN(S(=O)(=O)c2cccs2)CC1)C(=O)COc1c(F)c(F)cc(F)c1F] | 568.1(M + H) |
| 33 | 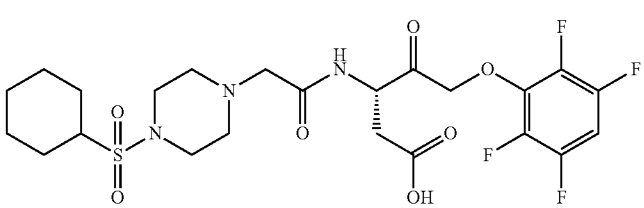 [SMILES: O=C(O)C[C@H](NC(=O)CN1CCN(S(=O)(=O)C2CCCCC2)CC1)C(=O)COc1c(F)c(F)cc(F)c1F] | 568.2(M + H) |
| 34 | 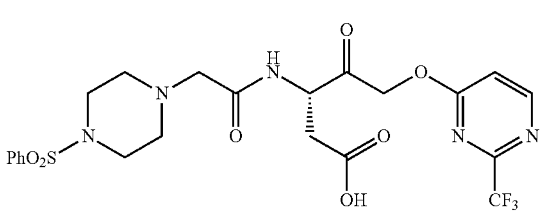 | 560.1(M + H) |

-continued

| Example | Compound Structure | Mass Spectrum m/z |
|---|---|---|
| 35 | 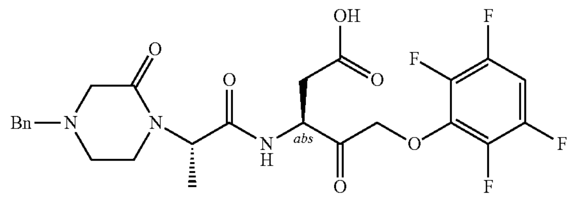 [SMILES: C[C@@H](C(=O)N[C@@H](CC(=O)O)C(=O)COc1c(F)c(F)cc(F)c1F)N1CCN(Cc2ccccc2)CC1=O] | 540.2(M + H) |
| 36 | 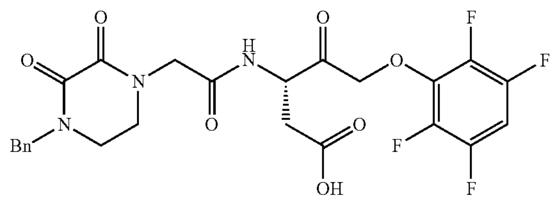 [SMILES: O=C(O)C[C@H](NC(=O)CN1CCN(Cc2ccccc2)C(=O)C1=O)C(=O)COc1c(F)c(F)cc(F)c1F] | 540.1(M + H) |
| 37 | 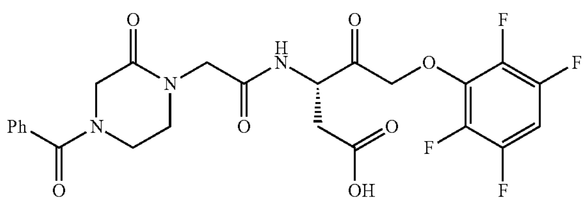 [SMILES: O=C(O)C[C@H](NC(=O)CN1CCN(C(=O)c2ccccc2)CC1=O)C(=O)COc1c(F)c(F)cc(F)c1F] | 538.1(M + H) |
| 38 | 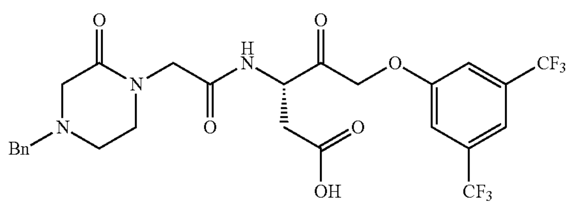 [SMILES: O=C(O)C[C@H](NC(=O)CN1CCN(Cc2ccccc2)CC1=O)C(=O)COc1cc(C(F)(F)F)cc(C(F)(F)F)c1] | 590 (M + H) |
| 39 | 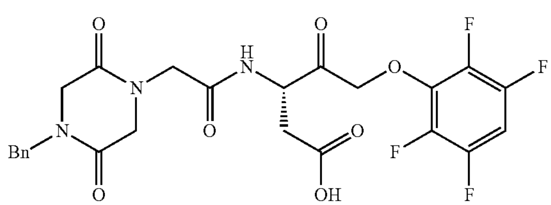 [SMILES: O=C(O)C[C@H](NC(=O)CN1CC(=O)N(Cc2ccccc2)CC1=O)C(=O)COc1c(F)c(F)cc(F)c1F] | 540.1(M + H) |
| 40 | 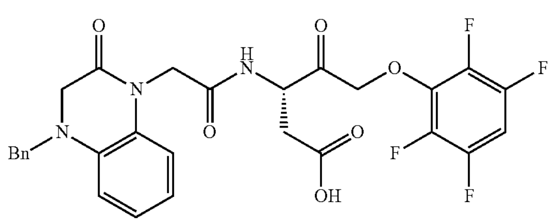 [SMILES: O=C(O)C[C@H](NC(=O)CN1C(=O)CN(Cc2ccccc2)c2ccccc21)C(=O)COc1c(F)c(F)cc(F)c1F] | 574.2(M + H) |
| 41 | 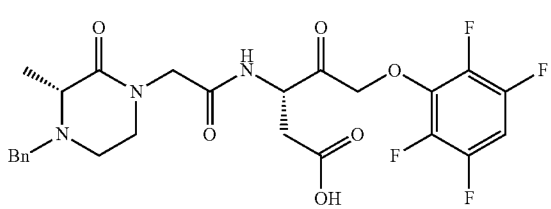 [SMILES: C[C@@H]1C(=O)N(CC(=O)N[C@@H](CC(=O)O)C(=O)COc2c(F)c(F)cc(F)c2F)CCN1Cc1ccccc1] | 540.2(M + H) |

| Example | Compound Structure | Mass Spectrum m/z |
|---|---|---|
| 42 | 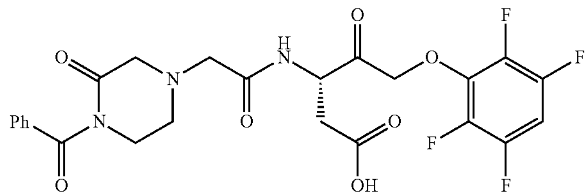 [SMILES: O=C(O)C[C@H](NC(=O)CN1CCN(C(=O)c2ccccc2)C(=O)C1)C(=O)COc1c(F)c(F)cc(F)c1F] | 540.1(M + H) |
| 43 | 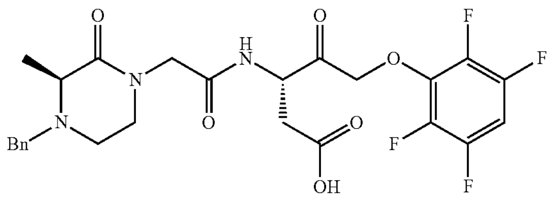 [SMILES: C[C@H]1C(=O)N(CC(=O)N[C@@H](CC(=O)O)C(=O)COc2c(F)c(F)cc(F)c2F)CCN1Cc1ccccc1] | 540.2(M + H) |

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, can be made without departing from the spirit and scope thereof. U.S. patents and publications referenced herein are incorporated by reference.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

What is claimed is:

1. A compound of the following formula:

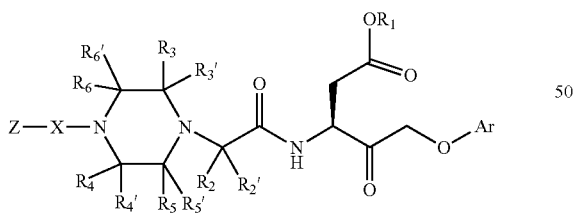

or a pharmaceutically acceptable salt, solvate, tautomer or isomer thereof, wherein:

Z is aryl, arylalkyl, heteroaryl or heteroarylalkyl, each of which is optionally substituted;

Ar is phenyl, phenylalkyl, naphthyl, naphthylalkyl or heteroaryl, each of which is optionally substituted;

X is a bond, $SO_2$, SO, CO or optionally substituted lower alkylene;

$R_1$ is hydrogen, lower alkyl, cycloalkyl, (cycloalkyl)alkyl or optionally substituted phenylalkyl;

$R_2$ and $R_{2'}$ are selected as follows:
  i) $R_2$ and $R_{2'}$ are each independently hydrogen, fluoro, —OH, —$NH_2$, lower alkyl, lower alkoxy, lower alklylthio, mono-alkylamino or di-alkylamino, wherein the alkyl chain(s) of lower alkyl, lower alkoxy, lower alkylthio, mono-alkylamino, or di-alkylamino are optionally substituted with one or more substituents selected from the group consisting of halogen, —OH, —$NH_2$, lower alkoxy, halogen substituted lower alkoxy, lower alkylthio, halogen substituted lower alkylthio, mono-alkylamino, di-alkylamino, and cycloalkylamino; or
  ii) $R_2$ and $R_{2'}$ combine with the carbon to which they are attached to form a 3-7 membered monocyclic cycloalkyl or 5-7 membered monocyclic heterocycloalkyl, wherein the monocyclic cycloalkyl or monocyclic heterocycloalkyl are optionally substituted with one or more substituents selected from the group consisting of halogen, —OH, —$NH_2$, lower alkyl, halogen substituted lower alkyl, lower alkoxy, halogen substituted lower alkoxy, lower alkylthio, halogen substituted lower alkylthio, mono-alkylamino, di-alkylamino, and cycloalkylamino;

$R_3$, $R_{3'}$, $R_4$, $R_{4'}$, $R_5$, $R_{5'}$, $R_6$ and $R_{6'}$ are selected as follows:
  i) $R_3$, $R_{3'}$, $R_4$, $R_{4'}$, $R_5$, $R_{5'}$, $R_6$ and $R_{6'}$ are each independently hydrogen, optionally substituted lower alkyl, optionally substituted $C_{2-6}$ alkenyl, optionally substituted $C_{2-6}$ alkynyl, optionally substituted aryl, optionally substituted heteroaryl, optionally substituted arylalkyl or optionally substituted heteroarylalkyl;
  ii) $R_3$, $R_{3'}$ and $R_6$, $R_{6'}$ together form an optionally substituted aryl, optionally substituted heteroaryl ring, and $R_4$, $R_{4'}$, $R_5$ and $R_{5'}$ are each independently hydrogen, optionally substituted lower alkyl, optionally substituted $C_{2-6}$ alkenyl, optionally substituted $C_{2-6}$ alkynyl, optionally substituted aryl, optionally substituted heteroaryl, optionally substituted arylalkyl or optionally substituted heteroarylalkyl;
  iii) $R_4$, $R_{4'}$ and $R_5$, $R_{5'}$ together form an optionally substituted aryl or optionally substituted heteroaryl ring, and $R_3$, $R_{3'}$, $R_6$ and $R_{6'}$ are each independently hydrogen, optionally substituted lower alkyl, optionally substituted $C_{2-6}$ alkenyl, optionally substituted $C_{2-6}$ alkynyl, optionally substituted aryl, optionally substituted heteroaryl, optionally substituted arylalkyl or optionally substituted heteroarylalkyl, with the proviso that when $R_3$, $R_{3'}$ and $R_6$, $R_{6'}$ together form an aryl, substituted aryl, heteroaryl or substituted heteroaryl ring, $R_4$, $R_{4'}$ and $R_5$, $R_{5'}$ cannot together form an aryl, substituted aryl, heteroaryl or substituted heteroaryl ring and when $R_4$, $R_{4'}$ and $R_5$, $R_{5'}$ together form an aryl, substituted aryl, heteroaryl or substituted heteroaryl ring, $R_3$, $R_{3'}$ and $R_6$, $R_{6'}$ cannot together form an aryl, substituted aryl, heteroaryl or substituted heteroaryl ring; or iv) $R_3$ and $R_{3'}$ together, $R_4$ and $R_{4'}$ together, $R_5$ and $R_{5'}$ together or $R_6$ and $R_{6'}$ together is oxo, and all substituents for $R_3$, $R_{3'}$, $R_4$, $R_{4'}$, $R_5$, $R_{5'}$, $R_6$ and $R_{6'}$ other than the oxo being as defined in i), ii) and iii) above, with the proviso that:

when $R_3$ and $R_{3'}$ together is oxo, none or one of $R_4$ and $R_{4'}$ together, $R_5$ and $R_{5'}$ together and $R_6$ and $R_{6'}$ together is oxo, when $R_4$ and $R_{4'}$ together is oxo, none or one of $R_3$ and $R_{3'}$ together, $R_5$ and $R_{5'}$ together and $R_6$ and $R_{6'}$ together is oxo, when $R_5$ and $R_{5'}$ together is oxo, none or one of $R_3$ and $R_{3'}$ together, $R_4$ and $R_{4'}$ together and $R_6$ and $R_{6'}$ together is oxo, and when $R_6$ and $R_{6'}$ together is oxo, none or one of $R_3$ and $R_{3'}$ together, $R_4$ and $R_{4'}$ together and $R_5$ and $R_{5'}$ together is oxo, wherein, unless specified otherwise, the substituents on cycloalkyl, aryl, heterocycloalkyl, and heteroaryl groups, when present are selected from one or more, substituents $Q^1$, wherein each $Q^1$ is independently selected from halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$), —C(S)—N(R$^o$—R$^o$, —S(O)$_2$—N(H)—R$^o$), —S(O)$_2$—N(R$^o$—R$^o$, —C(NH)—N(H)—R$^o$, —C(NH)N(R$^p$)R$^o$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, —R$^f$, and —R$^g$;

unless specified otherwise, the substituents on alkyl, alkenyl and alkynyl groups, when present are selected from one or more substituents $Q^2$, wherein each $Q^2$ is independently selected from —F, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, and —R$^g$;

each R$^o$, R$^p$, and R$^c$ are independently selected from the group consisting of R$^d$, R$^e$, R$^f$, and R$^g$, or R$^p$ and R$^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, substituents selected from the group consisting of halogen, —NO$_2$, —CN, —OH, —NH$_2$, —O—R$^u$, —N(H)—R$^u$, —N(R$^u$)—R$^u$, —R$^x$, and —R$^y$;

each R$^d$ is independently lower alkyl, wherein lower alkyl is optionally substituted with one or more substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(S)—N(R$^k$)—R$^k$, —N(R$^k$)C(O)N(R$^k$)R$^k$, —N(R$^k$)C(S)N(R$^k$)R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^i$, and —R$^j$;

each R$^e$ is independently lower alkenyl, wherein lower alkenyl is optionally substituted with one or more substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)C(O)N(R$^k$)R$^k$, —N(R$^k$)C(S)N(R$^k$)R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, and —R$^j$;

each R$^f$ is independently lower alkynyl, wherein lower alkynyl is optionally substituted with one or more substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)C(O)N(R$^k$)R$^k$, —N(R$^k$)C(S)N(R$^k$)R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, and —R$^j$;

each R$^g$ is independently selected from the group consisting of cycloalkyl, heterocycloalkyl, aryl, and heteroaryl, wherein cycloalkyl, heterocycloalkyl, aryl, and heteroaryl are optionally substituted with one or more substituents selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)C(O)N(H)R$^k$, —N(R$^k$)C(S)N(H)R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, —R$^i$, and —R$^j$;

R$^k$, R$^m$, and R$^n$ are each independently selected from the group consisting of R$^h$, R$^i$, and R$^j$, or R$^m$ and R$^n$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more substituents selected from the group consisting of halogen, —NO$_2$, —CN, —OH, —NH$_2$, —O—R$^u$, —S—R$^u$, —N(H)—R$^u$, —NR$^u$R$^u$, —R$^x$, and —R$^y$;

each R$^h$ is independently lower alkyl optionally substituted with one or more substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R$^r$)—R$^r$, —S(O)$_2$—N(H)—R$^r$, —S(O)$_2$—N(R$^r$)—R$^r$, —C(NH)—N(H)—R$^r$, —C(NH)N(R$^s$)R$^t$, —N(H)—C(O)—R$^r$, —N(H)—C(S)—R$^r$, —N(R$^r$)—C(O)—R$^r$, —N(R$^r$)—C(S)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)$_2$—N(H)—R$^r$, —N(R$^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(H)—R$^r$, —N(R$^r$)—R$^r$, —R$^i$, and —R$^j$;

each R$^i$ is independently selected from the group consisting of lower alkenyl and lower alkynyl, wherein lower alkenyl or lower alkynyl are optionally substituted with one or more substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R$^r$)—R$^r$, —S(O)$_2$—N(H)—R$^r$, —S(O)$_2$—N(R$^r$)—R$^r$, —C(NH)—N(H)—R$^r$, —C(NH)—N(R$^s$)—R$^t$, —N(H)—C(O)—R$^r$, —N(H)—C(S)—R$^r$, —N(R$^r$)—C(O)—R$^r$, —N(R$^r$)—C(S)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)$_2$—N(H)—R$^r$, —N(R$^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(H)—R$^r$, —N(R$^r$)—R$^r$, and —R$^j$;

each R$^j$ is independently selected from the group consisting of cycloalkyl, heterocycloalkyl, aryl, and heteroaryl, wherein cycloalkyl, heterocycloalkyl, aryl, and heteroaryl are optionally substituted with one or more substituents selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R$^r$)—R$^r$, —S(O)$_2$—N(H)—R$^r$, —S(O)$_2$—N(R$^r$)—R$^r$, —C(NH)—N(H)—R$^r$, —C(NH)N(R$^s$)R$^t$, —N(H)—C(O)—R$^r$, —N(H)—C(S)—R$^r$, —N(R$^r$)—C(O)—R$^r$, —N(R$^r$)—C(S)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)$_2$—N(H)—R$^r$, —N(R$^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(R$^r$)—R$^r$, cycloalkylamino, and —R$^x$;

each R$^r$, R$^s$, and R$^t$ at each occurrence are independently selected from the group consisting of lower alkyl, C$_{3-6}$ alkenyl, C$_{3-6}$alkynyl, cycloalkyl, heterocycloalkyl, aryl and heteroaryl, wherein lower alkyl is optionally substituted with one or more substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein C$_{3-6}$ alkenyl or C$_{3-6}$ alkynyl are optionally substituted with one or more substituents selected from the group consisting of —R$^y$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, or R$^s$ and R$^t$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more substituents selected from the group consisting of halogen, —NO$_2$, —CN, —OH, —NH$_2$, —O—R$^u$, —N(H)—R$^u$, —N(R$^u$)—R$^u$, —R$^x$, and —R$^y$;

each R$^u$ is independently selected from the group consisting of lower alkyl, C$_{3-6}$ alkenyl, C$_{3-6}$ alkynyl, cycloalkyl, heterocycloalkyl, aryl, and heteroaryl, wherein lower alkyl is optionally substituted with one or more substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein C$_{3-6}$ alkenyl or C$_{3-6}$ alkynyl are optionally substituted with one or more substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

each R$^x$ is selected from the group consisting of lower alkyl, lower alkenyl and lower alkynyl, wherein lower alkyl is optionally substituted with one or more substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein lower alkenyl or lower alkynyl are optionally substituted with one or more substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; and each R$^y$ is selected from the group consisting of cycloalkyl, heterocycloalkyl, aryl, and heteroaryl, wherein cycloalkyl, heterocycloalkyl, aryl, and heteroaryl are optionally substituted with one or more substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

2. The compound of claim 1, wherein R$_6$ and R$_{6'}$ together is oxo.

3. The compound of claim 1, wherein R$_3$, R$_{3'}$, R$_4$, R$_{4'}$, R$_5$ and R$_{5'}$ are each hydrogen.

4. The compound of claim 1, wherein R$_3$ and R$_{3'}$ together, R$_4$ and R$_{4'}$ together or R$_5$ and R$_{5'}$ together is oxo.

5. The compound of claim 1, wherein R$_3$, R$_{3'}$, R$_6$ and R$_{6'}$ together form an aryl, substituted aryl, heteroaryl or substituted heteroaryl ring, or R$_4$, R$_{4'}$, R$_5$ and R$_{5'}$ together form an aryl, substituted aryl, heteroaryl or substituted heteroaryl ring.

6. The compound of claim 1, wherein Z is aryl or substituted aryl.

7. The compound of claim 1, wherein Z—X— is selected from among 3-chlorobenzyl, 3-(tert-butyl)benzyl, 3,5-difluorobenzyl, 5-fluoro-(1,1'-biphenyl)-3-ylmethyl, 4-(naphthalen-2-yl)methyl, 5-(phenylpyridin-3-yl)methyl, 1H-pyrrolo[2,3-b]pyridin-5-yl)methyl, 3,5-difluorobenzyl, 5-fluoro-[1,1'-biphenyl]-3-yl)methyl, 4-(naphthalen-2-yl)methyl, 5-(phenylpyridin-3-yl)methyl, 6-(methylpyridin-2- yl)methyl, 4-(thiophen-2-yl)methyl, 5-(trifluoromethyl) furan-2-yl)methyl, 6-(bromofuro[3,2-b]pyridin-2-yl)methyl, 6-(chloropyridin-3-yl)methyl, 3-methoxybenzyl, 4-methoxybenzyl, 4-chlorobenzyl, 3-phenoxybenzyl, 2-carboxybenzyl, 3-carboxybenzyl, 2-acetamidobenzyl, 2,4-(bis-trifluromethyl)benzyl, 3-methylbenzyl, 2,4,5-trifluorobenzyl, 3-(trifluoromethyl)benzyl, 6-(chloropyridin-3-yl) methyl, 4-(pyrimidin-2-yl)methyl, 4-benzyl sulfonyl, 2,6-(difluorophenyl)sulfonyl, 4-phenyl sulfonyl, 4-(chlorophenyl)sulfonyl, 4-(thiophen-2-yl)sulfonyl, 4-cyclohexylsulfonyl, 2,6-(difluorophenyl)sulfonyl, 4-(chlorophenyl)sulfonyl, 4-(phenyl sulfonyl), 4-(thiophen-2-yl) sulfonyl, 4-phenylsulfonyl, 4-phenyl, 4-benzyl and benzoyl.

8. The compound claim 1, wherein Ar is phenyl or substituted phenyl.

9. The compound of claim 8, wherein Ar is selected from among 2-, 3- or 4-chlorophenyl, 2,6-dichlorophenyl, 2,5-dichlorophenyl, 3,4-dichlorophenyl, 2,3,5-trichlorophenyl, 2,3,5,6-tetrachlorophenyl, 2-, 3- or 4-bromophenyl, 2,6-dibromophenyl, 2,5-dibromophenyl, 3,4-dibromophenyl, 2,3,5-tribromophenyl, 2,3,5,6-tetrabromophenyl, 2-, 3- or 4-fluorophenyl, 2,6-difluorophenyl, 2,5-difluorophenyl, 3,4-difluorophenyl, 2,3,5-trifluorophenyl, 2,3,5,6-tetrafluorophenyl and 3-chloro-4-fluorophenyl.

10. The compound of claim 9, wherein Ar is 2,3,5,6-tetrafluorophenyl.

11. The compound of claim 8, wherein Ar is selected from among 3-trifluoromethylphenyl, 2,6 difluoro-4-trifluoromethylphenyl and 5-trifluoromethylphenyl.

12. The compound of claim 8, wherein Ar is a bis (trifluoromethyl)phenyl.

13. The compound of claim 12, wherein Ar is 3,5-bis (trifluoromethyl)phenyl.

14. The compound of claim 1, wherein Ar is heteroaryl or substituted heteroaryl.

15. The compound of claim 14, wherein Ar is selected from among substituted pyridyl, substituted pyridazyl, substituted pyrimidyl and substituted pyrazinyl.

16. The compound of claim 15, wherein Ar is substituted pyrimidyl.

17. The compound of claim 16, wherein Ar is 2-trifluoromethylpyrimidyl.

18. The compound of claim 1 selected from:
(S)-3-(2-(4-(3-chlorobenzyl)-3-oxopiperazin-1-yl)acetamido)-4-oxo-5-(2,3,5,6-tetrafluorophenoxy)pentanoic acid
(S)-3-(2-(4-(3-(tert-butyl)benzyl)-3-oxopiperazin-1-yl) acetamido)-4-oxo-5-(2,3,5,6-tetrafluorophenoxy)pentanoic acid
(S)-3-(2-(4-(3,5-difluorobenzyl)-3-oxopiperazin-1-yl)acetamido)-4-oxo-5-(2,3,5,6-tetrafluorophenoxy)pentanoic acid
(S)-3-(2-(4-((5-fluoro-[1,1'-biphenyl]-3-yl)methyl)-3-oxopiperazin-1-yl)acetamido)-4-oxo-5-(2,3,5,6-tetrafluorophenoxy)pentanoic acid
(S)-3-(2-(4-(naphthalen-2-ylmethyl)-3-oxopiperazin-1-yl)acetamido)-4-oxo-5-(2,3,5,6-tetrafluorophenoxy) pentanoic acid
(S)-4-oxo-3-(2-(3-oxo-4-((5-phenylpyridin-3-yl)methyl) piperazin-1-yl)acetamido)-5-(2,3,5,6-tetrafluorophenoxy)pentanoic acid
(S)-3-((S)-2-(4-benzyl-3-oxopiperazin-1-yl)propanamido)-4-oxo-5-(2,3,5,6-tetrafluorophenoxy)pentanoic acid
(S)-3-(2-(4-benzyl-3-oxopiperazin-1-yl)-2-methylpropanamido)-4-oxo-5-(2,3,5,6-tetrafluorophenoxy)pentanoic acid (S)-3-(1-(4-(3-chlorobenzyl)-3-oxopiperazin-1-yl)cyclopentane-1-carboxamido)-4-oxo-5-(2,3,5,6-tetrafluorophenoxy)pentanoic acid
(3S)-4-oxo-3-(2-(3-oxo-4-((5-phenylpyridin-3-yl) methyl)piperazin-1-yl)propanamido)-5-(2,3,5,6-tetrafluorophenoxy)pentanoic acid
(S)-3-(2-(4-((1H-pyrrolo[2,3-b]pyridin-5-yl)methyl)-3-oxopiperazin-1-yl)acetamido)-4-oxo-5-(2,3,5,6-tetrafluorophenoxy)pentanoic acid
(S)-3-(2-(4-((3,3-dimethyl-2-oxo-2,3-dihydro-1H-pyrrolo[2,3-b]pyridin-5-yl)methyl)-3-oxopiperazin-1-yl) acetamido)-4-oxo-5-(2,3,5,6-tetrafluorophenoxy)pentanoic acid
(S)-3-(2-(4-(3-chlorobenzyl)-2-oxopiperazin-1-yl)acetamido)-4-oxo-5-(2,3,5,6-tetrafluorophenoxy)pentanoic acid
(S)-3-(2-(4-(3-(tert-butyl)benzyl)-2-oxopiperazin-1-yl) acetamido)-4-oxo-5-(2,3,5,6-tetrafluorophenoxy)pentanoic acid (3S)-3-(2-(4-(3,5-difluorobenzyl)-2-methyl-3-oxopiperazin-1-yl)acetamido)-4-oxo-5-(2,3,5,6-tetrafluorophenoxy)pentanoic acid
(3S)-3-(2-(4-((5-fluoro-[1,1'-biphenyl]-3-yl)methyl)-3-methyl-2-oxopiperazin-1-yl)acetamido)-4-oxo-5-(2,3,5,6-tetrafluorophenoxy)pentanoic acid
(S)-3-(2-(4-(naphthalen-2-ylmethyl)-2-oxopiperazin-1-yl)acetamido)-4-oxo-5-(2,3,5,6-tetrafluorophenoxy) pentanoic acid
(S)-4-oxo-3-(2-(2-oxo-4-((5-phenylpyridin-3-yl)methyl) piperazin-1-yl)acetamido)-5-(2,3,5,6-tetrafluorophenoxy)pentanoic acid
(S)-3-(2-(4-((6-methylpyridin-2-yl)methyl)-2-oxopiperazin-1-yl)acetamido)-4-oxo-5-(2,3,5,6-tetrafluorophenoxy)pentanoic acid
(S)-4-oxo-3-(2-(3-oxo-4-(thiophen-2-ylmethyl)piperazin-1-yl)acetamido)-5-(2,3,5,6-tetrafluorophenoxy)pentanoic acid
(S)-4-oxo-3-(2-(3-oxo-4-((5-(trifluoromethyl)furan-2-yl) methyl)piperazin-1-yl)acetamido)-5-(2,3,5,6-tetrafluorophenoxy)pentanoic acid
(S)-3-(2-(4-((6-bromofuro[3,2-b]pyridin-2-yl)methyl)-3-oxopiperazin-1-yl)acetamido)-4-oxo-5-(2,3,5,6-tetrafluorophenoxy)pentanoic acid
(S)-3-(2-(4-((6-chloropyridin-3-yl)methyl)-2-oxopiperazin-1-yl)acetamido)-4-oxo-5-(2,3,5,6-tetrafluorophenoxy)pentanoic acid
(S)-4-oxo-3-(2-(3-oxo-4-(pyrimidin-2-ylmethyl)piperazin-1-yl)acetamido)-5-(2,3,5,6-tetrafluorophenoxy) pentanoic acid
(S)-3-(2-(4-(3-methoxybenzyl)-3-oxopiperazin-1-yl)acetamido)-4-oxo-5-(2,3,5,6-tetrafluorophenoxy)pentanoic acid
(S)-3-(2-(4-(3-methylbenzyl)-2-oxopiperazin-1-yl)acetamido)-4-oxo-5-(2,3,5,6-tetrafluorophenoxy)pentanoic acid
(S)-4-oxo-3-(2-(3-oxo-4-(2,4,5-trifluorobenzyl)piperazin-1-yl)acetamido)-5-(2,3,5,6-tetrafluorophenoxy) pentanoic acid
(S)-4-oxo-3-(2-(2-oxo-4-(3-(trifluoromethyl)benzyl)piperazin-1-yl)acetamido)-5-(2,3,5,6-tetrafluorophenoxy) pentanoic acid
(S)-3-(2-(4-((6-chloropyridin-3-yl)methyl)-3-oxopiperazin-1-yl)acetamido)-4-oxo-5-(2,3,5,6-tetrafluorophenoxy)pentanoic acid
(S)-4-oxo-3-(2-(3-oxo-4-(pyrimidin-2-ylmethyl)piperazin-1-yl)acetamido)-5-(2,3,5,6-tetrafluorophenoxy) pentanoic acid (S)-3-(2-(4-(benzylsulfonyl)-2-oxopiperazin-1-yl)acetamido)-4-oxo-5-(2,3,5,6-tetrafluorophenoxy)pentanoic acid (S)-3-(2-(4-((2,6-difluorophenyl)sulfonyl)-2-oxopiperazin-1-yl)acetamido)-4-oxo-5-(2,3,5,6-tetrafluorophenoxy)pentanoic acid (S)-4-oxo-3-(2-(4-(phenylsulfonyl)piperazin-1-yl)acetamido)-5-(2,3,5,6-tetrafluorophenoxy)pentanoic acid (S)-4-oxo-3-((S)-2-(4-(phenylsulfonyl)piperazin-1-yl)propanamido)-5-(2,3,5,6-tetrafluorophenoxy)pentanoic acid (S)-3-(2-(4-((4-chlorophenyl)sulfonyl)-2-oxopiperazin-1-yl)acetamido)-4-oxo-5-(2,3,5,6-tetrafluorophenoxy)pentanoic acid (S)-4-oxo-3-(2-(2-oxo-4-(thiophen-2-ylsulfonyl)piperazin-1-yl)acetamido)-5-(2,3,5,6-tetrafluorophenoxy)pentanoic acid (S)-3-(2-(4-(cyclohexylsulfonyl)-2-oxopiperazin-1-yl)acetamido)-4-oxo-5-(2,3,5,6-tetrafluorophenoxy)pentanoic acid (S)-3-(2-(4-((2,6-difluorophenyl)sulfonyl)piperazin-1-yl)acetamido)-4-oxo-5-(2,3,5,6-tetrafluorophenoxy)pentanoic acid (S)-3-(2-(4-((4-chlorophenyl)sulfonyl)piperazin-1-yl)acetamido)-4-oxo-5-(2,3,5,6-tetrafluorophenoxy)pentanoic acid (S)-4-oxo-3-(2-(4-(phenylsulfonyl)piperazin-1-yl)acetamido)-5-(2,3,5,6-tetrafluorophenoxy)pentanoic acid (S)-4-oxo-5-(2,3,5,6-tetrafluorophenoxy)-3-(2-(4-(thiophen-2-ylsulfonyl)piperazin-1-yl)acetamido)pentanoic acid (S)-3-(2-(4-(cyclohexylsulfonyl)piperazin-1-yl)acetamido)-4-oxo-5-(2,3,5,6-tetrafluorophenoxy)pentanoic acid (S)-4-oxo-3-(2-(4-(phenylsulfonyl)piperazin-1-yl)acetamido)-5-((2-(trifluoromethyl)pyrimidin-4-yl)oxy)pentanoic acid (S)-4-oxo-3-(2-(4-(phenylsulfonyl)piperazin-1-yl)acetamido)-5-((2-(trifluoromethyl)pyrimidin-4-yl)oxy)pentanoic acid (S)-3-(2-(4-benzyl-3-oxopiperazin-1-yl)acetamido)-4-oxo-5-((2-(trifluoromethyl)pyrimidin-4-yl)oxy)pentanoic acid (S)-3-(2-(4-benzyl-3-oxopiperazin-1-yl)acetamido)-5-(3,5-bis(trifluoromethyl)phenoxy)-4-oxopentanoic acid (S)-5-(3,5-bis(trifluoromethyl)phenoxy)-4-oxo-3-(2-(4-(phenylsulfonyl)piperazin-1-yl)acetamido)pentanoic acid (S)-3-(2-(4-benzyl-2-oxopiperazin-1-yl)acetamido)-5-(3,5-bis(trifluoromethyl)phenoxy)-4-oxopentanoic acid (S)-3-(2-(4-benzyl-2,3-dioxopiperazin-1-yl)acetamido)-5-(3,5-bis(trifluoromethyl)phenoxy)-4-oxopentanoic acid (S)-3-(2-(4-benzyl-2,5-dioxopiperazin-1-yl)acetamido)-5-(3,5-bis(trifluoromethyl)phenoxy)-4-oxopentanoic acid (S)-5-(3,5-bis(trifluoromethyl)phenoxy)-4-oxo-3-(2-(2-oxo-4-(phenylsulfonyl)piperazin-1-yl)acetamido)pentanoic acid (S)-3-(2-(4-benzyl-2-oxo-3,4-dihydroquinoxalin-1(2H)-yl)acetamido)-5-(3,5-bis(trifluoromethyl)phenoxy)-4-oxopentanoic acid (S)-3-(2-(4-benzyl-2-oxo-3,4-dihydroquinoxalin-1(2H)-yl)acetamido)-4-oxo-5-(2,3,5,6-tetrafluorophenoxy)pentanoic acid (S)-3-(2-(4-benzyl-2,3-dioxo-3,4-dihydroquinoxalin-1(2H)-yl)acetamido)-4-oxo-5-(2,3,5,6-tetrafluorophenoxy)pentanoic acid, (S)-3-(2-(4-benzyl-2,3-dioxopiperazin-1-yl)acetamido)-4-oxo-5-(2,3,5,6-tetrafluorophenoxy)pentanoic acid, (S)-3-(2-(4-benzoyl-2-oxopiperazin-1-yl)acetamido)-4-oxo-5-(2,3,5,6-tetrafluorophenoxy)pentanoic acid, (S)-3-(2-(4-benzyl-2-oxopiperazin-1-yl)acetamido)-5-(3,5-bis(trifluoromethyl)phenoxy)-4-oxopentanoic acid, (S)-3-(2-(4-benzyl-2,5-dioxopiperazin-1-yl)acetamido)-4-oxo-5-(2,3,5,6-tetrafluorophenoxy)pentanoic acid, (S)-3-(2-(4-benzyl-2-oxo-3,4-dihydroquinoxalin-1(2H)-yl)acetamido)-4-oxo-5-(2,3,5,6-tetrafluorophenoxy)pentanoic acid, (S)-3-(2-((R)-4-benzyl-3-methyl-2-oxopiperazin-1-yl)acetamido)-4-oxo-5-(2,3,5,6-tetrafluorophenoxy)pentanoic acid, (S)-3-(2-(4-benzoyl-3-oxopiperazin-1-yl)acetamido)-4-oxo-5-(2,3,5,6-tetrafluorophenoxy)pentanoic acid, and (S)-3-(2-((S)-4-benzyl-3-methyl-2-oxopiperazin-1-yl)acetamido)-4-oxo-5-(2,3,5,6-tetrafluorophenoxy)pentanoic acid.

19. A pharmaceutical composition, comprising the compound of claim 1 and a pharmaceutically acceptable carrier.

20. A method of treating a liver disease, gastrointestinal disease, respiratory disease, cardiovascular disease, disease associated with ischemic injury, dermatological disease, rheumatological disease, kidney disease, autoimmune disease, CNS disease, viral infection or inflammatory disease comprising administering a therapeutically effective amount of the compound of claim 1 to the patient in need of such treatment.

* * * * *